United States Patent
Becker et al.

(10) Patent No.: US 11,499,008 B2
(45) Date of Patent: Nov. 15, 2022

(54) FUNCTIONALIZED POLY (PROPYLENE FUMARATE) POLYMERS MADE BY RING OPENING POLYMERIZATION USING MAGNESIUM CATALYSTS

(71) Applicants: Matthew Becker, Stow, OH (US); James A. Wilson, Wolverhampton (GB); Yusheng Chen, Akron, OH (US)

(72) Inventors: Matthew Becker, Stow, OH (US); James A. Wilson, Wolverhampton (GB); Yusheng Chen, Akron, OH (US)

(73) Assignee: University of Akron, Akron, OH (US)

( * ) Notice: Subject to any disclaimer, the term of this patent is extended or adjusted under 35 U.S.C. 154(b) by 477 days.

(21) Appl. No.: 16/483,122

(22) PCT Filed: Feb. 2, 2018

(86) PCT No.: PCT/US2018/016627
§ 371 (c)(1),
(2) Date: Aug. 2, 2019

(87) PCT Pub. No.: WO2018/144849
PCT Pub. Date: Aug. 9, 2018

(65) Prior Publication Data
US 2019/0359766 A1 Nov. 28, 2019

Related U.S. Application Data

(60) Provisional application No. 62/561,722, filed on Sep. 22, 2017, provisional application No. 62/541,889, filed on Aug. 7, 2017, provisional application No. 62/509,340, filed on May 22, 2017, provisional application No. 62/500,777, filed on May 3, 2017, provisional application No. 62/453,724, filed on Feb. 2, 2017, provisional application No. 62/453,786, filed on Feb. 2, 2017.

(51) Int. Cl.

| | |
|---|---|
| *C08G 63/52* | (2006.01) |
| *C08G 63/682* | (2006.01) |
| *C08G 63/685* | (2006.01) |
| *C08G 63/91* | (2006.01) |
| *C08G 65/332* | (2006.01) |
| *C08L 63/10* | (2006.01) |
| *C08G 63/08* | (2006.01) |
| *C08G 63/82* | (2006.01) |

(Continued)

(52) U.S. Cl.
CPC ............ *C08G 63/52* (2013.01); *C08G 63/08* (2013.01); *C08G 63/682* (2013.01); *C08G 63/6858* (2013.01); *C08G 63/823* (2013.01); *C08G 63/918* (2013.01); *C08G 65/3322* (2013.01); *C08G 81/027* (2013.01); *C08L 63/10* (2013.01); *A61L 27/18* (2013.01); *B33Y 70/00* (2014.12); *B33Y 80/00* (2014.12)

(58) Field of Classification Search
CPC ...... C08G 63/52; C08G 63/08; C08G 63/682; C08G 63/6858; C08G 63/688; C08G 63/823; C08G 63/83; C08G 63/91; C08G 63/918; C08G 65/3322; C08G 81/027; C08G 63/676; C08G 63/685; C08L 67/06; C08L 63/10
See application file for complete search history.

(56) References Cited

U.S. PATENT DOCUMENTS

| | | | |
|---|---|---|---|
| 3,538,043 A | 11/1970 | Herold | |
| 3,857,821 A * | 12/1974 | Becker | C08F 20/40 526/285 |

(Continued)

FOREIGN PATENT DOCUMENTS

| | | |
|---|---|---|
| WO | 95/29710 A1 | 11/1995 |
| WO | 2002/085246 A2 | 10/2002 |

(Continued)

OTHER PUBLICATIONS

Shyeni Paul et al "Ring-opening copolymerization (ROCOP): synthesis and properties of polyesters and polycarbonates", Chem. Commun., 2015, 51, 6459-6479 (Year: 2015).*

(Continued)

*Primary Examiner* — Frances Tischler
*Assistant Examiner* — Gennadiy Mesh
(74) *Attorney, Agent, or Firm* — Renner, Kenner, Greive, Bobak, Taylor & Weber

(57) ABSTRACT

An end and monomer functionalized poly(propylene fumarate) polymer and methods for preparing this polymer, comprising isomerized residue of a maleic anhydride monomer and a functionalized propylene oxide monomer according to the formula:

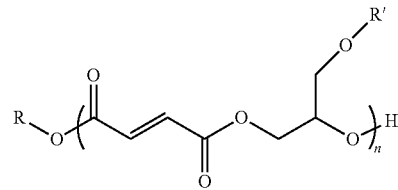

where n is an integer from more than 1 to 100; R is the residue of an initiating alcohol having a propargyl, norbornene, ketone or benzyl functional group; and R' is a second functional group selected from the group consisting of propargyl groups, 2-nitrophenyl groups, and combinations thereof are disclosed. The end and monomer functional groups allow for post-polymerization modification with bioactive materials using "click" chemistries and use of the polymer for a variety of applications in medical fields, including, for example, 3-D printed polymer scaffold.

8 Claims, 21 Drawing Sheets

Specification includes a Sequence Listing.

(51) Int. Cl.
*C08G 81/02* (2006.01)
*B33Y 70/00* (2020.01)
*B33Y 80/00* (2015.01)
*A61L 27/18* (2006.01)

(56) References Cited

U.S. PATENT DOCUMENTS

| | | | | |
|---|---|---|---|---|
| 4,888,413 | A * | 12/1989 | Domb | A61L 24/046 |
| | | | | 525/445 |
| 5,527,864 | A | 6/1996 | Suggs et al. | |
| 6,124,373 | A | 9/2000 | Peter et al. | |
| 6,306,821 | B1 | 10/2001 | Mikos et al. | |
| 6,423,790 | B1 * | 7/2002 | He | A61L 27/50 |
| | | | | 525/445 |
| 7,629,388 | B2 * | 12/2009 | Mikos | A61K 47/60 |
| | | | | 514/772.3 |
| 7,649,022 | B2 | 1/2010 | Gomurashvili et al. | |
| 8,445,007 | B2 | 5/2013 | Gomurashvili et al. | |
| 8,652,504 | B2 | 2/2014 | Li et al. | |
| 8,765,164 | B2 | 7/2014 | Katsarava et al. | |
| 8,809,212 | B1 | 8/2014 | Dirk et al. | |
| 8,974,815 | B2 | 3/2015 | Chu et al. | |
| 2010/0311941 | A1 * | 12/2010 | Coates | C08G 63/42 |
| | | | | 528/405 |
| 2013/0071930 | A1 * | 3/2013 | Chu | A61L 27/54 |
| | | | | 525/379 |
| 2015/0018497 | A1 * | 1/2015 | Farrugia | C08G 63/08 |
| | | | | 528/356 |

FOREIGN PATENT DOCUMENTS

| | | |
|---|---|---|
| WO | 2016/081587 A1 | 5/2016 |
| WO | 2016/172681 A1 | 10/2016 |

OTHER PUBLICATIONS

Yuanyuan Luo ey al "Synthesis and Biological Evaluation of Well-Defined Poly(propylene fumarate) Oligomers and Their Use in 3D Printed Scaffolds", Biomacromolecules 2016, 17, 690-697 (Year: 2016).*

Seongbong Jo et al "Modification of Oligo(poly(ethylene glycol) fumarate) Macromerwith a GRGD Peptide for the Preparation of Functionalized Polymer Networks", Biomacromolecules 2001, 2, 255-261 (Year: 2001).*

Kurtis Kasper et al "Synthesis of poly(propylene fumarate)", Nature Protocols, vol. 4, No. 4 , 2009 | (Year: 2009).*

Japanese Office Action in Japanese Application No. 2019-541725, dated Jan. 12, 2022.

Written Opinion of the International Searching Authority in PCT/US2018/016627 dated Apr. 6, 2018.

Shung A.K. et al., "Kinetics of poly(propylene fumarate) synthesis by step polymerization of diethyl fumarate and propylene glycol using zinc chloride as a catalyst," Journal of Biomaterials Science. Polymer Edition vol. 13, No. 1, p. 95 (2002).

Angela M. DiCiccio and Geoffrey W. Coates, "Ring-Opening Copolymerization of Maleic Anhydride with Epoxides: A Chain-Growth Approach to Unsaturated Polyesters," J. Am. Chem. Soc. 201, 133, 10724-10727.

Shigenobu Takenouchi, Akinori Takasu, Yoshihito Inai, and Tadamichi Hirabayashi, "Effects of Geometrical Difference of Unsaturated Aliphatic Polyesters on Their Biodegradability II. Isomerization of Poly(maleic anhydride-co-propylene oxide) in the Presence of Morpholine," Polymer Journal, vol. 34, No. 1, pp. 36-42 (2002).

Sobczak, M., "Ring-opening polymerization of cyclic esters in the presence of choline/SnOct2 catalytic system," Polym. Bull. (2012) 68:2219-2228 (Published online Dec. 4, 2011).

Lee, et al., "Fabrication and Characterization of Poly(Propylene Fumarate) Scaffolds with Controlled Pore Structures Using 3-Dimensional Printing and Injection Molding", University of South Carolina Scholar Commons Oct. 2006.

Fryhle et al., "Isomerization of Dimethyl Maleate to Dimethyl Fumarate" Journal of Chemical Education, vol. 68 No. 12 Dec. 1991, 1050-1051.

* cited by examiner

SEQUENCE LISTING

<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Synthetic peptide sequence

<400> SEQUENCE: 1

Gly Arg Gly Asp Ser
1               5

FUNCTIONALIZED POLY (PROPYLENE FUMARATE) POLYMERS MADE BY RING OPENING POLYMERIZATION USING MAGNESIUM CATALYSTS

CROSS REFERENCE TO RELATED APPLICATIONS

This application claims the benefit of U.S. provisional patent application Ser. No. 62/543,786 entitled "Block Copolymers Of Lactones And Poly(Propylene Fumarate)" filed Feb. 2, 2017, U.S. provisional patent application Ser. No. 62/453,724 entitled "Copolymerization of Propylene Oxide And Maleic Anhydride using Mg Catalysts with Functional Initiators," filed Feb. 2, 2017, U.S. provisional patent application Ser. No. 62/500,777 entitled "Post-3D Printing Functionalization Polymer Scaffolds for Enhanced Bioactivity," filed May 3, 2017, U.S. provisional patent application Ser. No. 62/509,340 entitled "Functionalized Poly(Propylene Fumarate) Polymers and Methods for Their Making," filed May 22, 2017, U.S. provisional patent application Ser. No. 62/541,889 entitled "Synthesis and Characterization of Well Defined Poly(propylene fumarate) and Poly(ethylene glycol) Block Copolymers," filed Aug. 7, 2017, U.S. provisional patent application Ser. No. 62/561,722 entitled "Mg Catalyzed Production of Poly(propylene fumarate) in Hexanes," filed Sep. 22, 2017, and U.S. patent application entitled "Block Copolymers of Lactones and Poly(Propylene Fumarate)," filed herewith by the Applicant on Feb. 2, 2018, all of which are incorporated herein by reference in their entirety.

SEQUENCE LISTING

The Sequence Listing text file entitled "UOA1310PCT_ST25" having a size of 725 bytes and creation date of Mar. 26, 2018, that was electronically filed with the patent application is incorporated herein by reference in its entirety.

NAMES OF THE PARTIES TO A JOINT RESEARCH AGREEMENT

The present application is subject to a Joint Research Agreement between the University of Akron of Akron, Ohio and 21$^{st}$ Century Medical Technologies, Inc., of Akron, Ohio.

FIELD OF THE INVENTION

One or more embodiments of the present invention relates to a novel poly(propylene fumarate) polymer and methods for making poly(propylene fumarate) polymers. In certain embodiments, the present invention relates to a well-defined biodegradable poly(propylene fumarate) polymer and scalable methods for making and functionalizing same. In certain embodiments, the present invention relates to a well-defined biodegradable poly(propylene fumarate) polymer for use in various regenerative medicine applications.

BACKGROUND OF THE INVENTION

As will be appreciated, tissue engineering is an interdisciplinary field that applies the principles of engineering and life sciences to the development of biological substitutes that restore, maintain, or improve tissue function and are applicable to a variety of therapeutic targets such as blood vessels, nerves and bone treatment. There are two commonly used methods for tissue engineering. One method is implanting cells into a supporting structural device, which is termed a scaffold. The other method is allowing cells to remodel the scaffold into natural tissue before implanting it into a patient's body. Based on these tissue engineering principles, scaffolds play a critical role in tissue engineering applications. Therefore, the material that makes up the scaffold is important for tissue engineering as well. Material are needed which satisfies all or almost all requirements for bone tissue engineering and can be processed to be a scaffold. A general material for tissue engineering must serve the bulk mechanical and structural requirements of the target tissue when it forms a scaffold and enable it to have molecular interactions with cells that promote tissue healing. Moreover, low toxicity and rapid biodegradability are basic properties that the material should possess.

Materials already in use as scaffolds, such as metals, ceramics, natural and synthetic polymers have all failed to meet these requirements. Of these materials, however, synthetic polymers could provide a possible route to a suitable scaffold material because of the ability to tune their mechanical and physical properties. For example, poly(propylene fumarate) (PPF), a type of polyester, has been synthesized and researched for bone tissue engineering.

Further, advances in additive manufacturing (such as 3D printing) have the potential to greatly change tissue engineering for a variety of reasons, not the least of which is that these techniques have the potential to make it possible to quickly design and print scaffolds to meet a patients specific requirements. However, these advances will be highly dependent on the availability of printable materials that meet the chemical, mechanical and biological requirements of the specific application. Various forms of additive manufacturing, more colloquially known as 3D printing, have been demonstrated in the literature. Fused deposition modelling (FDM) is a layer-by-layer method of extrusion molding solid filaments, such as poly(urethane)s (PUs), poly(L-lactic acid) (PLLA) or poly(ester urea)s (PEUs). Polymeric resins can also be printed using continuous digital light processing (cDLP), wherein photo-crosslinking in specific regions is achieved through high resolution stereolithography. Inkjet methods have also been demonstrated in 3D printing and can be used with either powders or resins.

In order to produce 3D scaffolds that are compatible with biological systems, the polymer should be non-toxic, implantable without rejection and completely resorbable upon degradation. While the first two criteria are achieved in a multitude of polymer systems, there are relatively few examples that are also bioresorbable; polylactides, poly(ε-caprolactone) (PCL) and poly(propylene fumarate) (PPF). Each of these examples are polyesters and thus, able to degrade either enzymatically or through hydrolysis in vivo. However, as a consequence of the rapid degradation of PLLA, acidosis and inflammation of the surrounding tissue area are regularly observed. Conversely, the slow degradation of PCL in the human body limits its use in tissue repair, particularly with regards to reforming vascular tissue.

Both PLLA and PCL can be extruded through FDM to produce 3D scaffolds capable of undergoing in vitro degradation. While the materials exhibit moderate mechanical and tensile properties, the majority of defects in the material are observed at the interface between deposited layers. Furthermore, as a consequence of the achievable width of the extrusion nozzle in FDM, the resolution of the 3D printed scaffold is limited.

Stereolithographic methods, such as cDLP, however, have been shown to exhibit much higher resolution compared to FDM techniques, as they are limited by the light source of the printer rather than the materials used. This enables 3D scaffolds to be printed with a controlled porosity that can be tailored to match physiological conditions.

PPF is an unsaturated polyester that degrades in vivo to form fumaric acid and propylene glycol, which are excreted naturally. PPF has been used for a variety of medical applications, such as vascular stents, nerve grafts, cartilage, drug release vehicles, blood vessel engineering, and bone tissue engineering. As a consequence of the unsaturated alkene in the polymer backbone, intermolecular crosslinking can be achieved in order to strengthen the mechanical properties of the material. The development of a printable PPF resin by dissolving the polymer into the reactive diluent diethyl fumarate (DEF), which acts as both solvent and crosslinking agent, has been extensively studied and shown to be able to produce 3D scaffolds with compressive moduli comparable to bone.

The current method of PPF production is through the step-growth polycondensation of DEF and propylene glycol (Scheme 1). However, this is not an industrially viable method of production for PPF for 3D printing purposes. Only low molecular mass PPF (<3000 Da) has been demonstrated in cDLP systems as a consequence of increasing crystallinity with chain length leading to a solid polymer with low solubility, as opposed to a fluidic oligomer observed at lower molecular masses. Thus, scale-up and commercialization of PPF for 3D printing via step-growth polycondensation has proven difficult. Step growth methods are not conducive to maintaining high end-group fidelity and narrow molecular mass distribution. The lack of control over the molecular mass distributions directly affects the degradation properties of the material. Residual ethanol and unreacted monomers as a by-product of step-growth polycondensation conditions have also led to purification issues for the industrial scaling of PPF.

The ring-opening (co)polymerization (ROCOP) of maleic anhydride (MAn) and propylene oxide (PO) has been previously reported to produce the PPF cis-alkene isomer poly(propylene maleate) (PPM), which can be transformed into PPF using a weak base at low (~60° C.) temperatures. Advantageously, ROCOP allows for a high degree of control over the molecular mass distribution and end-group fidelity through the variance of the ratio of monomer(s) to alcohol initiator. Recent studies of PPF synthesis via ROP, including contact cytotoxicity assays and cell culture results, have shown that PPF polymers produced by ROP are non-toxic and that cells attached and proliferated well on its thin films. While examples in the literature already exist of PPM produced using ROCOP, these systems have been based on using metal alkoxide catalyst/chain transfer agents that have limited options in terms of the alcohol used as an initiating end group.

Previously, magnesium ethoxide (Mg(OEt)$_2$) was shown to exhibit catalytic behavior toward the ROCOP formation of PPM. Magnesium, while not typically used in catalysis as a consequence of its reactivity is attractive for biomaterials synthesis in that the terminal oxidation product, magnesium oxide, is used as a food additive. However, in the case of Mg(OEt)$_2$, end-group fidelity is not achievable as a consequence of the weakly coordinated ethoxide ligand also acting as a chain transfer species. The resulting polymers are either ethoxy- or hydroxy-terminal species. Magnesium 2,6-di-tert-butyl-4-methylphenoxide (Mg(BHT)$_2$(THF)$_2$) is a catalyst that has previously been demonstrated as an 'immortal' ROP catalyst for lactones, which can be used to produce high end-group fidelity polyesters at low catalytic loading. Advantageously, the catalyst exhibits relative stability in 'air' conditions and does not promote initiation/transesterification side reactions in the presence of water. Significantly, 2,6-di-tert-butyl-4-methylphenoxide (BHT) was initially chosen as a ligand system as a consequence of its use as an antioxidant and stabilizer in food and packaging. This limited biocompatibility concerns.

Critical to the utility of PPF is the ability to control both functional group stoichiometry and degradation properties. In order for PPF to be a completely bioresorbable material, the incorporation of MAn and PO must perfectly alternate to produce a polyester able to undergo facile hydrolysis and avoid side reactions that may incorporate polyether linkages between consecutive PO repeat units, which are not readily degradable. Controlled degradation is imperative in many applications to enable the scaffold to degrade as the tissue grows, maximizing the mechanical contribution of the scaffold and ensuring effective replacement with bone tissue. Polymers with lower molecular mass distribution ($Đ_M$) are known to degrade more uniformly than high $Đ_M$ polymers, enabling better control over the scaffold degradation.

In order to minimize implant rejection by the body and facilitate the repair process, post-polymerization modification of the surface of implants with bioconjugates has been extensively investigated. The addition of small molecules and polypeptides to a scaffold surface has been shown to assist cell attachment and spreading on the surface of a Scheme 1
Polymerization methods for producing poly(propylene fumarate)

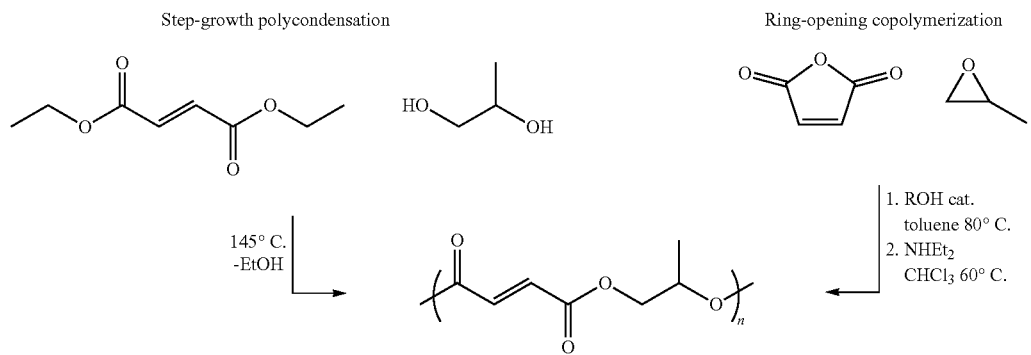

scaffold. Furthermore, with selective choice of the polypeptides, the differentiation of those cells can be targeted to produce a specified tissue growth (e.g. bone tissue). However, a scaffold for tissue growth repair must be able to influence cell attachment, proliferation, and differentiation to ensure only the desired tissue is formed, which has not yet been demonstrated using functionalized PPF. The harsh photochemical crosslinking conditions destroy most functional groups and have limited the ability to incorporate bioactive species using previously described methods.

One of the problems for current PPF polymers, however, is that non-functionalized PPF does not have interactions with cells, which is a critical requirement for a successful biomaterial. Hence, PPF properties need to be improved further, although its synthetic method has been improved and it already satisfies some of the basic requirements for bone tissue engineering, as a consequence of its fully bioresorbable nature and lack of observable toxicity. As will be appreciated, a general pathway to improve synthetic polymer bioactivity properties is to functionalize the polymer with something that has or is capable of obtaining the desired properties. Because the final goal is to improve PPF bioactivities, the ability to add one or more functional groups to the PPF that can undergo "click" type or other reactions that give the PPF the ability to undergo surface modification and attach helpful bioactive molecules after printing is desired.

Accordingly, what is needed in the art is a well-defined, non-toxic, and biodegradable PPF polymer that has tunable mechanical properties and is functionalized with one or more functional groups to the PPF that can undergo "click" type or other reactions that give it the ability to undergo surface modification and attach helpful bioactive molecules after 3-D printing, as well as methods for making and using such a polymer.

SUMMARY OF THE INVENTION

In one or more embodiments, the present invention provide a well-defined, non-toxic, and biodegradable PPF polymer that has tunable mechanical properties and is functionalized with one or more functional groups so the PPF that can undergo "click" type or other reactions that give it the ability to undergo surface modification and attach helpful bioactive molecules after 3-D printing, as well as methods for making and using such a polymer. In some embodiments, these functionalized PPF polymers are formed using a 2-step process wherein an end functionalized poly(propylene maleate) (PPM) polymer intermediate is formed in a first step by the ring-opening polymerization of maleic anhydride and propylene oxide, using an initiating alcohol having a functional end group, and a magnesium catalyst. The PPM polymer intermediate is then isomerized in a second step to form the end functionalized PPF polymer. In some other embodiments, the present invention obtains novel functionalized PPF polymers by functionalizing one of the comonomers used to synthesize the PPF via ROP to add functional sites that give these PPF materials the ability to attach some small bioactive molecules. The propylene oxide comonomer was chosen for functionalization in these embodiments of the present invention, since the alkene bond from maleic anhydride acts as the photo-crosslinking site of the polymer, making it difficult to find reaction sites for functionalizing the maleic anhydride co monomer.

In these embodiments, the propylene oxide functionalized comonomer is first obtained using phase transfer chemistry, and after purification, is polymerized with maleic anhydride and an initiating alcohol (which may or may not be functionalized) using a magnesium catalyst to form a novel functionalized poly(propylene maleate) polymers, which are then isomerized to form novel functionalized PPF polymers of the present invention. The chemical structures of functionalized comonomers and polymers according to various embodiments of the present invention have been characterized by $^1$H NMR, $^{13}$C NMR and $^1$H-$^1$H COSY spectroscopies. High end-group fidelity of polymers has been proved by MALDI-ToF mass spectroscopy. In various embodiments of the present invention, the functionalized PPF polymers of the present invention had molecular weights of ca. 1000-2000 Da, which is suitable for 3D printing to produce PPF scaffolds. These novel functionalized PPF polymers also exhibited low dispersity. Moreover, it was found that enough of the functional groups attached to these functionalized PPF polymers survive 3D printing into PPF structures by conventional photo crosslinking methods to produce functionalized PPF scaffolds having a robust ability to be modified for perfect bone and/or other tissue engineering devices.

In a first aspect, the present invention is directed to an end or monomer functionalized poly(propylene fumarate) polymer. In one or more embodiment, functionalized poly(propylene fumarate) polymer of the present invention comprises the isomerized residue of a maleic anhydride monomer and the residue of a functionalized propylene oxide monomer. In one or more of these embodiments, the end or monomer functionalized poly(propylene fumarate) polymer of the present comprises the residue of a functionalized initiating alcohol.

In one or more embodiments, the end or monomer functionalized poly(propylene fumarate) polymer of the present invention includes any one or more of the above referenced embodiments of the first aspect of the present invention having the formula:

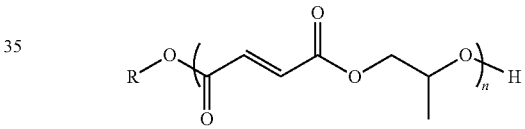

wherein n is an integer from 1 to 1000; and R is a functional group selected from the group consisting of alkyne groups, propargyl groups, allyl groups, alkene groups, 4-dibenzyocyclooctyne groups, cyclooctyne groups, ketone groups, aldehyde groups, tertiary halogen groups, and combinations thereof. In one or more embodiments, the end or monomer functionalized poly(propylene fumarate) polymer of the present invention includes any one or more of the above referenced embodiments of the first aspect of the present invention having the formula:

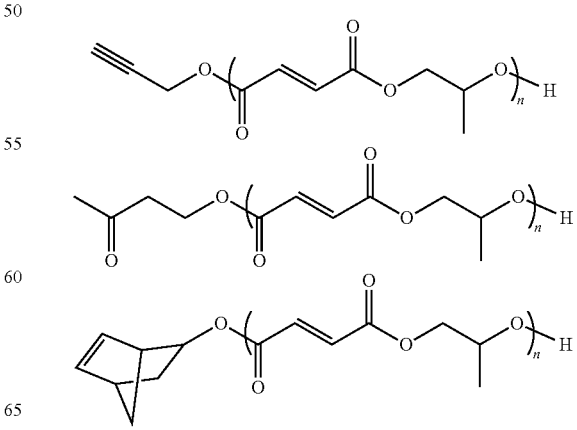

wherein n is an integer from 1 to 1000.

In one or more embodiments, the end or monomer functionalized poly(propylene fumarate) polymer of the present invention includes any one or more of the above referenced embodiments of the first aspect of the present invention, wherein the functionalized initiating alcohol is selected from propargyl alcohol, allyl alcohol, 4-dibenzyocyclooctynol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, α-bromoisobtyryl 4-methanol benzylmethanoate, or a combination thereof.

In one or more embodiments, the end or monomer functionalized poly(propylene fumarate) polymer of the present invention includes any one or more of the above referenced embodiments of the first aspect of the present invention, wherein the functionalized propylene oxide monomer is selected from an alkyne functionalized propylene oxide, 2-[[(2-nitrophenyl)methoxy]methyl]oxirane (NMMO), glycidyl propargyl ether, (±)-epichlorohydrin, or a combination thereof. In one or more embodiments, the end or monomer functionalized poly(propylene fumarate) polymer of the present invention includes any one or more of the above referenced embodiments of the first aspect of the present invention, wherein the functionalized initiating alcohol comprises a functional group selected from alkyne groups, propargyl groups, allyl groups, alkene groups, 4-dibenzyocyclooctyne groups, cyclooctyne groups, ketone groups, aldehyde groups, tertiary halogen groups, and combinations thereof.

In one or more embodiments, the end or monomer functionalized poly(propylene fumarate) polymer of the present invention includes any one or more of the above referenced embodiments of the first aspect of the present invention having the formula:

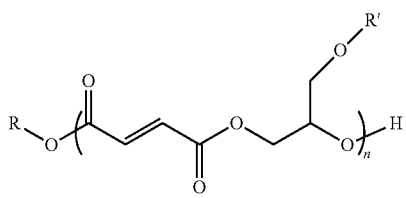

where n is an integer from 1 to 100; R is a functional group selected from benzyl groups, alkyne groups, propargyl groups, allyl groups, alkene groups, 4-dibenzyocyclooctyne groups, cyclooctyne groups, ketone groups, aldehyde groups, tertiary halogen groups and poly(ethylene glycol) groups, or a combination thereof; and R' is a functional group, or an alkyl or aryl group having a functional group, wherein the functional group is an alkyne group, an alkene group, a hydroxyl group, a protected hydroxyl group, thiol group, halide group, or a combination thereof. In one or more embodiments, the end or monomer functionalized poly(propylene fumarate) polymer of the present invention includes any one or more of the above referenced embodiments of the first aspect of the present invention having a formula selected from:

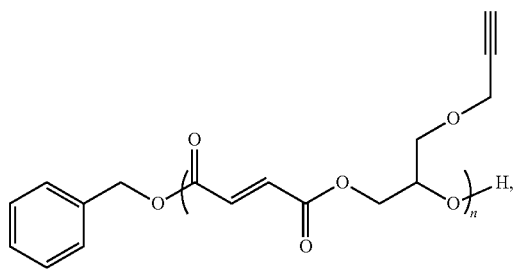

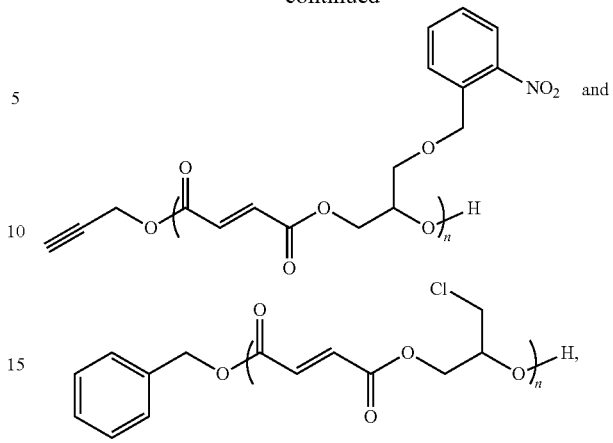

where n is an integer from about 1 to about 100.

In one or more embodiments, the end or monomer functionalized poly(propylene fumarate) polymer of the present invention includes any one or more of the above referenced embodiments of the first aspect of the present invention having a number average molecular weight ($M_n$) of from about 0.7 kDa to about 100,000 kDa. In one or more embodiments, the end or monomer functionalized poly(propylene fumarate) polymer of the present invention includes any one or more of the above referenced embodiments of the first aspect of the present invention having a polydispersity index ($Đ_M$) of from about 1.01 to about 1.8.

In a second aspect, the present invention is directed to a functionalized propylene oxide monomer for forming the monomer functionalized poly(propylene fumarate) polymer comprising a glycidyl group connected directly or through an ether bond to a functional group, or an alkyl or aryl group comprising a functional group, wherein the functional group is capable of entering into a click reaction with a corresponding functional group. In one or more of these embodiments, the functional group is selected from alkyne groups, alkene groups, hydroxyl groups, protected hydroxyl groups, or a combination thereof.

In one or more embodiments, the functionalized monomer of the present invention includes any one or more of the above referenced embodiments of the second aspect of the present invention, wherein the functionalized monomer is glycidyl propargyl ether. In one or more embodiments, the functionalized monomer of the present invention includes any one or more of the above referenced embodiments of the second aspect of the present invention having the formula:

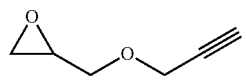

In one or more embodiments, the functionalized monomer of the present invention includes any one or more of the above referenced embodiments of the second aspect of the present invention, wherein the functionalized monomer is 2-[[(2-nitrophenyl)methoxy]methyl]oxirane (NMMO). In one or more embodiments, the functionalized monomer of the present invention includes any one or more of the above referenced embodiments of the second aspect of the present invention having the formula:

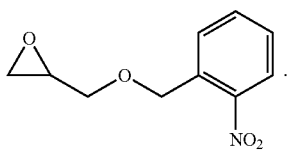

In a third aspect, the present invention is directed to a functionalized propylene oxide monomer for forming the monomer functionalized poly(propylene fumarate) polymer of the first aspect of the present invention having the formula:

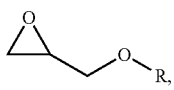

where R is a functional group, or an alkyl or aryl group comprising a functional group, that is selected from alkyne groups, alkene groups, hydroxyl groups, protected hydroxyl groups, thiol groups, halide groups, or a combination thereof. In one or more of these embodiments, the functionalized propylene oxide monomer has the formula:

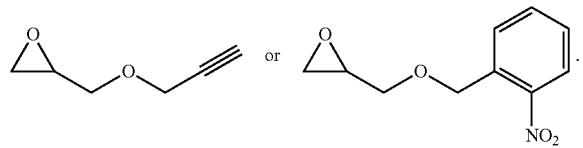

In a fourth aspect, the present invention is directed to a functionalized propylene oxide monomer for forming the monomer functionalized poly(propylene fumarate) polymer of the first aspect of the present invention, having the formula:

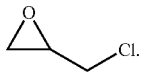

In a fifth aspect, the present invention is directed to a method for making the end or monomer functionalized poly(propylene fumarate) polymer of the first aspect of the present invention comprising: preparing an initiating alcohol, the initiating alcohol further comprising a functional end group; combining the initiating alcohol, a magnesium catalyst, maleic anhydride, and propylene oxide in a suitable vessel and adding a suitable solvent; sealing and then heating the vessel to cause and/or maintain a ring opening polymerization reaction between the maleic anhydride and propylene oxide, initiated by the initiating alcohol, thereby forming a poly(propylene maleate) polymer comprising the functional end group; collecting and purifying the poly(propylene maleate) polymer comprising the functional end group; and isomerizing the poly(propylene maleate) polymer comprising the functional end group to for a poly(propylene fumarate) polymer comprising the functional end group. In one or more of these embodiments, the molar ratio of the initiating alcohol to the magnesium catalyst in the combination is about 1:1.

In one or more embodiments, the method of the present invention includes any one or more of the above referenced embodiments of the fifth aspect of the present invention, wherein the ratio of the moles of the initiating alcohol to the total number of moles of monomer (the maleic anhydride and the functionalized and/or unfunctionalized propylene oxide) in the combination is from about 1:5 to about 1:1000. In one or more embodiments, the method of the present invention includes any one or more of the above referenced embodiments of the fifth aspect of the present invention, wherein the total monomer concentration (the maleic anhydride and the functionalized and/or unfunctionalized propylene oxide) in the solution is from about 0.5M to about 5.0M. In one or more embodiments, the method of the present invention includes any one or more of the above referenced embodiments of the fifth aspect of the present invention, wherein the suitable solvent is toluene or hexane.

In one or more embodiments, the method of the present invention includes any one or more of the above referenced embodiments of the fifth aspect of the present invention, wherein the step of heating comprises heating the vessel to a temperature of from about 40° C. to about 100° C. In one or more embodiments, the method of the present invention includes any one or more of the above referenced embodiments of the fifth aspect of the present invention, wherein the suitable solvent is hexane and the step of heating comprises heating the vessel to a temperature of about 45° C.

In one or more embodiments, the method of the present invention includes any one or more of the above referenced embodiments of the fifth aspect of the present invention, wherein the initiating alcohol is selected from benzyl alcohol, propargyl alcohol, allyl alcohol, 4-dibenzyocyclooctynol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, α-bromoisobtyryl 4-methanol benzylmethanoate, and combinations thereof. In one or more embodiments, the method of the present invention includes any one or more of the above referenced embodiments of the fifth aspect of the present invention, wherein the functional end group of the initiating alcohol comprises alkyne groups, propargyl groups, allyl groups, alkene groups, 4-dibenzyocyclooctyne groups, cyclooctyne groups, ketone groups, aldehyde groups, tertiary halogen groups, poly(ethylene glycol) groups and combinations thereof. In one or more embodiments, the method of the present invention includes any one or more of the above referenced embodiments of the fifth aspect of the present invention, wherein the magnesium catalyst comprises $Mg(BHT)_2(THF)_2$.

In a sixth aspect, the present invention is directed to a method for making the functionalized poly(propylene fumarate) polymer of the first aspect of the present invention comprising: preparing a functionalized propylene oxide; reacting the functionalized propylene oxide with maleic anhydride and an initiating alcohol in the presence of a magnesium catalyst to form a functionalized poly(propylene maleate) polymer; isomerizing the functionalized poly(propylene maleate) polymer by reacting it with a base to form the functionalized poly(propylene fumarate) polymer of the first aspect of the present invention. In one or more of these embodiments, the functionalized propylene oxide is selected from an alkyne functionalized propylene oxide, 2-[[(2-nitrophenyl)methoxy]methyl]oxirane (NMMO), glycidyl propargyl ether, (±)-epichlorohydrin or a combination thereof. In some of these embodiments, the initiating alcohol is a functionalized initiating alcohol selected from is selected from benzyl alcohol, propargyl alcohol, allyl alcohol, 4-dibenzyocyclooctynol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, α-bromoisobtyryl 4-methanol benzylmethanoate, and combinations thereof. In one or more of these embodiments, the metal catalyst is magnesium 2,6-di-tert-butyl-4-methylphenoxide ($Mg(BHT)_2(THF)_2$).

In a seventh aspect, the present invention is directed to a method of making the functionalized monomer of the first aspect of the present invention comprising: adding propargyl alcohol to an aqueous solution containing a base selected from the group consisting or sodium hydroxide (NaOH), potassium hydroxide (KOH), and combinations thereof; dissolving (±)-epichlorohydrin and tetrabutylammonium hydrogensulfate in a suitable organic solvent; adding the solution and $H_2O$ to the propargyl alcohol solution; and allowing the reaction to proceed under an inert atmosphere to produce glycidyl propargyl ether.

In some of these embodiments, the step of adding propargyl alcohol comprises adding the propargyl alcohol dropwise into an aqueous solution of sodium hydroxide (NaOH) at a temperature of from about −10° C. to about 30° C. while stirring, wherein the aqueous solution of sodium hydroxide (NaOH) comprises from about 20% to about 50% NaOH by weight; the organic solvent in the step of dissolving comprises hexane; and the step of allowing the reaction to proceed comprises allowing the reaction temperature to increase to ambient temperature and allowing the reaction to continue for from about 1 hours to about 24 hours under a $N_2$ blanket. In some other embodiments, the method further comprises: quenching the reaction; extracting the crude product with a suitable organic solvent; and purifying the crude product by column chromatography or distillation to produce purified glycidyl propargyl ether.

In an eighth aspect, the present invention is directed to a method of making a functionalized monomer comprising: dissolving o-nitrobenzyl alcohol in a suitable organic solvent; adding tetrabutylammonium hydrogensulfate and an aqueous solution containing a base to the o-nitrobenzyl alcohol solution, wherein the base is selected from the group consisting or sodium hydroxide (NaOH), potassium hydroxide (KOH), and combinations thereof; adding (±)-epichlorohydrin; and allowing the reaction to proceed to produce 2-[[(2-nitrophenyl)methoxy]methyl]oxirane (NMMO). In one or more of these embodiments, the method further comprises: extracting the crude product with a suitable organic solvent; and purifying the crude product by column chromatography or distillation to produce a purified 2-[[(2-nitrophenyl)methoxy]methyl]oxirane (NMMO).

In yet another aspect, the present invention is directed to a 3-D printed polymer scaffold comprising the functionalized poly(propylene fumarate) polymer of the first aspect of the present invention. In one or more of these embodiments, the 3-D printed polymer scaffold further comprises a plurality of bioactive materials bonded to the functionalized poly(propylene fumarate) polymer.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

Figure 1:
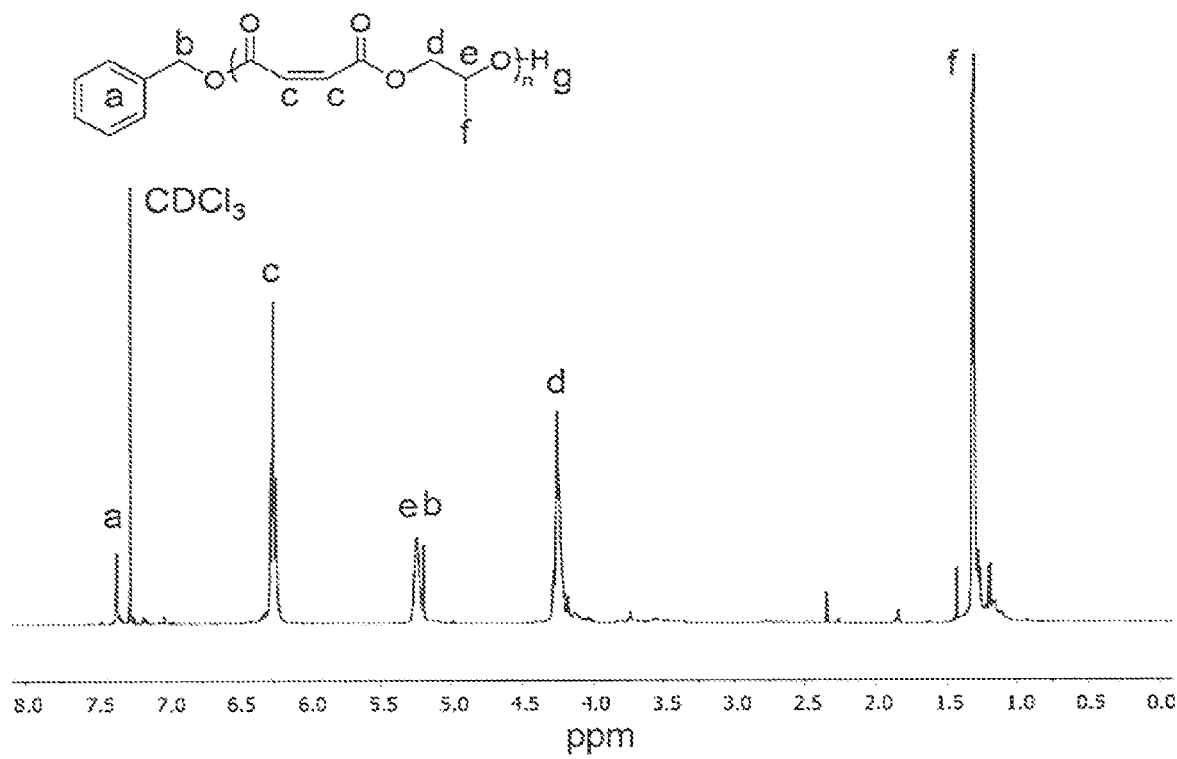
FIG. 1 is a $^1H$ NMR spectrum of DP 10 benzyl alcohol initiated poly(propylene maleate) (Table 2, Entry 1) using $Mg(BHT)_2(THF)_2$ as a catalyst (300 MHz, 303 K, DMSO-$d_6$).

As set forth above, because of its low cytotoxicity, good biodegradability and tunable mechanical properties, poly (propylene fumarate) (PPF) is an ideal synthetic polyester to make scaffolds for bone or other tissue engineering. However, based on tissue engineering requirements, PPF should ideally have molecular interactions with cells to help cells attach, proliferate and differentiate. Hence, the functionalization of PPF to attach bioactive molecules (i.e. bioactive drugs, peptides, proteins, sugar) is a critical step if it is to be used for bone tissue engineering applications. One of the more facile methods to modify synthetic polymers is to add functional groups for post-polymerization modification, which will modify chemical structure of polymer. Based on the PPF chemical structure and its synthetic route (i.e. ROCOP), there are two potential methods for functionalization. One is end-group functionalization via a functionalized initiating alcohol, and the other is via the functionalization of the monomer precursors, which then form functionalized side-chains on the PPM/PPF polymers upon polymerization ("monomer functionalized" PPM/PPF).

As used herein, the term "functionalized" refers to a polymer, bioactive material, or other substance that includes, or has been modified to include, a functional group and the broader term "functionalization" refers to a process, method and/or reaction whereby a functional group is added to a polymer, bioactive material, or other substance, and in particular, to the addition of a functional group to a PPF polymer (even if added before isomerization) and/or a bioactive material or other functional species, for the purpose of adding that bioactive material or other functional species to the PPF polymer. Further, as used herein the terms "functional group" and "functional moiety" are used interchangeably to refer a chemically active species or a group containing a chemically active species. As used herein, the "functionalized poly(propylene fumarate) polymer" refers to a poly(propylene fumarate) polymer comprising one or more functional groups for the purpose of adding bioactive materials of other functional species to the polymer.

Accordingly, the terms "end-group functionalized," or "end group functionalized" or "end functionalized," are used interchangeably to refer to a polymer that has or has been modified to include a functional group at a terminal end of a polymer chain and the terms "end-group functionalization," or "end group functionalization" or "end functionalization," are used interchangeably to refer to a process, method and/or reaction whereby a functional group is added to a terminal end of a polymer chain. The term "monomer functionalized," as used herein, refers to a PPM or PPF polymer having one or more functional groups that have been added during polymerization through a functionalized monomer, and in particular, a functionalized propylene oxide monomer. Similarly, as used herein, the term "functional end group" refers to an functional group located a terminal end of a polymer chain. The term "functionalized initiating alcohol" is used herein to refer to an alcohol capable of initiating ring opening copolymerization of a maleic anhydride monomer and a functionalized or unfunctionalized polypropylene oxide monomer, in the presence of a magnesium catalyst.

As used herein, the terms "bioactive molecule(s)" and "bioactive material(s) are used interchangeably to refer to substances that influence cellular function. Bioactive molecules may include, without limitation, peptides, carbohydrates, proteins, oligonucleotides and small molecule drugs.

The term isomerization is used herein to refer to a reaction that converts the cis-isomer (PPM) to the trans-isomer (PPF) form in the presence of a catalyst.

The bioactive or other functional species that may be attached to the functional groups on the PPF polymers of the present invention is not particularly limited, provided that they contain or are functionalized to contain a moiety capable of bonding to at least one of the functional groups on the polymer. As used herein, the terms "bioactive molecule(s)" and "bioactive material(s) are used interchangeably to refer to substances that influence cellular function and may include, without limitation, peptides, carbohydrates, proteins, oligonucleotides and small molecule drugs. As used in the context of substances that may be attached to the functionalized PPF polymers of the present invention, the term "functional species" refers to substances other than bioactive materials that may be added to the functionalized PPF polymers of the present invention to provide an added benefit and may include such things as fluorescent and other markers, small molecule dyes, and/or halide atoms. While the bioactive or other functional species to be attached is not limited as to size, they are generally smaller, less than about 40,000 Da and should not be so large that they cannot easily reach the inner surfaces of the printed or formed polymer structure and/or reach the functional groups on the PPF polymers in such a way as to make bonding possible. In various embodiments, the bioactive or other functional species to be attached may include, without limitation, short-chain peptides, peptides, proteins, sugars, carbohydrates, bioactive drugs, oligonucleotides, small molecule drugs, fluorescent or other markers, small molecule dyes and/or halide atoms.

While not necessary to practice the present invention, the functional groups on the PPF polymers of the present invention are preferably functional groups capable of entering into well known "click" reactions to facilitate post polymerization addition of desirable materials, such as bioactive compounds, to the polymer. As used herein, the terms "click reaction," "click chemistry," "click chemistry methods," and "click chemistry reactions," are used interchangeably to refer to a group of orthogonal conjugation reactions, generally referred to in the art as "click" reactions, that fulfill the following prerequisites: (i) high yield, nearly quantitative conversion; (ii) biologically benign conditions (aqueous solution, ambient temperature, and near physiologic pH); (iii) limited or no residual byproduct. These reactions are typically simple to perform, high yielding, stereospecific, wide in scope, create only byproducts that can be removed without chromatography, and can be conducted in easily removable or benign solvents. Similarly, the term "clickable" refers to a molecule or functional group capable of bonding via a click reaction.

As set forth above, the "click" chemistry concept currently represents a number of orthogonal reactions, which are robust, selective, efficient, and high yielding. In various embodiments, suitable click reactions may include, without limitation, copper (I) catalyzed azide-alkyne cycloaddition (CuAAC) reactions (a.k.a. Huisgen cycloaddition reactions), thiol-ene radical addition reactions, oxime ligation reactions, Michael-addition reactions, thiol-Michael-addition reactions, Mannich-type addition reactions, "ene-type" addition reactions, thiol-ene radical addition, strain promoted azide-alkyne cycloaddition (SPAAC) reactions, non-traceless Staudinger ligation, traceless Staudinger ligation, Diels-Alder reactions, hetero Diels-Alder reactions, inverse electron demand Diels-Alder reactions, tandem [3+2] cycloaddition-retro-Diels-Alder (tandem crD-A) reactions, thiol-alkyne reactions, thiol-pyridyl disulfide reactions, thiol-halogen ligation, native chemical ligation, and thiazolidine ligation reactions. In one or more embodiments, suitable "clickable" moieties may include, without limitation, alkyne groups, alkene groups, azide groups, ketones or strained cyclooctyne groups. On one or more embodiments, a bioactive or other functional species may be attached to the functional groups on the PPF polymers of the present invention by means of a thiol-ene reaction, thiol-yne reaction, 1,3-dipolar cycloaddition between alkyne and azide, or oxime ligation between ketone and amine type reaction between a functional moiety on the bioactive or other functional species and a functional group on the functionalized PPF polymers of the present invention.

End-Functionalized PPF Polymers

In a first aspect, the present invention is directed to an end functionalized poly(propylene fumarate) polymer that is non-toxic, has constrained and predictable material properties suitable for 3D printing using reactive initiators, and can be derivatized with bioactive groups after it has been printed or otherwise formed into a polymer structure. As set forth above, in some embodiments the PPF polymers of the present invention contain a functional end group useful for post polymerization reactions to add functional species to the polymer, which is introduced into these PPF polymers through the initiating alcohol used to form the PPM intermediate in the first step outlined above. The terms "initiation alcohol" and "initiating alcohol" are used interchangeably to refer to a molecule that comprises a hydroxyl group, which initiates the ring open polymerization reaction of maleic anhydride and propylene oxide in the presence of a Mg catalyst, bound directly or indirectly to a functional end group. Some or all of these functional end groups survive both the polymerization (step 1) and isomerization reactions (step 2) that form the PPF polymers of the present invention and are useful for post polymerization addition of one or more functional species, such as bioactive materials, markers, small molecule dyes, short-chain peptides, drugs, and/or halide atoms. As used herein, the term "isomerization" refers broadly to the conversion of the cis-isomer (PPM) to its trans-isomer (PPF) form or, in the context of a chemical reaction or process (an "isomerization reaction") to a reaction or process that converts the cis-isomer (PPM) to its trans-isomer (PPF) form.

The functional end groups that may be used are not particularly limited, provided that they maintain at least some of their reactivity after the polymerization and isomerization reactions. In one or more embodiments, the functional groups on the end functionalized PPF polymers of the present invention may include without limitation, benzyl groups, alkyne groups, propargyl groups, allyl groups, alkene groups, 4-dibenzyocyclooctyne groups, cyclooctyne groups, ketone groups, aldehyde groups, tertiary halogen groups and poly(ethylene glycol) groups, lactone groups, protected hydroxyl groups, or a combination thereof. As used herein, the term "protected hydroxyl group" refers to a hydroxyl group wherein the hydrogen atom has been replaced with a protecting group to prevent unwanted reactions until a desired reaction can take place, at which time the protection group is replaced with a proton to reform the hydroxyl group. Any suitable protecting group or groups known in the art may be used, including, without limitation, tert-butyloxycarbonyl (BOC) groups, trimethylsilyl ether (TMS) group, tert-butyldimethylsilyl ethers (TBDMS), or fluorenylmethyloxycarbonyl (FMOC) groups.

In one or more embodiments, the PPF polymer of the present invention may have more than one different end function group. In some embodiments, this may be accomplished by using initiating alcohols having more than one type of functional group. This approach, however, will often result in a polymer mixture having a broader polydispersity and less control over the properties of the polymer than is the case when a single functionalized initiating alcohol is used. Accordingly, production of the PPF polymer of the present invention having more than one different end function group is preferably accomplished by making two or more separate batches of polymer, each having a different desired end functional group and then combing them into a homogenous mixture to form the PPF polymer of the present invention may have more than one different end function group.

In various embodiments, the end functionalized PPF polymers of the present invention will have a number average molecular weight ($M_n$), as measured by size exclusion chromatography (SEC), of from about 0.7 kDa to about 100,000 kDa and a polydispersity index ($Ð_M$) of from about 1.01 to about 1.8. In some embodiments, the end functionalized PPF polymer will have a $M_n$ of 1.0 kDa or more, in other embodiments, about 5 kDa or more, in other embodiments, about 8 kDa or more, in other embodiments, about 10 kDa or more, in other embodiments, about 1000 kDa or more, and in other embodiments, about 10,000 kDa or more. In some embodiments, the end functionalized PPF polymer will have a $M_n$ of 90,000 kDa or less, in other embodiments, about 80,000 kDa or less, in other embodiments, about 70,000 kDa or less, in other embodiments, about 60,000 kDa or less, in other embodiments, about 50,000 kDa or less, and in other embodiments, about 40,000 kDa or less.

In some embodiments, the end functionalized PPF polymer will have polydispersity index ($Đ_M$) of 1.03 or more, in other embodiments, about 1.05 or more, in other embodiments, about 1.10 or more, in other embodiments, about 1.20 or more, in other embodiments, about 1.30 or more, in other embodiments, about 1.40 or more. In some embodiments, the end functionalized PPF polymer will have a $Đ_M$ of 1.70 or less, in other embodiments, about 1.60 or less, in other embodiments, about 1.50 or less, in other embodiments, about 1.40 or less, in other embodiments, about 1.30 or less, and in other embodiments, about 1.20 or less.

In various embodiments, the end functionalized poly(propylene fumarate) polymers of the present invention may having the formula:

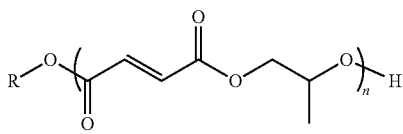

wherein n is an integer from 1 to 1000, and R is a functional group useful for post polymerization addition of desirable materials, such as bioactive compounds, to the polymer. In some of these embodiments, n is an integer from 100 to 1000, in other embodiments, from 200 to 1000, in other embodiments, from 300 to 1000, in other embodiments, from 400 to 1000, in other embodiments, from 1 to 900, in other embodiments, from 1 to 800, in other embodiments, from 1 to 700, and in other embodiments, from 1 to 600. In various embodiments, R may include, without limitation, benzyl groups, alkyne groups, propargyl groups, allyl groups, alkene groups, 4-dibenzyocyclooctyne groups, cyclooctyne groups, ketone groups, aldehyde groups, tertiary halogen groups and poly(ethylene glycol) groups, and combinations thereof. In some of these embodiments, R may include a clickable moiety, as defined above.

In some embodiments, the poly(propylene fumarate) polymer of the present invention may having the formula:

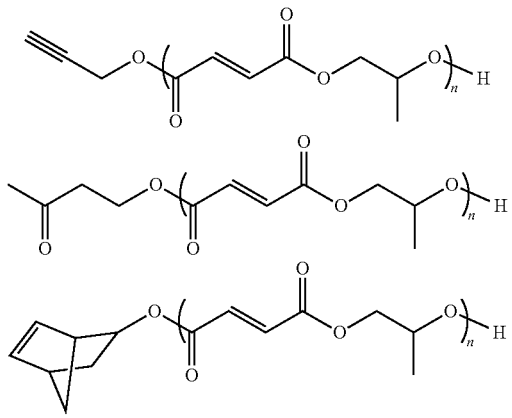

wherein n is defined as above.

As set forth above, the end functional groups of the PPFs of the present invention may be used for the post polymerization addition of functional species, such as bioactive or other useful materials, to the polymer. In one or more of these embodiments, the functional species to be attached to the PPF polymer of the present invention will naturally contain a functional group that is can bond to the end functional groups of the PPF by a click or other type of reaction without losing its desired functionality. In some other embodiments, however, the functional species to be attached to the PPF polymer of the present invention must first be functionalized with a moiety known to bond the end functional group used, preferably via a click reaction. The particular clickable moiety chosen and means for its attachment to the functional species will, of course, depend upon the bioactive or other material to be attached and the specific click reaction to be used. One of ordinary skill in the art will be able to attach the appropriate clickable moiety to the bioactive or other material to be attached without undue experimentation. For example, a peptide functionalized with an azide group could be coupled to a alkyne end-functionalized PPF chains on a scaffold using a Huisgen 1,3 cycloaddition reaction. For example, a peptide functionalized with an thiol group or cysteine residue could be coupled to a alkene or norbornene end-functionalized PPF chains on a scaffold using a thiolene reaction.

It has been found that the addition of end functional groups on the PPF polymers of the present invention to not significantly affect the desired mechanical, thermal, degradation, and/or toxicity properties of the polymers at the molecular weights disclosed and discussed herein.

Monomer-Functionalized PPF Polymers

In a second aspect, the present invention is directed to novel functionalized PPF polymers comprising the isomerized residue of the maleic anhydride monomer and the residue of functionalized propylene oxide monomer used to form the polymer. As will be apparent, when the maleic anhydride monomer and the residue of functionalized propylene oxide monomer react to form the polymer, the maleic anhydride monomer and propylene oxide will form the backbone of the PPM/PPF polymer, with the functional group of the functionalized propylene oxide monomer forming an active side chain.

As used herein, the term "residue(s)" is used to refer generally to the part of a monomer or other chemical unit that has been incorporated into a polymer or large molecule. By extension, the terms "residue of the maleic anhydride monomer" and the "residue of functionalized propylene oxide monomer" are used to refer to the parts of the maleic anhydride monomer and functionalized propylene oxide monomer, respectively, that has been incorporated into the PPM and PPF polymers. The term "isomerized residue of a maleic anhydride monomer" specifically refers to the residue of the maleic anhydride monomer wherein the double bond has been isomerized from the cis configuration to the trans configuration with the formation of the functionalized PPF polymer. The terms "residue of the initiating alcohol" or "initiating alcohol residue" and the like, refer to the parts of the initiating alcohol that remain bound at the end of the PPM/PPF polymer chain after it initiates polymerization. Similarly, the terms "residue of the functionalized initiating alcohol" or "functionalized initiating alcohol residue" and the like, refer to the functional group and other parts of the functionalized initiating alcohol that remain bound at the end of the polymer chain after the functionalized initiating alcohol initiates polymerization.

In various embodiments, the functional group on the residue of the functionalized propylene oxide monomer may include, without limitation, an alkyne group, a propargyl group, an alkene group, a hydroxyl group, a ketone group, a thiol group, a halide group, a nitrobenzyl group, or a group that can easily be converted into a functional group such as a halide group, a nitrobenzyl group, or hydroxyl group. It has been found that using the monomer functionalization method increases the quantity of available functional groups compared to only end-group functionalization, even with less functional groups surviving processing. It has also been found that the monomer of the PPF polymers of the present invention to not significantly affect the desired mechanical, thermal, degradation, and/or toxicity properties of the polymers, at least at the molecular weights disclosed and described herein.

In various embodiments, the functionalized propylene oxide monomers residues of the novel functionalized PPF polymers of the present invention will comprise functional groups capable of entering into "click" reactions with a bioactive compound having or functionalized to have the corresponding functional group for the click reaction. For example, in one or more of these embodiments, the functional group on the functionalized propylene oxide may be an alkyne group, an alkene group, a hydroxyl group, a ketone group, a thiol group, or a group that can easily be converted into such a functional group. In some embodiments, the functionalized propylene oxide may be (±)-epichlorohydrin. In one or more embodiments, the functionalized propylene oxide may be an alkyne functionalized propylene oxide. In some embodiments, the novel functionalized PPF polymers of the present invention comprises the residue of glycidyl propargyl ether.

In some of these embodiments, the novel functionalized PPF polymers of the present invention comprises the residue of 2-[[(2-nitrophenyl)methoxy]methyl]oxirane (NMMO). It should be appreciated that in these embodiments, the nitrobenzyl group on NMMO is a UV sensitive protecting group, which can easily be replaced with a hydroxyl group upon exposure to specific UV wavelengths. In some other embodiments, the novel functionalized PPF polymers of the present invention comprise the residue of a halide functionalized propylene oxide. In some of these embodiments, the novel functionalized PPF polymers of the present invention comprises the residue of (±)-epichlorohydrin. It should be appreciated that in these embodiments, the halide group on (±)-epichlorohydrin is a protecting group, which is later replaced with any suitable nucleophile. Suitable nucleophiles may include without limitation, amines, alcohols, thiols and hydroxylamines.

As should also be apparent, in various embodiments, the functionalized PPF polymers of the present invention may also contain an end functional group added through the initiating alcohol as described above. Accordingly, in one or more embodiments, the functionalized PPF polymers of the present invention may have the formula:

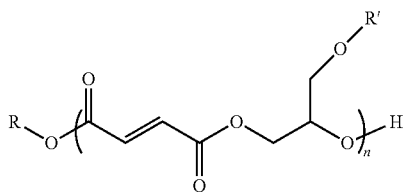

where n is an integer from 1 to 100; R is a functional group comprising a group selected from alkyne groups, propargyl groups, allyl groups, alkene groups, 4-dibenzyocyclooctyne groups, cyclooctyne groups, ketone groups, aldehyde groups, tertiary halogen groups and poly(ethylene glycol) groups, lactone groups, and non-functional initiating alcohol residues; and R' is a functional group, or an alkyl or aryl group having a functional group, that is capable of entering into a click or other reaction with a corresponding functional group and may comprise an alkyne group, an alkene group, a hydroxyl group, a protected hydroxyl group, thiol group, halide group, or hydroxyl group, among others. As set forth above, the term "protected hydroxyl group" refers to a hydroxyl group wherein the hydrogen atom has been replaced with a protecting group to prevent unwanted reactions until a desired reaction can take place, at which time the protection group is replaced with a proton to reform the hydroxyl group. Any suitable protecting group or groups known in the art may be used, including, without limitation, tert-butyloxycarbonyl (BOC) groups, trimethylsilyl ether (TMS) group, tert-butyldimethylsilyl ethers (TBDMS), or fluorenylmethyloxycarbonyl (FMOC) groups. In some of these embodiments, n may be an integer from about 5 to about 100, in other embodiments, from 15 to 100, in other embodiments, from 25 to 100, in other embodiments, from 40 to 100, in other embodiments, from 1 to 80, in other embodiments, from 1 to 70, in other embodiments, from 1 to 60, and in other embodiments, from 1 to 40.

In some embodiments, the functionalized PPF polymer of the present invention may have the formula:

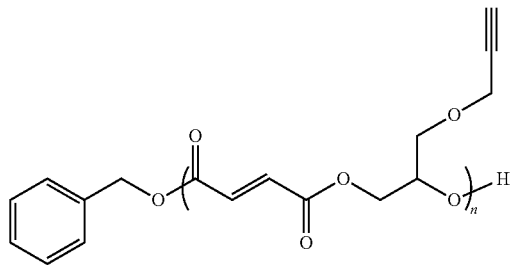

where n is an integer from about 1 to about 100. In some of these embodiments, n may be an integer from about 5 to about 100, in other embodiments, from 15 to 100, in other embodiments, from 25 to 100, in other embodiments, from 40 to 100, in other embodiments, from 1 to 80, in other embodiments, from 1 to 70, in other embodiments, from 1 to 60, and in other embodiments, from 1 to 40.

In some other embodiments, the functionalized poly(propylene fumarate) polymer of the present invention may have the formula:

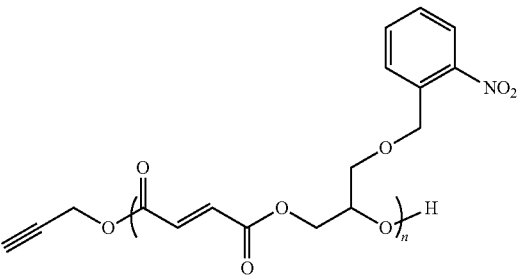

where n is an inter from about 1 to about 100. In some of these embodiments, n may be an integer from about 5 to about 100, in other embodiments, from 15 to 100, in other embodiments, from 25 to 100, in other embodiments, from 40 to 100, in other embodiments, from 1 to 80, in other embodiments, from 1 to 70, in other embodiments, from 1 to 60, and in other embodiments, from 1 to 40.

In some other embodiments, the functionalized poly(propylene fumarate) polymer of the present invention may have the formula:

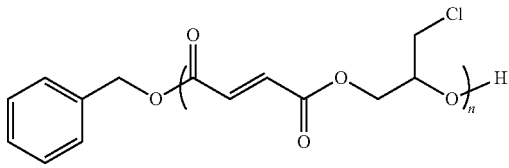

where n is an inter from about 1 to about 100. In some of these embodiments, n may be an integer from about 5 to about 100, in other embodiments, from 15 to 100, in other embodiments, from 25 to 100, in other embodiments, from 40 to 100, in other embodiments, from 1 to 80, in other embodiments, from 1 to 70, in other embodiments, from 1 to 60, and in other embodiments, from 1 to 40.

In various embodiments, the monomer functionalized PPF polymers of the present invention will have a number average molecular weight ($M_n$), as measured by size exclusion chromatography (SEC), of from about 0.7 kDa to about 100,000 kDa and a polydispersity index ($Ð_M$) of from about 1.01 to about 1.8. In some embodiments, the monomer functionalized PPF polymer will have a $M_n$ of 1.0 kDa or more, in other embodiments, about 5 kDa or more, in other embodiments, about 8 kDa or more, in other embodiments, about 10 kDa or more, in other embodiments, about 1000 kDa or more, and in other embodiments, about 10,000 kDa or more. In some embodiments, the monomer functionalized PPF polymer will have a $M_n$ of 90,000 kDa or less, in other embodiments, about 80,000 kDa or less, in other embodiments, about 70,000 kDa or less, in other embodiments, about 60,000 kDa or less, in other embodiments, about 50,000 kDa or less, and in other embodiments, about 40,000 kDa or less.

In some embodiments, the monomer functionalized PPF polymer will have polydispersity index ($Ð_M$) of 1.03 or more, in other embodiments, about 1.05 or more, in other embodiments, about 1.10 or more, in other embodiments, about 1.20 or more, in other embodiments, about 1.30 or more, in other embodiments, about 1.40 or more. In some embodiments, the monomer functionalized PPF polymer will have a $Ð_M$ of 1.70 or less, in other embodiments, about 1.60 or less, in other embodiments, about 1.50 or less, in other embodiments, about 1.40 or less, in other embodiments, about 1.30 or less, and in other embodiments, about 1.20 or less.

Functionalized Propylene Oxide Monomers

In a third aspect, the present invention is directed to novel functionalized comonomers used to form the novel functionalized PPF polymers discussed above. In various embodiments, the functionalized monomer for forming the functionalized poly(propylene fumarate) polymer of the present invention comprises a glycidyl group connected through an ether bond to an alkyl or aryl group having a functional group capable of entering into a click reaction with a corresponding functional group. In some of these embodiments, the alkyl or aryl groups will comprise an alkyne group, an alkene group, a hydroxyl group, a protected hydroxyl group, thiol group, or halide group. In some other embodiments, the functional group may be connected directly to the glycidyl group.

In some embodiments, the novel functionalized comonomers of the present invention may have the formula:

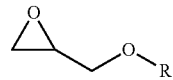

wherein R is a functional group, or an alkyl or aryl group containing a functional group, that is capable of entering into a "click" or other reaction with a corresponding functional group on a bioactive compound (i.e. bioactive drugs, peptides, proteins, sugars, etc., as described above), functional species, or other compound to be added to the PPF polymer. In some embodiments, the targeted bioactive compound may be functionalized to add the corresponding functional group provided that doing so does not denature the bioactive compound or otherwise render the bioactive compound, functional species, or other compound to be added to the PPF polymer ineffective for its intended purpose. In one or more embodiments, R will be an alkyl or aryl group containing alkyne, alkene, hydroxyl, protected hydroxyl, thiol or halide functional group.

In one or more embodiments, the functionalized monomer of the present invention is glycidyl propargyl ether. In some embodiments, the functionalized monomer of the present invention may have the formula:

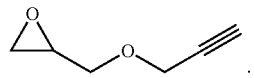

In one or more other embodiments, the functionalized monomer of the present invention is 2-[[(2-nitrophenyl)methoxy]methyl]oxirane (NMMO). In some embodiments, the functionalized monomer of the present invention may have the formula:

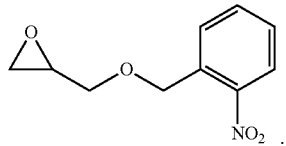 [SMILES: O=[N+]([O-])c1ccccc1COCC1CO1 ; "."]

In some other embodiments, the functionalized propylene oxide may be (±)-epichlorohydrin. In some embodiments, the functionalized monomer of the present invention may have the formula:

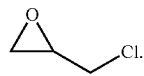

Functionalized PPF Polymer with Attachments

In a another aspect, the present invention is directed to a functionalized PPF polymer, as described above, further comprising one or more bioactive or other functional species attached to the functional groups on the PPF polymers, as described above. In one or more embodiment, the present invention may include a short chain peptide, dye or other bioactive compound or functional species attached to the functionalized PPF polymers of the present invention as shown in Scheme 3, below and/or as described in Examples 13 and 14 below. In some of these embodiments, an azide functionalized dye, bioactive compound or other functional species is dissolved in a suitable solvent, such as an isopropyl alcohol/$H_2O$ mixture, combined with a $CuSO_4$ catalyst and sodium ascorbate, and allowed to react with an end or monomer functionalized PPF polymer having an alkyne functional groups for about 1 hour. In these embodiments, the functionalized dye, bioactive compound or other functional species is added to the end or monomer functionalized PPF polymer through a copper assisted 1,3 Huisgen cycloaddition click reaction. The end or monomer functionalized PPF polymer with the attached dye, bioactive compound or other functional species is then washed with isopropyl alcohol and $H_2O$ to remove any non-tethered dye, bioactive compound or other functional species and catalyst.

In some other embodiments, an azide functionalized peptide may be was synthesized as follows. First, a desired he peptide may be synthesized by microwave-assisted solid phase peptide synthesis (SPSS) on a CEM Liberty1 peptide synthesizer using standard Fmoc chemistry conditions and a Wang resin. The peptide (still on the Wang resin) is then combined with bromohexanoic acid (1 mmol), diisopropylcarbodiimide (DIC) and hydroxybenzotriazole and allowed to react for about 2 hours to produce a Br-functionalized peptide, which is then cleaved from the using convention methods. The solid Br-functionalized peptide is then purified and then redissolved in a 10% ethanol solution in water. Addition of the azide functional group was performed by adding $NaN_3$ and 18-Crown-6 and allowing the solution to react for about 12 h to yield the azide functionalize peptide.

Functionalized PPF Scaffolds or other Polymer Structures

In a yet another aspect, the present invention is directed to a 3D printed scaffold or other structure comprising the functionalized PPF polymer as described above. In one or more of these embodiments, the functionalized PPF polymers of the present invention are formed into a 3-D printable resin. In some of these embodiments, the 3-D printable resin will have the composition reported in Luo, Y.; Dolder, C. K.; Walker, J. M.; Mishra, R.; Dean, D.; Becker, M. L., *Biomacromolecules*, 2016, 17, 690-697, the disclosure of which is incorporated herein in its entirety. In these embodiments, the end or monomer functionalized PPF is dissolved into an equal mass of diethyl fumarate (DEF) and a mixture of photoinitiators and light scattering agents are mixed evenly throughout the resin. The resin is then 3-D printed and photo-crosslinked with a cDLP printer or other suitable 3-D printer to form a scaffold or other polymer structure having available functional groups for the addition of bioactive compounds or other functional species.

In a yet another aspect, the present invention is directed to a 3D printed scaffold or other polymer structure comprising a functionalized PPF polymer as described above and a plurality of bioactive or other functional species, wherein a plurality of bioactive or other functional species have been attached to the available functional groups on the PPF polymers after formation scaffold or other structure.

Methods of Making End-Functionalized PPF Polymer

In as second aspect, the present invention is also direct to a the method for forming the end functionalized PPF polymers described above. The method is fairly straightforward. First, an initiating alcohol, a magnesium catalyst, preferably $Mg(BHT)_2(THF)_2$ or $Mg(OEt)_2$, maleic anhydride, and propylene oxide are placed in an ampule or other suitable sealed, dry vessel and dissolved with a suitable solvent, such as toluene or hexane, to a monomer (maleic anhydride and propylene oxide) concentration of from about 0.5 M to about 5 M. As will be apparent, it is important that the reaction takes place in a sealed, dry environment to avoid undesirable side reactions. In some embodiments, the reagents are all added under an inert atmosphere and preferably under a $N_2$ blanket.

As set forth above, in one or more of these embodiments of the present invention, the functionalized initiating alcohols and will comprise a hydroxyl group, which initiates the ring open polymerization reaction of the maleic anhydride and propylene oxide monomers, and a functional end group, which is useful for post polymerization reactions and survives both the polymerization (step 1) and isomerization reactions (step 2). Suitable functionalized initiating alcohols may include, without limitation, propargyl alcohol, allyl alcohol, 4-dibenzyocyclooctynol, 4-hydroxybutan-2-one, 3-hydroxypropan-2-one, 5-hydroxypentan-2-one, 6-hydroxyhexan-2-one, 7-hydroxyheptan-2-one, 8-hydroxyoctan-2-one, 5-norbornen-2-ol, PEG diol, α-bromoisobtyryl 4-methanol benzylmethanoate, linear polymers having a hydroxyl end group, or a combination thereof.

The catalyst for the ROP polymerization of maleic anhydride and propylene oxide may be an organometallic catalyst, and is preferably a magnesium catalyst. Suitable magnesium catalysts may include $Mg(BHT)_2(THF)_2$ and $Mg(OEt)_2$. In one or more embodiments, the catalyst is $Mg(BHT)_2(THF)_2$. Suitable solvents for this reaction is generally a non-polar alkyl carbon chain and may include, without limitation, pentane, hexane, mixed hexanes, heptane, octane, nonane, decane dodecane, toluene, dioxane, or combinations thereof. In some embodiments, the solvent is toluene. In some other embodiments, the solvent is hexane or mixed hexanes.

As set forth above, the monomer (maleic anhydride and (functionalized and/or unfunctionalized) propylene oxide) concentration in the solution will be from about 0.5 M to about 5 M. As will be appreciated by those of skill in the art, a higher monomer concentration will result in a faster conversion of the monomers and requires less solvent. In some embodiments, monomer concentration in the solution will be from about 0.5 M to about 4 M, in other embodiments, from about 0.5 M to about 3 M, in other embodiments, from about 0.5 M to about 2 M, in other embodiments, from about 1 M to about 5 M, in other embodiments, from about 1.5 M to about 5 M, in other embodiments, from about 2 M to about 5 M, and in other embodiments, from about 2.5 M to about 5 M.

In these embodiments, the molar ratio of the initiating alcohol to the magnesium catalyst is about from about 1:1 to about 1:1000 and the molar ratio of the initiating alcohol to the monomers is from about 1:5 to about 1:1000. In some embodiments, the molar ratio of the initiating alcohol to the magnesium catalyst is from about 1:1 to 1:500, in other embodiments, from 1:1 to 1:300, in other embodiments, from 1:1 to 1:200, in other embodiments, from 1:1 to 1:100, in other embodiments, from 1:1 to 1:75, in other embodiments, from 1:1 to about 1:50, in other embodiments, from about 1:5 to about 1:20, in other embodiments, from about 1:5 to about 1:25, in other embodiments, from about 1:1 to about 1:15, in other embodiments, from 1:10 to 1:1000, in other embodiments, from 1:50 to 1:1000, in other embodiments, from 1:100 to 1:1000, and in other embodiments, from 1:200 to 1:1000. In some embodiments, the molar ratio of the initiating alcohol to the monomers is anywhere from about 1:5 to about 1:500, in other embodiments, from about 1:5 to about 1:300, in other embodiments, from 1:5 to about 1:250, in other embodiments, from about 1:5 to about 1:150, in other embodiments, from about 1:5 to about 1:50, in other embodiments, from about 1:5 to about 1:10, in other embodiments, from about 1:25 to about 1:1000, in other embodiments, from about 1:100 to about 1:1000, in other embodiments, from about 1:200 to about 1:1000.

As will be apparent to those of skill in the art, the maleic anhydride and propylene oxide should be present in the solution in about a 1:1 molar ratio to prevent wasting monomer. It should be appreciated that neither maleic anhydride or propylene oxide will homopolymerize under these reaction conditions.

The ampule or other vessel is then sealed and the solution heated to a temperature of from about 40° C. to about 100° C. for from about 1 h to about 96 h to begin and/or maintain a ring opening polymerization reaction between the maleic anhydride and propylene oxide, initiated by the initiating alcohol and catalyzed by the magnesium catalyst, to form an end functionalized PPM polymer intermediate. In some embodiments, the solution heated to a temperature of from about 40° C. to about 90° C., in other embodiments, from about 40° C. to about 70° C., in other embodiments, from about 40° C. to about 50° C., in other embodiments, from about 45° C. to about 100° C., in other embodiments, from about 60° C. to about 100° C., and in other embodiments, from about 70° C. to about 100° C. to form the end functionalized PPM polymer intermediate.

In some embodiments, the solution is heated for from about 1 h to about 6 h, in other embodiments, from about 1 h to about 12 h, in other embodiments, from about 1 h to about 24 h, in other embodiments, from about 1 h to about 48 h, in other embodiments, from about 1 h to about 72 h, and in other embodiments, from about 1 h to about 96 h to produce the PPM intermediate. (See FIGS. 1-3)

In some embodiments, the maleic anhydride, propylene oxide, initiating alcohol and $Mg(BHT)_2(THF)_2$ catalyst are all dissolved in toluene under a nitrogen blanket and then heated to a temperature of about 80° C. for from about 1 to about 30 hours to produce the PPM intermediate. In some of these embodiments, the reaction time will be from about 6 hours to about 24 hours, in other embodiments, from about 12 hours to about 24 hours, in other embodiments, from about 18 hours to about 24 hours, in other embodiments, from about 20 hours to about 24 hours, in other embodiments, from about 1 hours to about 24 hours, in other embodiments, from about 1 hours to about 20 hours, and in other embodiments, from about 1 hours to about 18 hours.

In some other embodiments, the maleic anhydride, propylene oxide, initiating alcohol and $Mg(BHT)_2(THF)_2$ catalyst are all dissolved in hexanes under a nitrogen blanket and then heated to a temperature of about 45° C. for from about 1 h to about 100 h hours to produce the PPM intermediate. In some of these embodiments, the reaction time will be from about 12 hours to about 96 hours, in other embodiments, from about 24 hours to about 96 hours, in other embodiments, from about 36 hours to about 96 hours, in other embodiments, from about 48 hours to about 96 hours, in other embodiments, from about 60 hours to about 96 hours, in other embodiments, from about 72 hours to about 96 hours, in other embodiments, from about 84 hours to about 96 hours, in other embodiments, from about 90 hours to about 100 hours, in other embodiments, from about 1 hours to about 90 hours, in other embodiments, from about 1 hours to about 80 hours, in other embodiments, from about 1 hours to about 70 hours. It has been found that while this system requires longer polymerization times as a consequence of reduced temperature, this method may be advantageous in terms of scale-up reactions. The solubility of all reagents other than the polymer into hexanes means the majority of impurities are removed from the polymer purely by decanting off the hexanes solution after polymerization, therefore reducing the number of precipitations required to recover pure PPM polymer intermediate. Advantageously, once the decanted solution is cooled to room temperature, the unreacted MAn recrystallizes and can be recovered for further use.

The PPM polymer intermediate may be collected and purified using any known method. One of ordinary skill in the art will be able to collect and purify the PPM polymer without undue experimentation using conventional techniques. In one or more embodiments, resultant PPM polymer intermediate may be recovered by repeated precipitation into an immiscible solvent, such as excess diethyl ether, hexane, hexanes, heptane, octane or chloroform.

In a second step, the PPM polymer intermediate is isomerized into its trans-isomer form (PPF) using any method known in the art for that purpose. In one or more embodiments, the PPM polymer may be isomerized using the methods described in U.S. Published Application No. 2016/0237212, the disclosure of which is incorporated herein by reference in its entirety. While the isomerization step does result in some other changes to the polymer, it should be apparent that most general aspects of the end functionalized PPF polymers of embodiments of the present invention, such as the approximate $M_n$, $Đ_M$, and $T_g$ ranges, are determined in the first reaction.

In one or more of these embodiments, the PPM polymer intermediate is then placed in a suitable container, such as a round bottom flask, and dissolved in a suitable solvent such as chloroform, tetrahydrofuran (THF), dioxane, diethyl ether, or a combination thereof, under an inert atmosphere. It is envisioned that whichever solvent is selected can be removed without undue difficulty or expense, and in some embodiments, the solvent is chloroform. Once the PPM polymer intermediate has been dissolved, a catalyst, preferably diethylamine, is added. The container is then connected to a condenser and then heated to a reaction temperature of from about 5° C. to about 80° C. In some embodiments, the reaction temperature may be from about 55° C. to about 65° C. In these embodiments, the solution is heated for from about 5 to about 100 hours. In some embodiments, the solution is heated for about 24 to about 48 hours.

It has been found that if even a relatively small amount of PPM polymer chains remain in the PPF polymer, it will adversely affect the ability of the polymer to cross link, rendering it unsuitable for 3D printing and other similar applications. Accordingly, it is important that essentially all of the PPM be converted to PPF or removed. (See FIG. 4) In some embodiments, the conversion rate of PPM to PPF is from about 96 mass percent to about 100 mass percent. In some embodiments, the conversion rate of PPM to PPF is from about 98 mass percent to about 100 mass percent. In some embodiments, the conversion rate of PPM to PPF is from about 99 mass percent to about 100 mass percent. In some embodiments, the PPF polymer of the present invention contains no residual PPM polymer chains as measured by Ultraviolet-Visible Spectroscopy (UV-Vis) spectra, Fourier Transform Infrared Spectroscopy (FTIR) spectra, proton Nuclear Magnetic Resonance (1H NMR) spectroscopy or Matrix Assisted Laser Desorption/Ionization—Time-of-Flight (MALDI-TOF) mass spectroscopy.

When the isomerization reaction is complete, the end functionalized PPF polymer may be isolated and purified by any suitable methods known in the art for that purpose. In one or more embodiments, and the end functionalized PPF polymer was recovered through precipitation from hexanes and the end functionalized PPF polymer was isolated and purified by washing with phosphate buffer solution (pH=6) in order to completely remove the diethylamine. The solvent may be removed by rotary evaporation or any other method known in the art for that purpose.

To further define and reduce embodiments of the present invention to practice, the ring-opening copolymerization of an equimolar mixture of maleic anhydride and propylene oxide using $Mg(BHT)_2(THF)_2$ as a catalyst with varying alcohol initiators and targeted DPs was investigated. The reaction conditions and yields for these experiments are shown in Table 1, below:

TABLE 1

Conditions and yield of PPF polymers produced using $Mg(BHT)_2(THF)_2$ as a catalyst with varying alcohol initiators and targeted DPs.

| Entry | Initiator (I) | DP | [MAn]:[PO]:[I]:[cat.] | Time (h) | MAn Conversion (%) | Yield (g) | Yield (%) |
|---|---|---|---|---|---|---|---|
| 1 | Benzyl alcohol | 10 | 10:10:1:1 | 18 | 75 | 7.8 | 89 |
| 2 | Benzyl alcohol | 25 | 25:25:1:1 | 24 | 85 | 7.6 | 86 |
| 3 | Benzyl alcohol | 50 | 50:50:1:1 | 48 | 81 | 7.1 | 81 |
| 4 | Benzyl alcohol | 100 | 100:100:1:1 | 72 | 85 | 6.9 | 78 |
| 5 | Propargyl alcohol | 10 | 10:10:1:1 | 18 | 97 | 4.1 | 92 |
| 6 | Propargyl alcohol | 25 | 25:25:1:1 | 24 | 96 | 3.8 | 85 |
| 7 | Propargyl alcohol | 50 | 50:50:1:1 | 48 | 91 | 3.5 | 77 |
| 8 | Propargyl alcohol | 100 | 100:100:1:1 | 72 | 93 | 3.5 | 76 |
| 9 | 4HB[a] | 10 | 10:10:1:1 | 18 | 89 | 6.6 | 92 |
| 10 | 4HB[a] | 25 | 25:25:1:1 | 24 | 90 | 6.8 | 95 |
| 11 | 4HB[a] | 50 | 50:50:1:1 | 48 | 86 | 6.0 | 83 |
| 12 | 4HB[a] | 100 | 100:100:1:1 | 72 | 89 | 5.8 | 80 |

[a] 4-Hydroxy-2-butanone.

Initially, benzyl alcohol (BnOH) was used as a primary alcohol initiator with the total concentration of reagents at 2 M in toluene. The reaction was conducted at 80° C. in a sealed, dry $N_2$ atmosphere (Scheme 2). The polymerization was allowed to continue for 24 h before quenching with excess chloroform, after which the polymer was recovered from precipitation in diethyl ether.

Scheme 2.
Ring-opening copolymerization of maleic anhydride and propylene oxide using various initiators to form poly(propylene maleate)

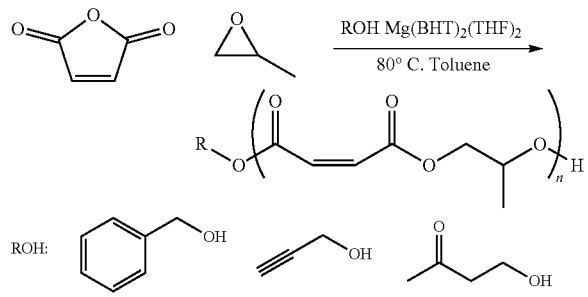

Figure 2:
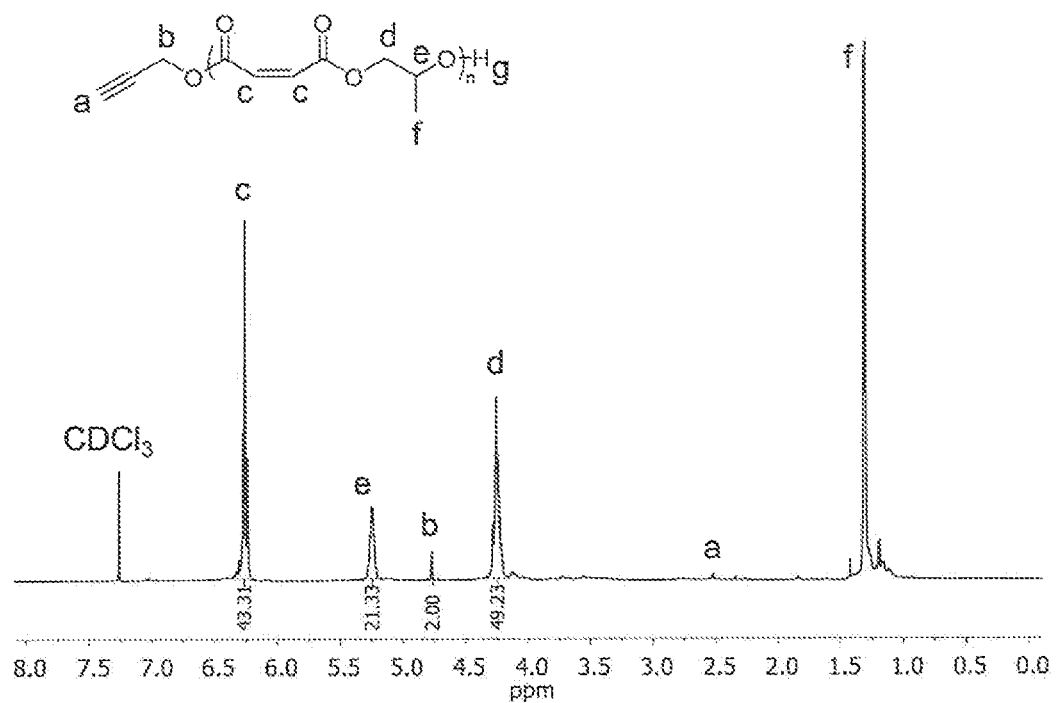
FIG. 2 is a $^1H$ NMR spectrum of DP 25 propargyl alcohol initiated poly(propylene maleate) (Table 2, Entry 6) using $Mg(BHT)_2(THF)_2$ as a catalyst (300 MHz, 303 K, DMSO-$d_6$).

The monomer conversion of MAn was monitored via $^1H$ NMR spectroscopic analysis of the crude reaction mixture and comparison of the monomer proton resonance (δ=7.01 ppm) to the corresponding polymer proton resonance (δ=6.26 ppm). The monomer conversion of PO was not characterized as a consequence of the low vapor pressure and boiling point of the PO leading to unreliable integrations using $^1H$ NMR spectroscopy. $^1H$ NMR spectroscopic analysis of the recovered material showed the polymer was poly(propylene maleate) with proton resonances corresponding to benzyl alcohol also present (FIG. 1). Notably, there were no proton resonances that would correspond to the methylene protons observed from the homopolymerization of PO (δ=3.3-3.5 ppm). While the homopolymerization of MAn has not been observed during copolymerization, the homopolymerization of PO has previously been observed as a consequence of the higher ring-strain leading to greater reactivity of the PO and low selectivity of the catalyst. The ratio of MAn and PO incorporated into the polymer backbone remained roughly equimolar and thus, few side reactions (such as branching or crosslinking at the alkene of incorporated MAn) are observed to have occurred.

Matrix assisted laser desorption/ionization time of flight mass spectrometry (MALDI-ToF MS) was used in order to confirm the chain end-group fidelity. As expected from an alternating copolymerization system, two major distributions were observed attributable to a full polymeric repeat unit or a half polymeric repeat unit (i.e. one extra maleic anhydride or propylene oxide incorporated on the chain-end). The end-groups for both major distributions were calculated to correspond to BnOH initiation, with no minor distributions observed. Hence, the copolymerization of MAn and PO using $Mg(BHT)_2(THF)_2$ as a catalyst will selectively initiate from a primary alcohol source. Previous copolymerizations using organocatalysts have resulted in unwanted side reactions including crosslinking at the alkene bond and the formation of unwanted hyperbranched copolymers. MALDI-ToF mass spectrum of the PPM also confirmed the lack of PO homopolymerization, with no consecutive mass differences attributable to PO addition adjacent to another PO repeat unit. The mechanism for the copolymerization of MAn and PO is likely to occur in a manner similar to the ROCOP of anhydrides and epoxides using dimetallic zinc catalysts, wherein the coordination insertion of maleic anhydride can only be initiated by an alcohol chain end and the coordination insertion of an epoxide can only be initiated by a carboxylic acid chain end, which leads to an alternating copolymerization.

Figure 5A:
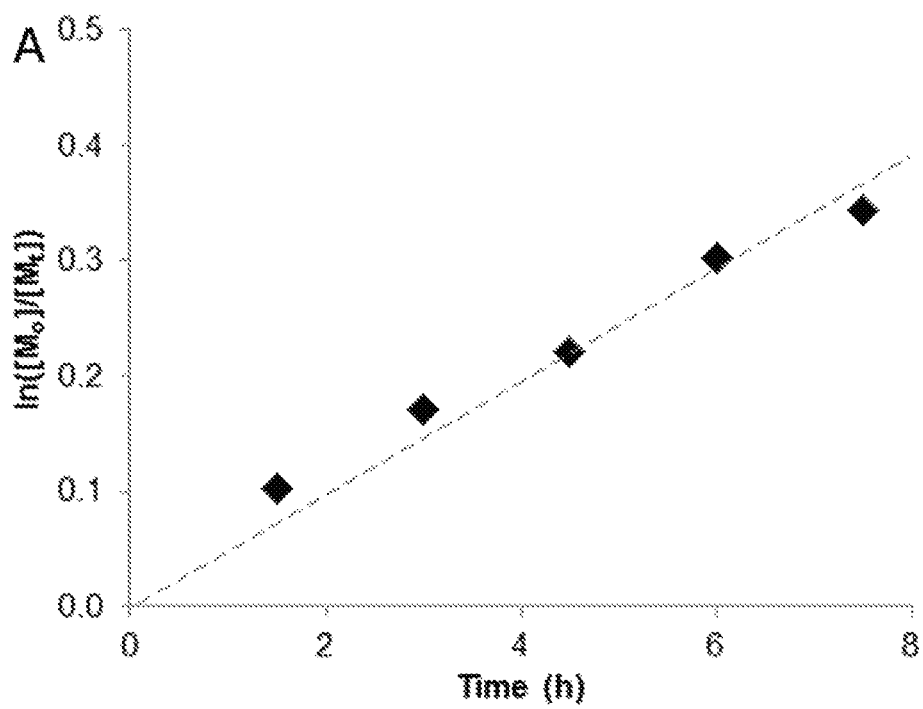
FIGS. 5A-B are a kinetic plot for the copolymerization of maleic anhydride and propylene oxide, conducted at 80° C. in toluene with $[MAn]_0:[PO]_0:[BnOH]_0:[Cat.]_0=25:25:1:1$, total initial monomer concentration=2 M (FIG. 5A) and a graph showing changes in $M_n$ (diamonds) and $Đ_M$ (squares) over increasing monomer conversion for the same copolymerization, determined by SEC against poly(styrene) standards (FIG. 5B).
Figure 5B:
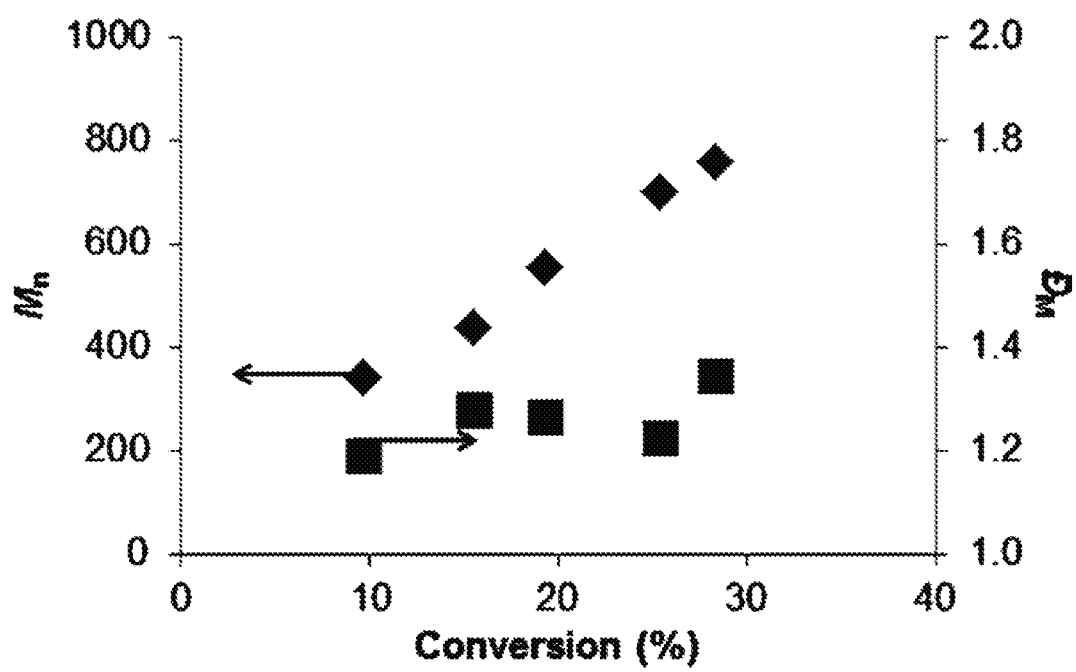

The pseudo-first order kinetics of the ROCOP of MAn and PO were followed under the same conditions, with a targeted degree of polymerization (DP) of 25 repeat units. Aliquots were withdrawn over a period of 8 h and the monomer conversion of MAn was determined by $^1H$ NMR spectroscopic analysis of the crude mixture. (FIG. 5A) The molecular mass distribution of each aliquot was determined by SEC after precipitation. (FIG. 5B) The monomer conversion of MAn was indicative of second order kinetics and the rate constant of propagation ($k'_p$) was observed to be $k'_p=1.36\times10^{-5}$ s$^{-1}$. As a consequence of the pseudo-first order kinetics, it can be assumed that the number of active chains is maintained and no termination side reactions occur throughout the polymerization. Linear molecular mass growth and low $Đ_M$ with increasing monomer conversion was also observed for each, providing further evidence of controlled ROCOP.

Figure 6:
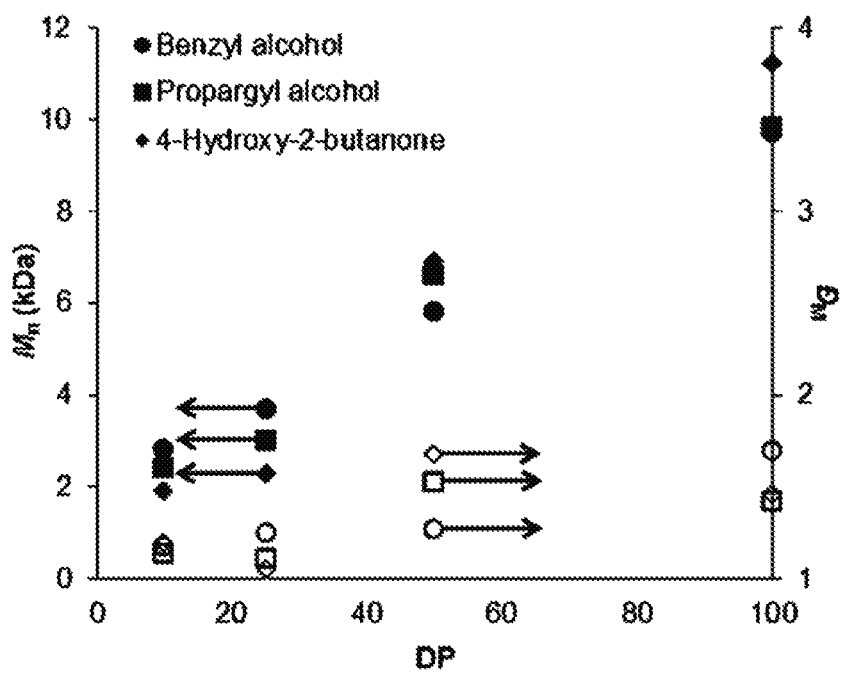
FIG. 6 is a graph showing $M_n$ (solid shapes) and $Đ_M$ (hollow shapes) for PPF at varying degrees of polymerization with a range of initiating species. Molecular masses were determined by SEC against poly standards using THF as an eluent.
Figure 7:
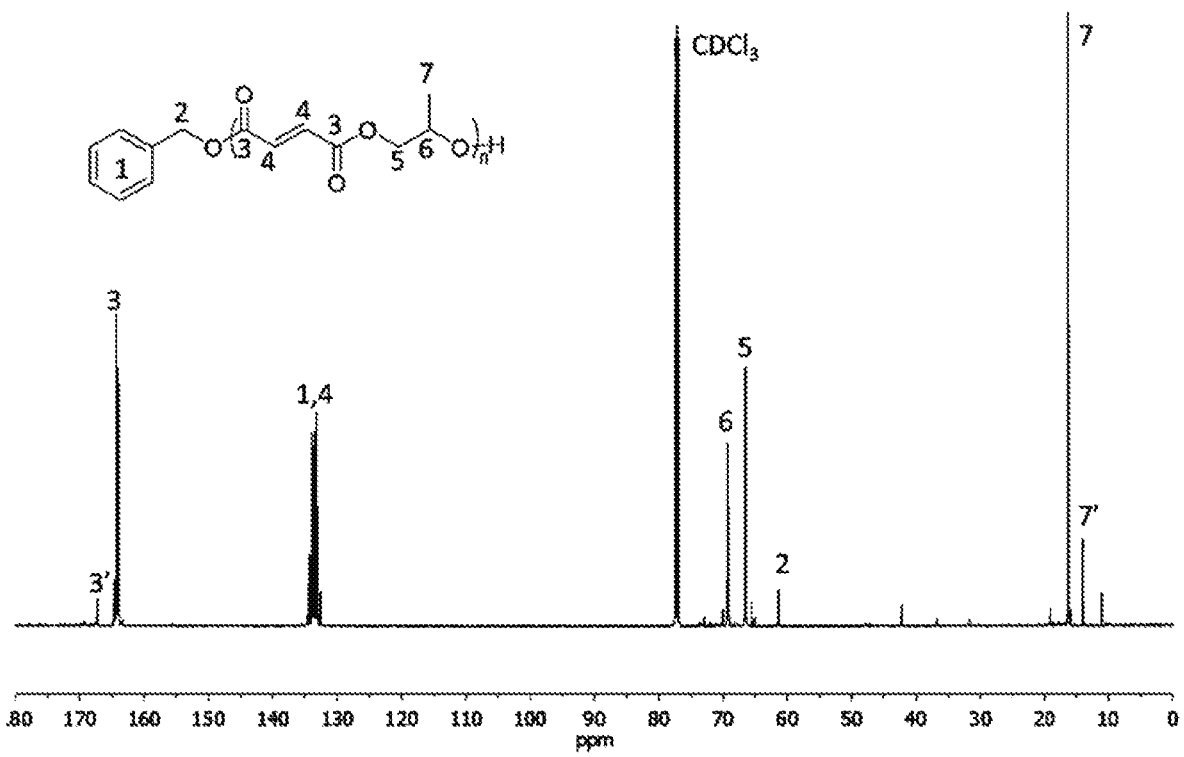
FIG. 7 is a $^{13}C$ NMR spectra for DP 10 benzyl alcohol initiated PPM (Table 2, Entry 1) (125 MHz, $CDCl_3$, 303 K).
Figure 8:
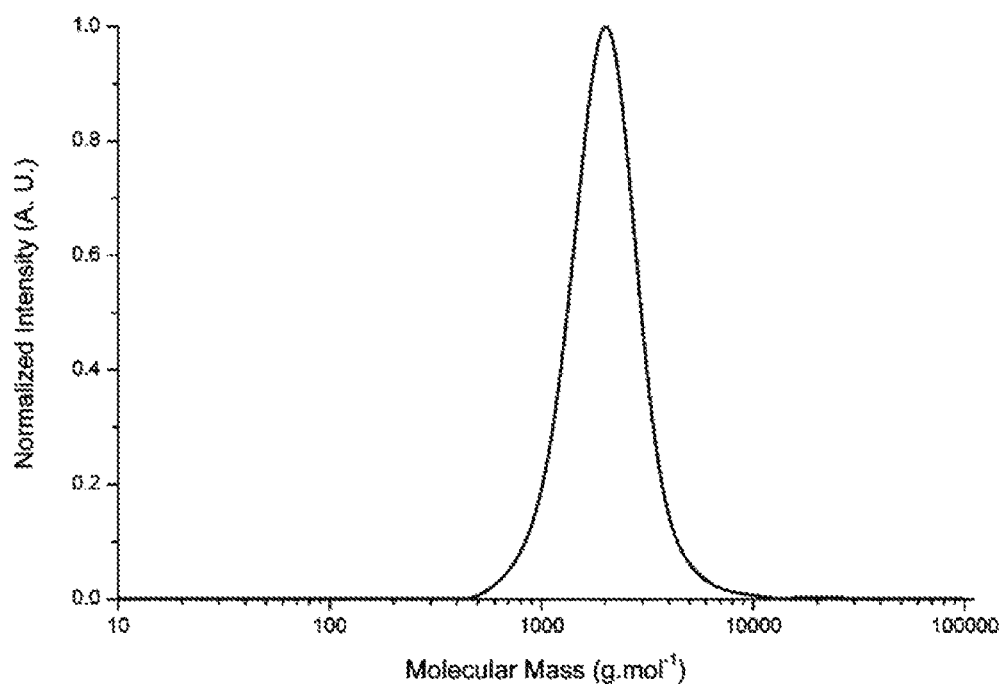
FIG. 8 is a SEC chromatogram for DP 25 benzyl alcohol initiated PPM (Table 2, Entry 2). The molecular mass determined against poly(styrene) standards.
Figure 9:
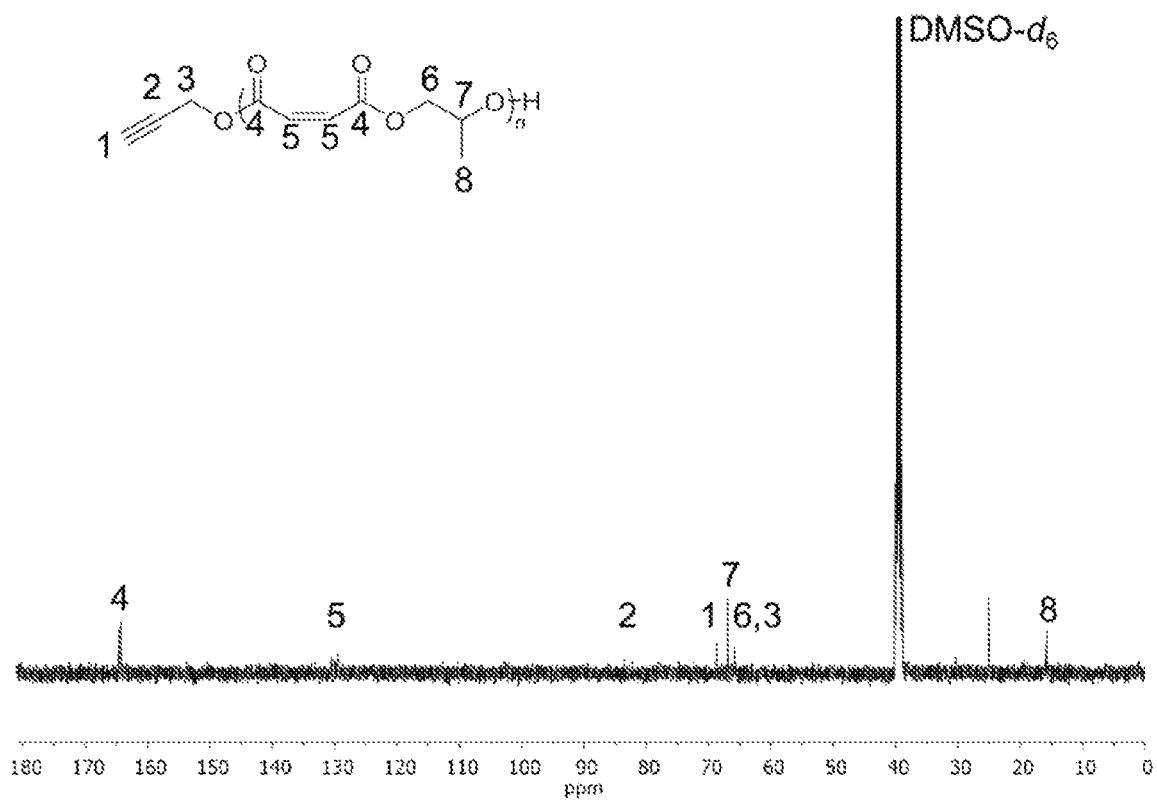
FIG. 9 is a $^{13}C$ NMR spectra for DP 25 propargyl alcohol initiated PPM (Table 2, Entry 6) (125 MHz, DMSO-$d_3$, 303 K).
Figure 10:
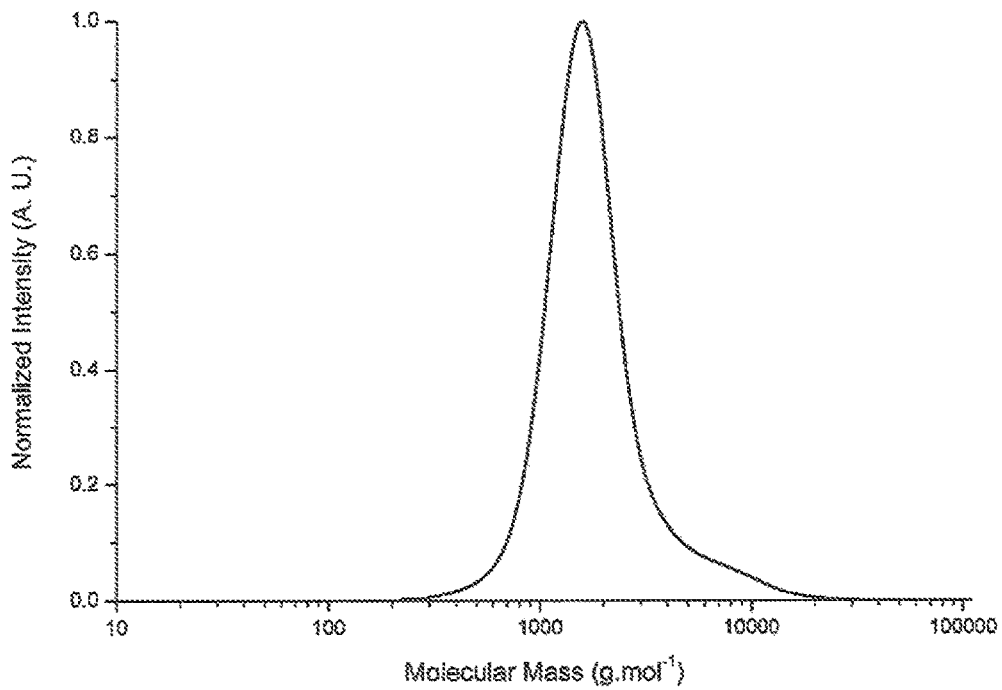
FIG. 10 is a SEC chromatogram for DP 25 propargyl alcohol initiated PPM (Table 2, Entry 6). Molecular mass determined against poly(styrene) standards.
Figure 11:
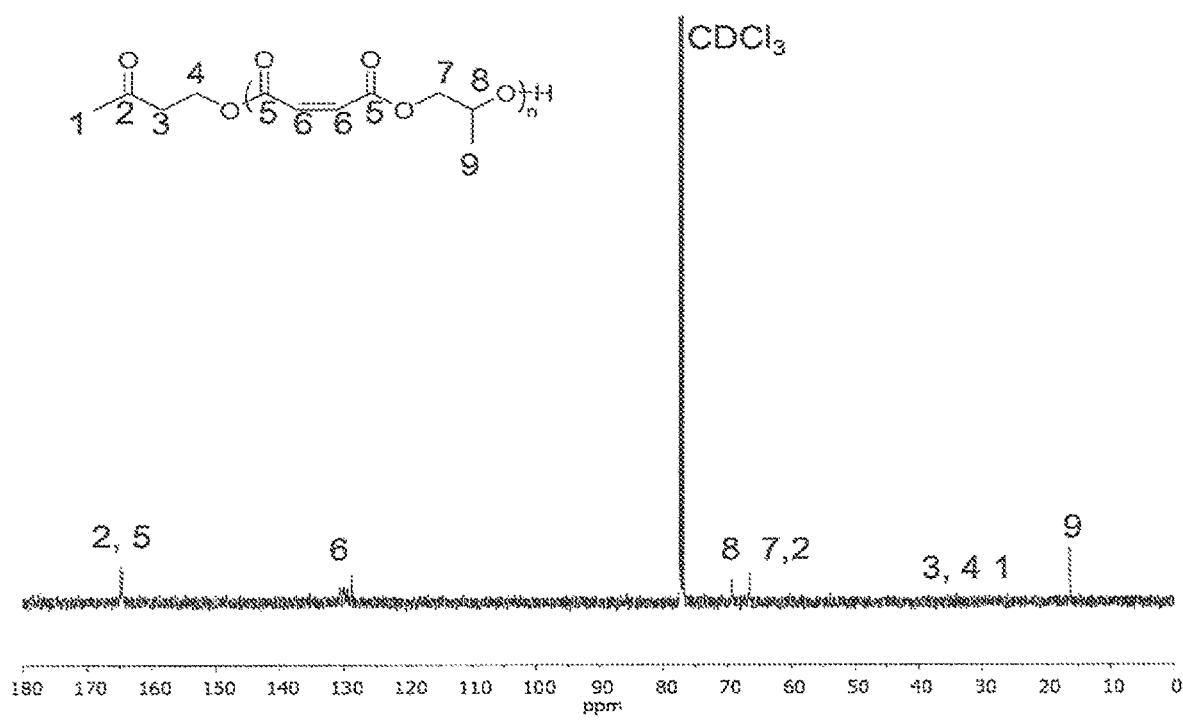
FIG. 11 is a $^{13}C$ NMR spectra for DP 25 4-hydroxybutan-2-one initiated PPM (Table 2, Entry 10) (125 MHz, $CDCl_3$, 303 K).
Figure 12:
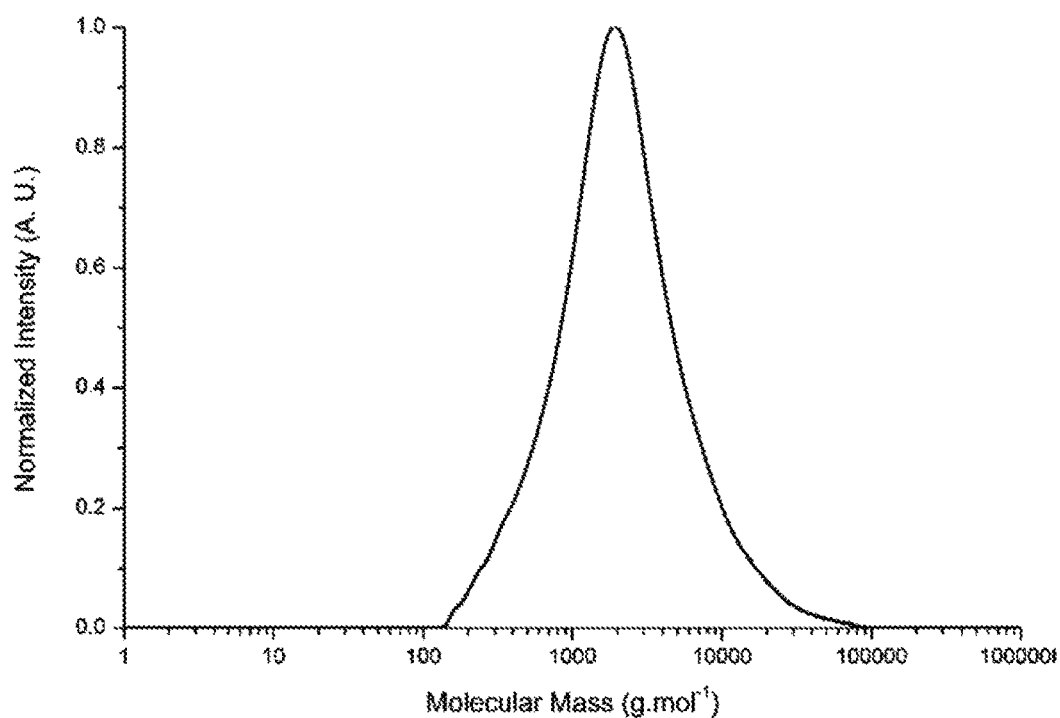
FIG. 12 is a SEC chromatogram for DP 25 4-hydroxybutan-2-one initiated PPM (Table 2, Entry 10). The molecular mass was determined against poly(styrene) standards.
Figure 13:
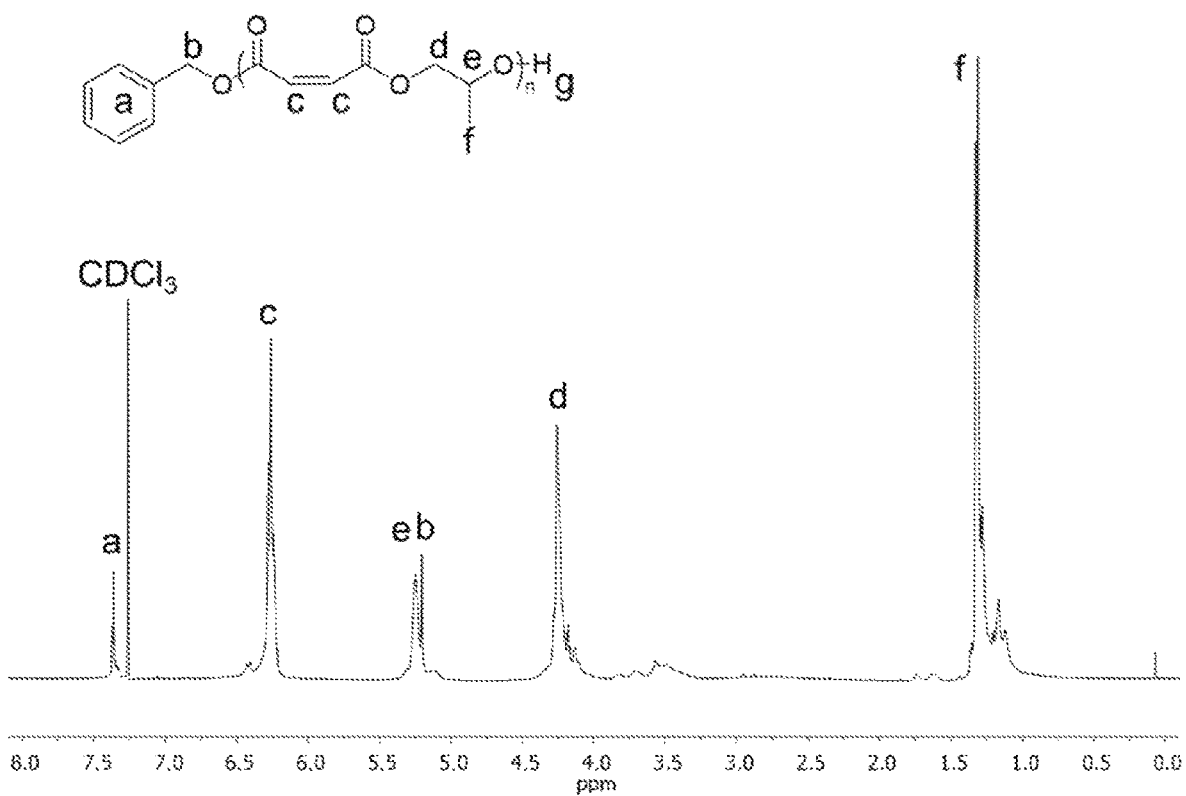
FIG. 13 is a $^1H$ NMR spectra for DP 25 benzyl alcohol initiated PPM polymerized in hexanes at 60° C. (Table 3, Entry 2) (300 MHz, $CDCl_3$, 303 K).
Figure 14:
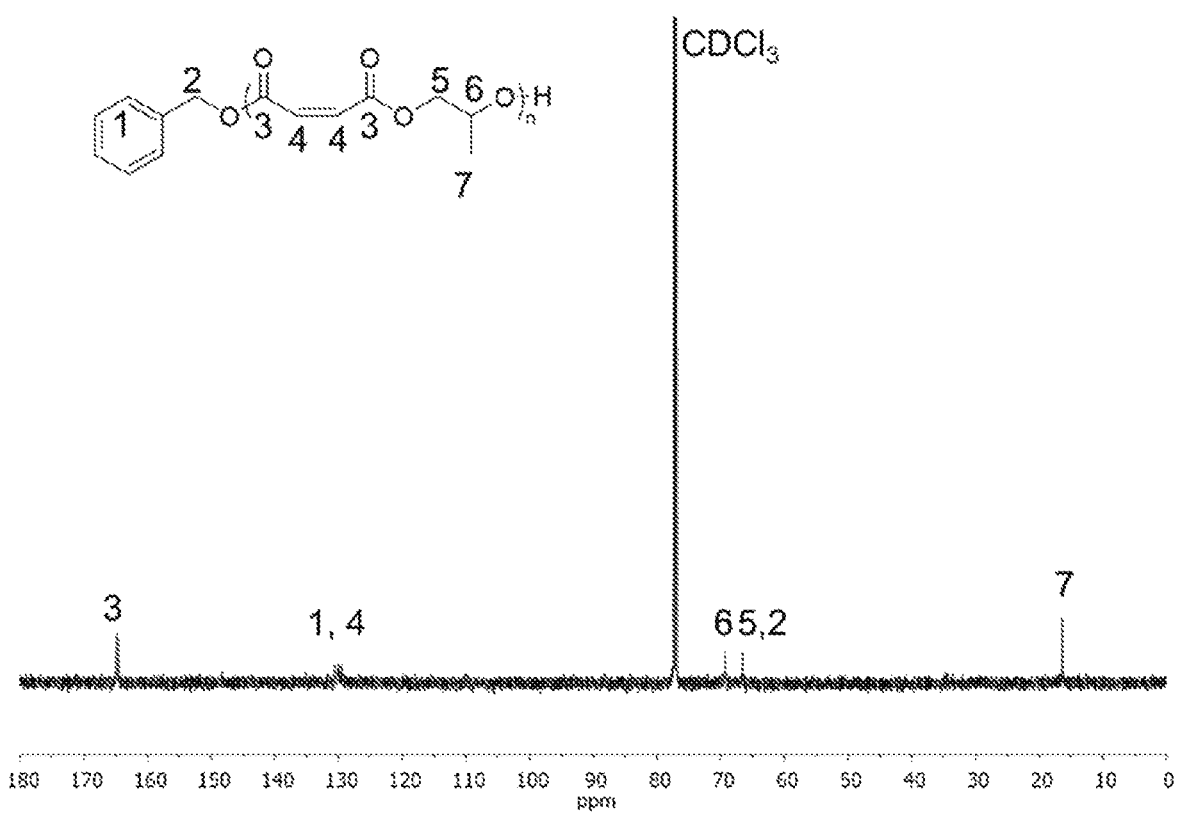
FIG. 14 is a $^{13}C$ NMR spectra for DP 25 benzyl alcohol initiated PPM polymerized in hexanes at 60° C. (Table 3, Entry 2) (125 MHz, $CDCl_3$, 303 K).
Figure 15:
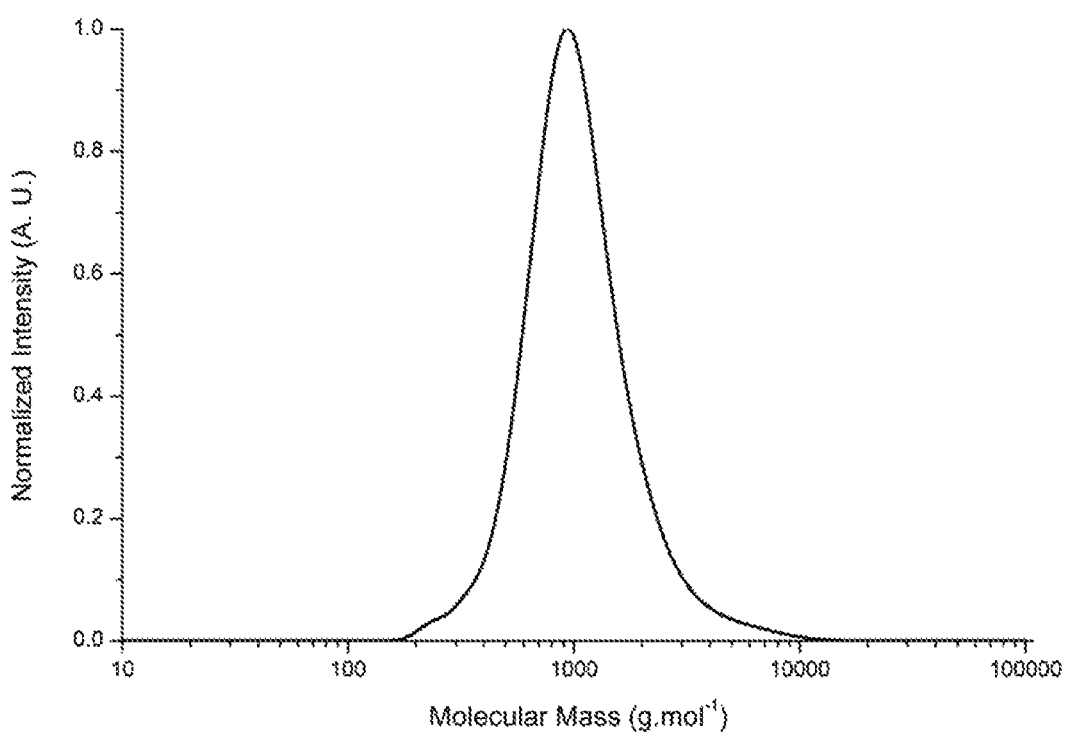
FIG. 15 is a SEC chromatogram for DP 25 benzyl alcohol initiated PPM polymerized in hexanes at 45° C. (Table 3, Entry 2). Molecular mass determined against poly(styrene) standards.

In order to quantify the degree of control over the copolymerization kinetics, a range of DPs were targeted. PPM was synthesized targeting a DP of 10, 25, 50 and 100 based on the ratio of initiator to comonomers (FIG. 6). Molecular masses of the final copolymers were characterized using $^1$H NMR spectroscopy and SEC. The DP of the resultant copolymer was calculated based on the ratio of the benzyl alcohol methylene proton resonances ($\delta=5.01$ ppm) to the methine proton resonance of ring-opened propylene oxide ($\delta=5.25$ ppm) and alkene proton resonances of ring-opened maleic anhydride ($\delta=6.26$ ppm). The molecular mass was observed to increase linearly with the targeted DP with low $Đ_M$ observed throughout.

Naturally, a benzyl chain-end is not an ideal end group for post-polymerization or post-printing modification with bioactive species. To this end, the ROCOP of MAn and PO was conducted under the same conditions, using propargyl alcohol as a primary alcohol initiator (Scheme 3). $^1$H NMR spectroscopic analysis of the resultant PPM showed the presence of proton resonances at $\delta=4.78$ and 2.27 ppm, corresponding to the methylene and alkyne protons of propargyl alcohol respectively. MALDI-ToF MS further confirmed the initiation from propargyl alcohol. Two distributions were observed, one major and one minor distribution, both with molecular masses corresponding to a propargyl alcohol chain-end. As observed with the benzyl alcohol initiation, the major distribution was PPM with complete repeat units and the minor distribution contained an additional propylene oxide unit, presumably at the chain end. No other distributions were observed, which indicates that a high degree of chain end-group fidelity is achieved.

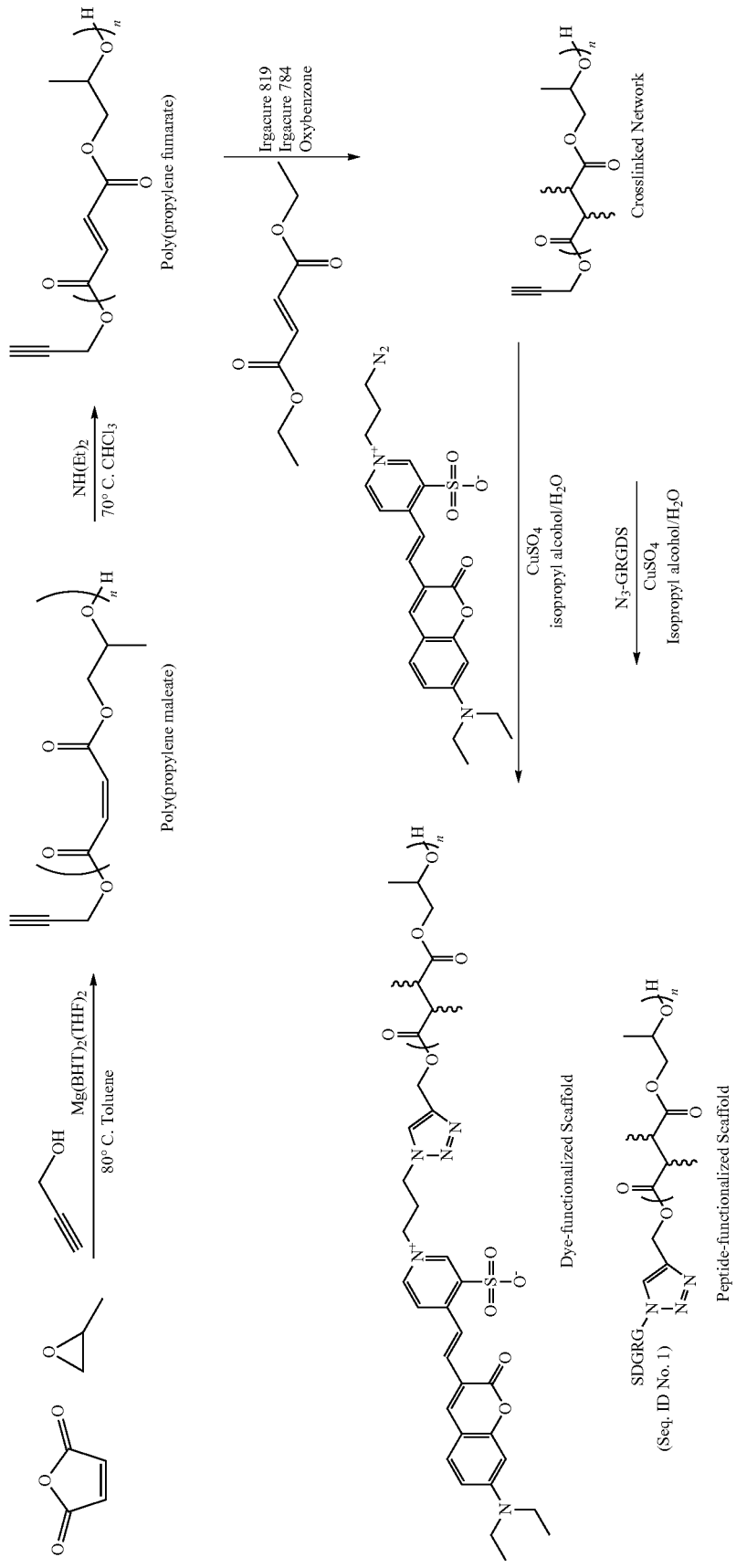
Scheme 3
Synthesis of dye- and peptide-functionalized poly(propylene fumarate) scaffolds from the ROCOP of maleic anhydride and propylene oxide using propargyl alcohol as an initiator.

The ROCOP of MAn and PO was further explored using the primary alcohol 4-hydroxy-2-butanone (4HB) as an initiating species under the same conditions. 4HB was chosen as an initiator to facilitate post-printing functionalization with amines or hydroxylamines. Initiation from 4HB was confirmed by $^1$H NMR spectroscopy of the resultant PPM material, with the characteristic proton resonances of the acyl methylene and methyl groups observed at $\delta$=4.45 and 2.19 ppm, respectively. Again, MALDI-ToF MS was used to confirm the chain-end fidelity of the polymer.

Further analysis of the $^1$H NMR spectra showed the proton resonances of each end-group remained with integrations matching the polymer before isomerization, thus demonstrating the end-group is not affected by the isomerization process. This was further confirmed by SEC analysis of the polymers before and after isomerization displaying similar molecular mass distributions.

The properties of the PPF polymers produced in these experiments are summarized in Table 2, below:

TABLE 2

Properties of PPF polymers produced using Mg(BHT)$_2$(THF)$_2$ as a catalyst with varying alcohol initiators and targeted DPs

| Entry | Initiator (I) | DP | [MAn]:[PO]:[I] | MAn Conv. (%) | $M_n{}^b$,$_{NMR}$ (kDa) | $M_n{}^c$,$_{SEC}$ (kDa) | $M_w{}^c$,$_{SEC}$ (kDa) | $Đ_M{}^c$ |
|---|---|---|---|---|---|---|---|---|
| 1 | Benzyl alcohol | 10 | 10:10:1 | 75 | 1.8 | 2.8 | 3.3 | 1.17 |
| 2 | Benzyl alcohol | 25 | 25:25:1 | 85 | 2.9 | 3.7 | 4.6 | 1.25 |
| 3 | Benzyl alcohol | 50 | 50:50:1 | 81 | 7.8 | 5.8 | 7.4 | 1.27 |
| 4 | Benzyl alcohol | 100 | 100:100:1 | 85 | 13.2 | 9.7 | 16.4 | 1.69 |
| 5 | Propargyl alcohol | 10 | 10:10:1 | 97 | 1.6 | 2.4 | 2.7 | 1.14 |
| 6 | Propargyl alcohol | 25 | 25:25:1 | 96 | 2.2 | 3.0 | 3.3 | 1.11 |
| 7 | Propargyl alcohol | 50 | 50:50:1 | 91 | 4.8 | 6.6 | 10.0 | 1.52 |
| 8 | Propargyl alcohol | 100 | 100:100:1 | 93 | 6.9 | 9.8 | 13.9 | 1.42 |
| 9 | 4HB$^d$ | 10 | 10:10:1 | 89 | 1.6 | 1.9 | 2.3 | 1.19 |
| 10 | 4HB$^d$ | 25 | 25:25:1 | 90 | 3.3 | 2.3 | 2.4 | 1.05 |
| 11 | 4HB$^d$ | 50 | 50:50:1 | 86 | 4.9 | 6.9 | 11.5 | 1.67 |
| 12 | 4HB$^d$ | 100 | 100:100:1 | 89 | 10.7 | 11.2 | 16.4 | 1.46 |

$^a$Monomer conversion determined by $^1$H NMR spectroscopy.
$^b$Determined by end-group analysis by $^1$H NMR spectroscopy.
$^c$Determined by SEC in THF against polystyrene standards.
$^d$4-Hydroxy-2-butanone.

However, as a consequence of the ionization energy required, a cleavage side reaction occurred wherein the end-group was cleaved to release acrolein as a by-product. As a consequence, the end-group appears to be water initiation by MALDI-ToF MS, which is not observed in $^1$H and $^{13}$C NMR spectroscopy of the same material. Previous literature has shown the presence of water during polymerization poisons the catalyst rather than initiates polymerization. Unlike the benzyl alcohol and propargyl alcohol initiated system, 3 distributions were observed, corresponding to a full PPM repeat unit with one, two or three additional PO repeat units. However, each distribution showed the 4HB chain end and thus, it can be assumed the chain end fidelity is preserved despite an increased preference for PO incorporation.

In order to produce end-group modifiable PPF, the isomerization of PPM must be performed without side reactions leading to cleavage or other side reactions of the end-group species. Following a previously reported procedure (See, DiCiccio, A. M.; Coates, G. W., *J. Am. Chem. Soc.*, 2011, 133, 10724-10727, the disclosure of which is incorporated herein by reference in its entirety), the isomerization of benzyl alcohol initiated PPM was conducted under reflux for 24 h at a concentration of 0.5 M in CHCl$_3$, using diethylamine (0.15 eq. per alkene) as a catalyst. The solution was washed with sodium phosphate buffer solution (3:1 v/v) in order to completely remove the diethylamine before solvent was removed via rotary evaporation. $^1$H NMR spectroscopy of the recovered polymer showed a complete reduction of the proton resonance attributable to cis-alkene protons ($\delta$=6.2 ppm) and a new proton resonance attributable to trans-alkene protons ($\delta$=6.7 ppm), which indicates the complete isomerization of the cis-alkene containing PPM into the trans-alkene containing PPF.

See also, FIGS. 1-3, 7-12.

As a comparison against the production of PPM using other organometallic catalysts at lower temperatures, the ROCOP of MAn and PO was conducted at a total monomer concentration of 2 M in hexanes at 45° C., using benzyl alcohol as an initiator and Mg(BHT)$_2$(THF)$_2$ as a catalyst. As a consequence of the lower temperature, longer polymerization times were necessary and thus, the polymerization was allowed to continue for 96 h before quenching. Unlike the polymerization in toluene, MAn was not observed to dissolve before the solution was heated. Similarly, the polymer was observed to be immiscible with the hexanes solution throughout the majority of the polymerization, which also prevented monomer conversion from being monitored by $^1$H NMR spectroscopy. However, analysis of the resultant polymer by $^1$H NMR spectroscopy showed that PPM was synthesized with the targeted DP based on the initial molar ratio of initiator to monomers (Table 3). MALDI-ToF MS further proved that end-group fidelity was maintained during the polymerization with no distributions attributable to water initiation or transesterification side reactions with water. SEC analysis of the polymer showed that the molecular mass corresponded to both the theoretical $M_n$ and $M_n$ based on $^1$H NMR spectroscopy, with a low $Đ_M$ (1.17) even with the majority of the polymer immiscible with the reaction solution.

TABLE 3

Molecular mass properties of PPF produced in hexanes to varying DPs

| Entry | DP | Time (days) | $M_n{}^a$,$_{NMR}$ (kDa) | $M_n{}^b$,$_{SEC}$ (kDa) | $M_w{}^b$,$_{SEC}$ (kDa) | $Đ_M{}^b$ |
|---|---|---|---|---|---|---|
| 1 | 10 | 4 | 1.3 | 1.1 | 1.3 | 1.17 |
| 2 | 25 | 6 | 2.9 | 1.9 | 2.3 | 1.19 |

TABLE 3-continued

Molecular mass properties of PPF produced in hexanes to varying DPs

| Entry | DP | Time (days) | $M_n^a$,$_{NMR}$ (kDa) | $M_n^b$,$_{SEC}$ (kDa) | $M_w^b$,$_{SEC}$ (kDa) | $Đ_M^b$ |
|---|---|---|---|---|---|---|
| 3 | 50 | 8 | 6.0 | 3.6 | 5.5 | 1.55 |
| 4 | 100 | 10 | 8.6 | 8.0 | 11.6 | 1.44 |

[a]Determined by end-group analysis by $^1$H NMR spectroscopy.
[b]Determined by SEC in THF against polystyrene standards.

See also, FIGS. 4, 13-15.

Figure 4:
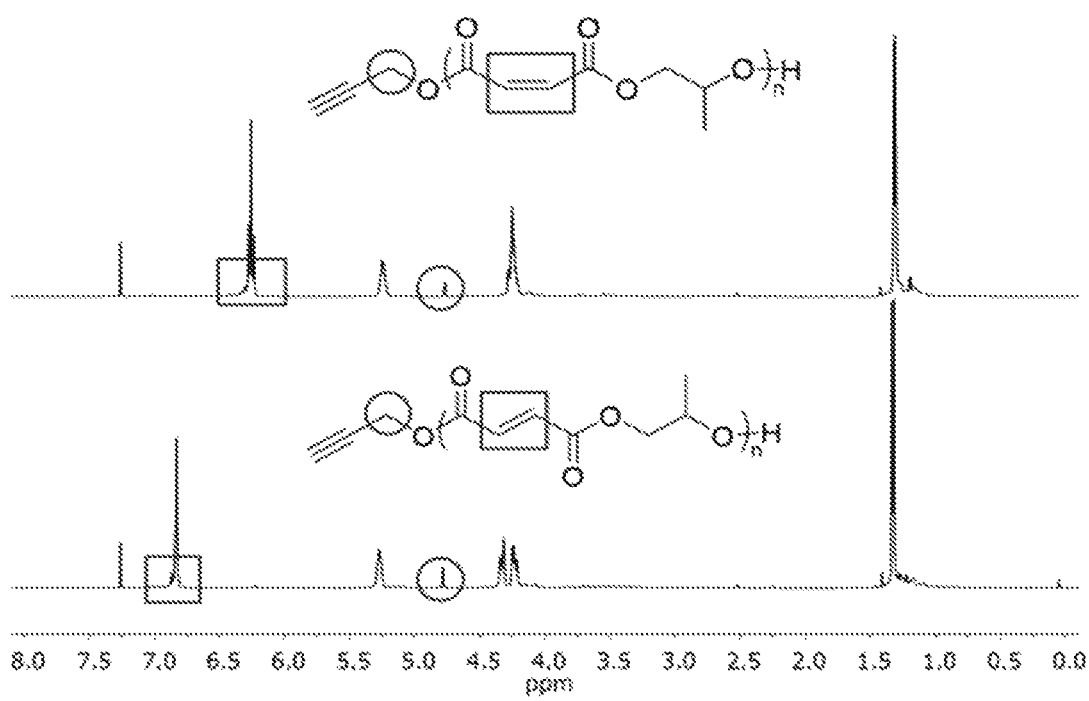
FIG. 4 is a $^1H$ NMR spectra comparison of (upper) the precursor DP25 propargyl alcohol-initiated PPM produced in hexanes (Table 2, Entry 6) and (lower) the resultant propargyl alcohol-initiated PPF after isomerization (500 MHz, $CDCl_3$, 303 K).

As set forth above, although this system requires longer polymerization times as a consequence of reduced temperature, this method may be advantageous in terms of scale-up reactions. The solubility of all reagents and not the polymer into hexanes means the majority of impurities are removed from the polymer purely by decanting off the hexanes solution after polymerization, therefore reducing the number of precipitations required to recover pure PPM. Advantageously, once the decanted solution is cooled to room temperature, the unreacted MAn was observed to recrystallize and can be recovered for further use. As a consequence of PPM produced in toluene and hexanes being chemically identical, the isomerization to PPF was carried out in identical conditions and resulted in complete conversion of all cis-alkenes to trans-alkenes (FIG. 4).

As set forth above, in order to print 3D scaffolds, the end-functionalized PPF was mixed into a resin with a previously reported composition. See, Luo, Y.; Dolder, C. K.; Walker, J. M.; Mishra, R.; Dean, D.; Becker, M. L., *Biomacromolecules*, 2016, 17, 690-697, the disclosure of which is incorporated herein in its entirety. Briefly, end-functionalized PPF was dissolved into an equal mass of diethyl fumarate (DEF) and a mixture of photoinitiators and light scattering agents (4.1 wt. %) were mixed evenly throughout the resin. Thin films were printed using an EnvisionTEC Micro cDLP printer. Propargyl alcohol-functionalized PPF discs (Ø=6 mm) were printed and the surface area calculated. Chromeo® 546-azide dye was attached to the discs using copper-mediated azide-alkyne cycloaddition (CuAAC) and the surface concentration of propargyl alcohol end-groups was calculated through a subtractive concentration method. That is, the decrease in concentration of the dye solution was measured through UV/visible and fluorescence spectroscopy after the films were dipped into the solution. Films were coated in the presence of catalyst and without catalyst and compared against the original solution. It was determined that the physical adsorption of dye onto the surface had a concentration of 0.1 (±0.1) pmol·cm$^{-2}$ compared to the CuAAC surface attachment concentration of 30.0 (±3.3) pmol·cm$^{-2}$. Other surface functionalized materials, such as PEG-peptide hydrogels and peptide cross-linked poly(ester urea)s have exhibited similar surface concentrations with positive studies in increased cell viability. Selective attachment of an azide-functionalized dye was further demonstrated through the CuAAC of Megastokes® 673-azide dye onto a thin film covered with a hexagonally latticed transmission electron microscopy (TEM) grid, acting as a mask. The covered film was submerged into a solution of copper sulfate and sodium ascorbate in an isopropyl alcohol and water mixture for 1 h. The film was washed three times with deionized water and placed under a fluorescence microscope fitted with a 673 nm filter for imaging.

Figure 16:
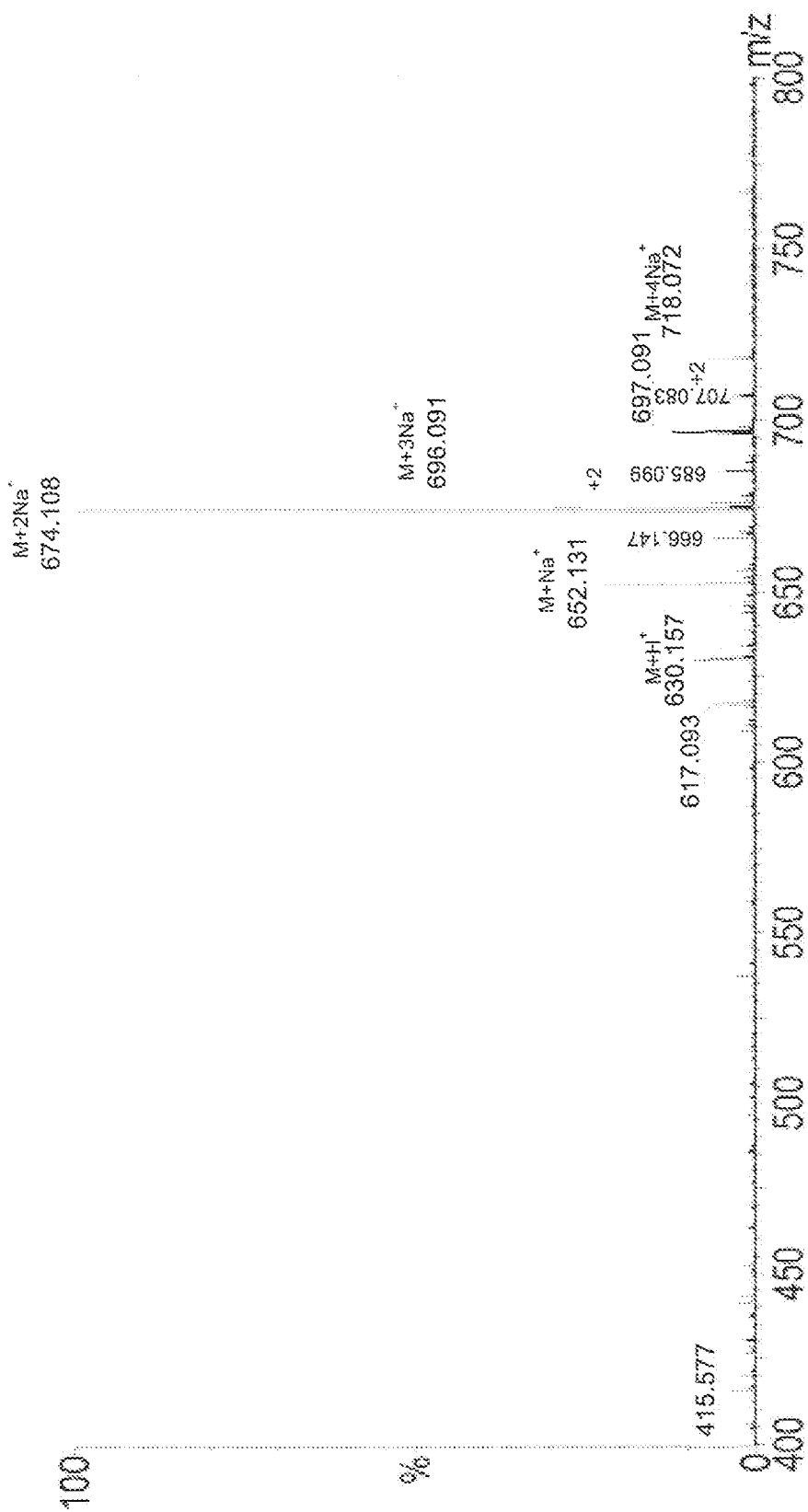
FIG. 16 is an ESI spectrum for azide-functionalized GRGDS [Seq. ID No. 1] ($N_3$-GRGDS [Seq. ID No. 1]) polypeptide sequence.
Figure 17:
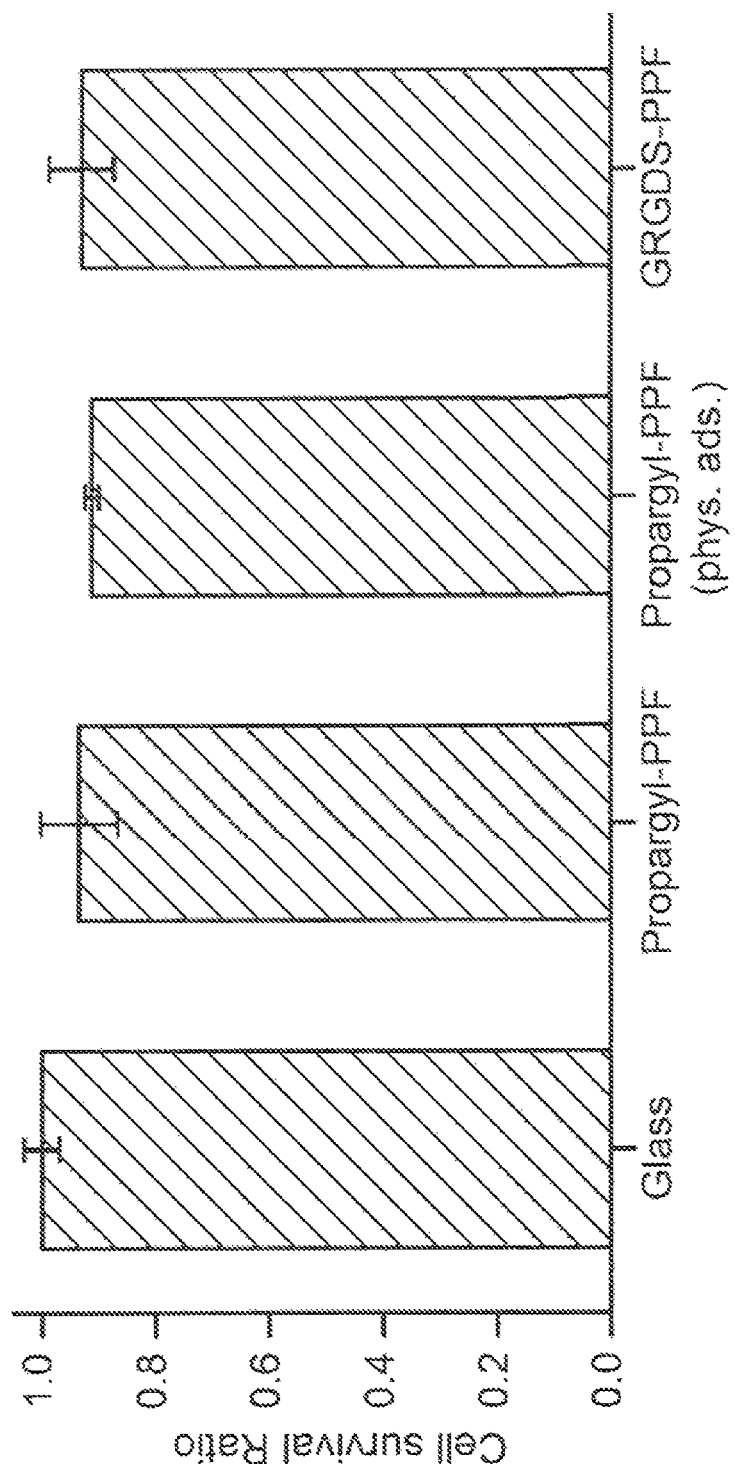
FIG. 17 is a graph showing cell survival ratio of propargyl alcohol-functionalized PPF, physically adsorbed $N_3$-GRDGS [Seq. ID No. 1] on propargyl alcohol-functionalized PPF and GRDGS [Seq. ID No. 1]-PPF bioconjugate films as determined by LIVE/DEAD™ assay.

In order to confirm that the end-functionalized polymers can be derivatized with bioactive peptides, a cell study was performed using mouse MC3T3-E1 cells to assess whether the peptide is bioactive after surface functionalization. The peptide sequence GRGDS [Seq. ID No. 1] is an analog of the RGD sequence that has been used widely to enhance cell adhesion to biomaterial surfaces. Azide-functionalized GRGDS [Seq. ID No. 1] ($N_3$-GRGDS [Seq. ID No. 1]) was synthesized via solid phase peptide synthesis for this purpose and attached to propargyl alcohol end-functionalized PPF discs using CuAAC. (See FIG. 16) Discs were also prepared without $N_3$-GRGDS [Seq. ID No. 1] addition and without copper sulfate catalyst addition to act as control specimens. Circular discs were printed with a diameter of 6 mm and washed with chloroform, acetone and ethanol in order to remove photoinitiator by-products. Following sterilization with 70% ethanol and UV light, the discs were then tested for cytotoxicity. MC3T3-E1 cells were cultured on the PPF discs at 250 cells·mm$^{-2}$. After 48 h incubation at 37° C. and 5% $CO_2$, the discs were subjected to a Live/Dead® assay where live cells can be identified by green calcein AM dye and dead cells can be identified by red ethidium homodimer dye under fluorescence microscopy. Discs were quantified in triplicate with pre-cultured glass slides used as a control (FIG. 17). Discs derivatized with the GRGDS [Seq. ID No. 1] peptide showed similar cell survival ratios to end-functionalized PPF (no RGD solution added) and physically adsorbed end-functionalized PPF (RGD solution added with no copper) control discs. Normalization of the survival ratios against a glass slide control showed greater than 90% cell viability for all films. Thus, the cytotoxicity of end-functionalized PPF is low and directly comparable to both step-growth polymerization produced PPF and PPF produced using $Mg(OEt)_2$ as a ROCOP catalyst.

Histochemical staining of actin and nuclei was also conducted in order to visualize cell attachment. GRGDS [Seq. ID No. 1] functionalized discs showed enhanced spreading after seeding, with well-defined actin filament formation over a larger area than both end-functionalized PPF controls consistent with integrin assisted adhesion. The data gathered in these initial cell studies suggests that the GRGDS [Seq. ID No. 1] peptide remained bioactive and bioavailable when tethered to the propargyl alcohol-initiated PPF discs and further functionalization with other peptides or bioactive molecules is feasible. More advanced studies of ligand, concentration and degradation are ongoing in relevant preclinical models.

The end-group modifiable poly(propylene fumarate) (PPF) of the present invention has been synthesized through the use of ROCOP and a functional primary alcohol initiator. As a consequence of the nature of the ROCOP, end-group modifiable PPF can be made to any targeted molecular mass without the loss of the end-group functionality from trans-esterification side reactions or cyclization during either the polymerization or isomerization. Furthermore, the ability to modify the surface of PPF scaffolds post-polymerization and post-printing has been demonstrated with the attachment of small molecule dyes and short-chain peptides. The low cytotoxicity observed in subsequent cell assays has shown this method of production of PPF to be comparable to previous methods, with the potential for directed cell differentiation through peptide functionalization of the material.

Methods for Making the Functionalized Propylene Oxide Monomers

In a still another aspect, the present invention is directed to novel method for forming the functionalized propylene oxide comonomers discussed above. In general outline, these reactions involve the addition of a functional group to the propylene oxide comonomer using phase transfer chemistry. In these reactions, one or more alcohol containing a desired functional group, such as propargyl alcohol, is dissolved in an aqueous solution containing a base, such as NaOH or KOH, and reacted with a solution containing a halogenated propylene oxide, such as (±)-epichlorohydrin, a phase transfer agent such as tetrabutylammonium hydrogensulfate, and an organic solvent. During the reaction, the molecule containing the functional group is transferred from the aqueous phase to the organic phase where it bonds to the end of the propylene oxide by an ether bond. Accordingly, by forming an ether bond at the primary halide, different types of functionalized propylene oxide may be obtained and used to synthesize functionalized PPFs by ring-opening copolymerization with metal catalyst, as described in more detail below.

In various embodiments, the functional group on the alcohol may be an alkyl or aryl group containing a functional group capable of entering into a "click" or other reaction with a corresponding functional group on a bioactive compound (i.e. bioactive drugs, peptides, proteins, sugars, etc.), or any other compound to be added to the PPF polymer. In various embodiments, the alcohol used to form the functionalized propylene oxide comonomers of the present invention may include, without limitation, propargyl alcohol, o-nitrobenzyl alcohol, (±)-epichlorohydrin, or combinations thereof.

In one or more of these embodiment, a suitable base will include, without limitation, NaOH or KOH. In some of these embodiments, the halogenated propylene oxide may be, without limitation, (±)-epichlorohydrin. In various embodiments, the phase transfer agent may be tetrabutylammonium hydrogensulfate tetrahexylammonium hydrogensulfate tetraoctylammonium hydrogensulfate tetradecylammonium hydrogensulfate. In one or more of these embodiments, suitable organic solvents may include, without limitation, toluene, hexane, mixed hexanes, heptane, octane, dioxane, pentane, nonane, decane dodecane or combinations thereof.

In one or more embodiments, the functionalized propylene oxide comonomers may be prepared according to Scheme 4, below:

Scheme 4

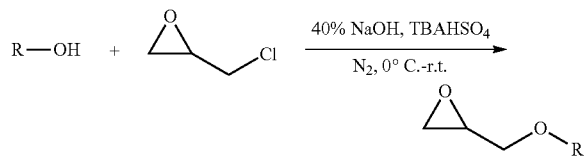

where R is a functional group, oran alkyl or aryl group containing a functional group, that is capable of entering into a "click" or other reaction with a corresponding functional group on a bioactive compound (i.e. bioactive drugs, peptides, proteins, sugars, etc.), functional species or any other compound to be added to the PPF polymer. In some embodiments, the targeted bioactive compound may be functionalized to add the corresponding functional group provided that doing so does not denature the bioactive compound or otherwise render the bioactive compound, functional species, or other compound to be added ineffective for its intended purpose. In one or more embodiments, R will be an alkyne, alkene, hydroxyl, protected hydroxyl, thiol or halide functional group or an alkyl or aryl group containing such a functional group.

In various embodiments, the method of forming functionalized propylene oxide comonomers of the present invention begins with adding propargyl alcohol to an aqueous solution containing a base selected from the group consisting or sodium hydroxide (NaOH), potassium hydroxide (KOH), and combinations thereof. In some of these embodiments, the propargyl alcohol is added dropwise to an aqueous solution containing from about 20% to about 50% NaOH by weight at a temperature of from about −10° C. to about 30° C. while stirring. In some of these embodiments the aqueous solution containing from about 20% to about 45%, in other embodiments, from about 20% to about 40%, in other embodiments, from about 20% to about 35%, in other embodiments, from about 20% to about 30%, in other embodiments, from about 30% to about 50%, in other embodiments, from about 35% to about 50%, in other embodiments, from about 40% to about 50% NaOH by weight. In some embodiments, the aqueous solution is formed at a temperature of from about −10° C. to about 20° C., in other embodiments from about −10° C. to about 15° C., in other embodiments from about −10° C. to about 10° C., in other embodiments from about −10° C. to about 5° C., in other embodiments from about −10° C. to about 0° C., in other embodiments from about −5° C. to about 30° C., in other embodiments from about 0° C. to about 30° C., and in other embodiments from about 10° C. to about 30° C.

Next, (±)-epichlorohydrin and tetrabutylammonium hydrogensulfate are dissolved in a suitable organic solvent, such as hexane and added with water to the aqueous propargyl alcohol solution under an inert atmosphere. The temperature is allowed to return to ambient temperature and the reaction is allowed to proceed for from about 1 hours to about 24 hours under an inert atmosphere, such as a $N_2$ blanket, to produce glycidyl propargyl ether. In some embodiments, the reaction is allowed to proceed from about 5 to about 24 hours, in other embodiments, from about 10 hours to about 24 hours, in other embodiments, from about 12 hours to about 24 hours, in other embodiments, from about 1 hours to about 20 hours, in other embodiments, from about 1 hours to about 15 hours, and in other embodiments, from about 1 hours to about 10 hours.

The reaction is then quenched and the resulting crude product purified by any suitable means known in the art. In some embodiments, the reaction is quenched in brine. In some of these embodiments, the crude product is extracted with a suitable organic solvent and purified by column chromatography or distillation to produce a purified glycidyl propargyl ether. In some of these embodiments, the step of extraction entails extracting the crude product with three portions of dichloromethane (DCM), drying the combined organic layers over $Na_2SO_4$, filtering out the $Na_2SO_4$, and concentrating the crude product by rotary evaporation.

In some embodiments, the functionalized propylene oxide comonomer may be prepared as set forth in Example 18, below.

In some other embodiments, the functionalized propylene oxide comonomer 2-[[(2-nitrophenyl)methoxy]methyl]oxirane (NMMO) may be produced from o-nitrobenzyl alcohol using substantially the same reaction. In these embodiments, o-nitrobenzyl alcohol is dissolved in suitable solvent such as 1,4-dixoane or THF, and a transfer agent, such as tetrabutylammonium hydrogensulfate, and an aqueous solution containing a base such as sodium hydroxide (NaOH) or potassium hydroxide (KOH). In some of these embodiments, the aqueous solution containing from about 20% to about 50% NaOH by weight In some of these embodiments the aqueous solution containing from about 20% to about 45%, in other embodiments, from about 20% to about 40%, in other embodiments, from about 20% to about 35%, in other embodiments, from about 20% to about 30%, in other embodiments, from about 30% to about 50%, in other embodiments, from about 35% to about 50%, in other embodiments, from about 40% to about 50% NaOH by weight.

Next, (±)-epichlorohydrin is added to the mixture at a temperature of from about −10° C. to about 30° C. while stirring. In some embodiments, the (±)-epichlorohydrin is added dropwise to the mixture at a temperature of from about −10° C. to about 20° C., in other embodiments from about −10° C. to about 15° C., in other embodiments from about −10° C. to about 10° C., in other embodiments from about −10° C. to about 5° C., in other embodiments from about −10° C. to about 0° C., in other embodiments from about −5° C. to about 30° C., in other embodiments from about 0° C. to about 30° C., and in other embodiments from about 10° C. to about 30° C.

The temperature is then allowed to return to ambient temperature and the reaction is allowed to proceed for from about 1 hours to about 96 hours (or until the reagents have fully reacted) under an inert atmosphere, such as a $N_2$ blanket to produce 2-[[(2-nitrophenyl)methoxy]methyl]oxirane (NMMO). In some embodiments, the reaction is allowed to proceed from about 1 to about 72 hours, in other embodiments, from about 1 hours to about 48 hours, in other embodiments, from about 1 hours to about 24 hours, in other embodiments, from about 6 hours to about 96 hours, in other embodiments, from about 12 hours to about 96 hours, and in other embodiments, from about 24 hours to about 72 hours.

The resulting crude product purified by any suitable means known in the art. In some embodiments, the 2-[[(2-nitrophenyl)methoxy]methyl]oxirane (NMMO) is extracted two or more times into an organic phase by the addition of an organic solvent such as diethyl ether or THF. Each time the organic phase is separated and collected. The combined organic phase are then washed two or more times with an excess of $H_2O$, saturated sodium bicarbonate, and saturated sodium chloride. Again, the organic layers are separated and collected with each washing and then combined and dried over $MgSO_4$, filtered, concentrated by rotary evaporation, and purified by column chromatography or distillation to produce a purified 2-[[(2-nitrophenyl)methoxy]methyl]oxirane (NMMO).

Methods for Making the Monomer-Functionalized PPF Polymer

In another aspect, the present invention is directed to novel method for forming the functionalized PPF polymers discussed above. Typically, the ROP method for PPF synthesis uses maleic anhydride and propylene oxide as comonomers, which undergo an alternating ring-opening copolymerization (ROCOP) using an organometallic catalyst before being isomerized to form the PPF. Under the correct reaction conditions, PPF synthesis by alternating ring-opening copolymerization (ROCOP) using an organometallic catalyst shows high end-group fidelity, a precise control of molecular weights during polymerization, linear molecular weight growth and narrow, monomodal molecular mass distribution. By using the functionalized propylene oxides described above in this ROP reaction, monomer functionalized PPF polymers having functionalized side chains are produced. In one or more embodiments, these monomer functionalized PPF polymers may also be end functionalized through a functionalized initiating alcohol, as described above.

There are two features necessary for controlled polymerization, one is no termination and the other is no chain transfer. These two features make controlled polymerization ideal for the synthesis of well-defined molecular weight polymers. Typically, for cyclic polyesters the general method of employing controlled polymerization is using a catalyst to initiate ROP. However, in order to produce PPF for bone tissue engineering clinical scaffolds or any other biomaterial products, the in vivo influence of the material must be taken into account. An ideal material for bone tissue engineering is made using a mild process, processed in a non-toxic way, and finally printed into non-toxic scaffolds. For the synthesis step, every reagent added into the reaction system must be either non-toxic or easily removed by a subsequent process. Based on the current ROP methods employed for PPF synthesis, only the catalyst and solvent have a potential to introduce toxicity to final polymers. The solvent can be removed readily and thus, only the catalyst must be specially considered. The organometallic compound must be low toxicity because there are no perfect methods to remove trace quantities from materials. To satisfy this requirement, it is necessary to consider both the central metal and surrounding ligands for use in the human body.

One example of the organometallic catalysts for ROP that has been found to satisfy all these requirements is magnesium 2,6-di-tert-butyl-4-methylphenoxide $(Mg(BHT)_2(THF)_2)$. The central magnesium ion is a non-cytotoxic component for human body, and ligand 2,6-di-tert-butyl-4-methylphenoxide (butylated hydroxytoluene, i.e. BHT) has been approved for use as a food additive and stabilizer by the Food and Drug Administration in 1954 and has the general structure:

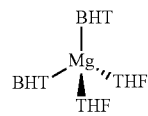

This magnesium catalyst is not only non-toxic, but has good ability to control the ROP as well as the ROCOP process, is not sensitive to air, and allows for the use of different initiators without affecting the catalytic activity.

In various embodiments, the functionalized PPF polymers of the present invention may be synthesized as shown in Scheme 5, below:

Scheme 5

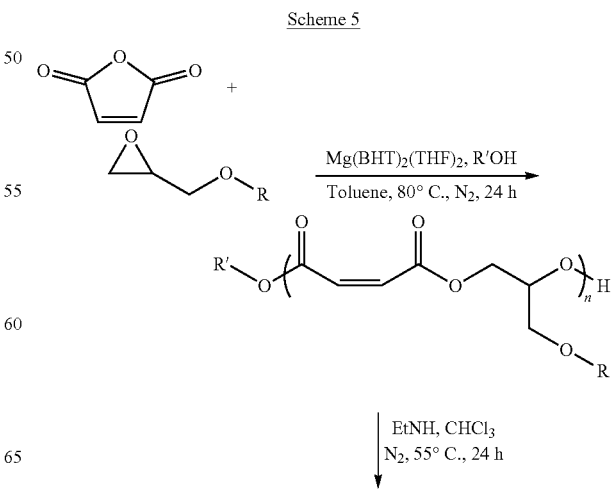

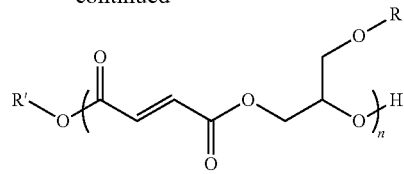

where R is a functional group, or an alkyl or aryl group containing a functional group, that is capable of entering into a "click" or other reaction with a corresponding functional group on a bioactive compound (i.e. bioactive drugs, peptides, proteins, sugars, etc.), or any other compound to be added to the PPF polymer; and R' is an end functional group as described above. In various embodiments, R' may be, without limitation, one or more benzyl groups, alkyne groups, propargyl groups, allyl groups, alkene groups, 4-dibenzyocyclooctyne groups, cyclooctyne groups, ketone groups, aldehyde groups, tertiary halogen groups, or a combination thereof.

In various embodiments, the functionalized PPF polymers of the present invention may be synthesized as shown in Scheme 6, below:

Scheme 6

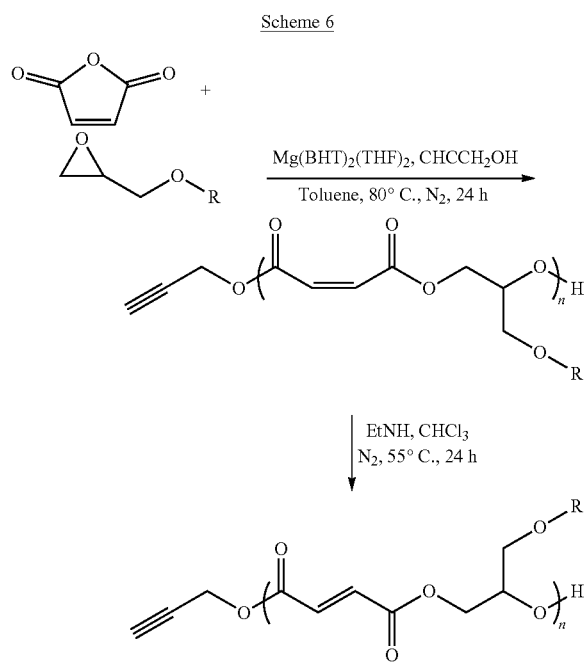

where R is a functional group, or an alkyl or aryl group containing a functional group, that is capable of entering into a "click" or other reaction with a corresponding functional group on a bioactive compound (i.e. bioactive drugs, peptides, proteins, sugars, etc.), functional species, or other compound to be added to the PPF polymer.

In one or more embodiments of the method of the present invention, a functionalized propylene oxide as described above is first prepared. Next, the functionalized propylene oxide, an initiating alcohol as described above, such as benzyl alcohol, propargyl alcohol, 4-hydroxybutan-2-one, or 5-norbonen-2-ol, a metal catalyst such as $Mg(BHT)_2(THF)_2$, and maleic anhydride are dissolved into a suitable solvent such as toluene or hexane using standard Schlenk line techniques. In various embodiments, the initiating alcohol may or may not be a functionalized initiating alcohol. In some of these embodiments, the total monomer concentration of the solution is from about 1M to about 6M, in other embodiments, from about 1M to about 5M, in other embodiments, from about 1M to about 4M, in other embodiments, from about 1M to about 3M, in other embodiments, from about 2M to about 6M, in other embodiments, from about 3M to about 6M, and in other embodiments, from about 4M to about 6M.

In various embodiments, the functionalized propylene oxide will comprise from about 30 mole percent to about 50 mole percent of the total propylene oxide monomer (i.e., the total combined moles of functionalized propylene oxide and propylene oxide) being used. In some embodiments, the functionalized propylene oxide will comprise from about 35 mole percent to about 50 mole percent of the total monomer, in other embodiments from about 40 mole percent to about 50 mole percent, in other embodiments from about 45 mole percent to about 50 mole percent, in other embodiments from about 30 mole percent to about 45 mole percent, in other embodiments from about 30 mole percent to about 40 mole percent, and in other embodiments from about 30 mole percent to about 35 mole percent of the total propylene oxide monomer (i.e., the total combined moles of functionalized propylene and propylene oxide) being used. The maleic anhydride will comprise about 50 mole percent of the total monomer (i.e., the total combined moles of functionalized propylene oxide, propylene oxide and maleic anhydride) being used.

In one or more of these embodiments, the reaction vessel is sealed and heated to a temperature of from about 40° C. to about 80° C. for from about 1 hours to about 48 hours (or until essentially all of the monomer is consumed) to produce the cis isomer (functionalized poly(propylene maleate)) intermediate of the functionalized PPF polymer of the present invention. In some embodiments, the reaction vessel is heated to a temperature of from about 40° C. to about 75° C., in other embodiments, from about 40° C. to about 70° C., in other embodiments, from about 40° C. to about 65° C., in other embodiments, from about 40° C. to about 60° C., in other embodiments, from about 50° C. to about 80° C., in other embodiments, from about 55° C. to about 80° C., and in other embodiments, from about 60° C. to about 80° C. In some embodiments, the reaction vessel is heated for from about 1 hours to about 50 hours, in other embodiments, from about 1 hours to about 36 hours, in other embodiments, from about 1 hours to about 30 hours, in other embodiments, from about 1 hours to about 24 hours, in other embodiments, from about 6 hours to about 48 hours, in other embodiments, from about 12 hours to about 48 hours, and in other embodiments, from about 24 hours to about 48 hours. The poly(propylene maleate) intermediary may be recovered by any suitable method known in the art for that purpose. In some of these embodiments, functionalized poly(propylene maleate) intermediary is recovered by precipitation in a suitable organic solvent such as diethyl ether.

In one or more of these embodiments, this functionalized poly(propylene maleate) intermediary is then isomerized to form the functionalized PPF polymer of the present invention. In these embodiments, the recovered functionalized poly(propylene maleate) intermediary is then dissolved in a suitable organic solvent, preferably chloroform, and an organic base, such as diethylamine or pyridine is added. The resulting solution is then heated to reflux temperature under an inert atmosphere for from about 1 hours to about 50 hours (or until substantially all of the poly(propylene maleate) intermediary has isomerized) to produce the functionalized PPF polymer of the present invention. In some embodiments, the solution is refluxed for from about 1 hours to about 36 hours, in other embodiments, from about 1 hours to about 30 hours, in other embodiments, from about 1 hours to about 24 hours, in other embodiments, from about 6 hours to about 48 hours, in other embodiments, from about 12 hours to about 48 hours, in other embodiments, from about 18 hours to about 48 hours, in other embodiments, from about 24 hours to about 48 hours, and in other embodiments, from about 36 hours to about 48 hours to produce the functionalized PPF polymer of the present invention.

The functionalized PPF polymer may be purified by any suitable method known in the art for that purpose. In some of these embodiments, functionalized PPF polymer is purified by repeated washing in an excess of phosphate buffer saline solution or a suitable acid solution, combining the organic layers as described above, and drying the resulting polymer in vacuo to produce the purified polymer.

To further define and reduce embodiments of the present invention to practice, three different "click" reactions capable functional groups were selected to functionalize the monomer precursors and were prepared as set forth in the Examples section below. The first functional group was the alkyne group that allows a 1,3-dipolar cycloaddition. The second one was the carbonyl group, which can undergo an oxime ligation reaction. The last one was hydroxyl group, which can adjust PPF hydrophilicity and form hydrogen bond, with potential for further functionalization.

Characterization of Functionalized Propylene Oxide Comonomers

1. Glycidyl Propargyl Ether (GPE)

Figure 18:
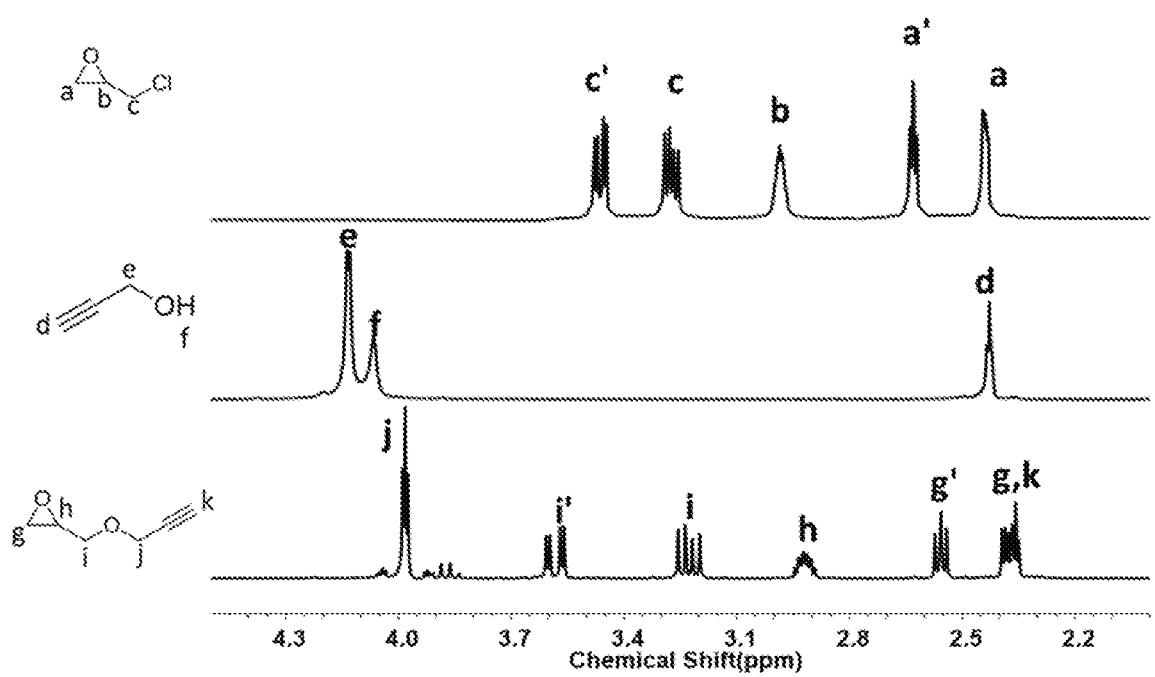
FIG. 18 is a $^1$H NMR spectra of glycidyl propargyl ether (lower), propargyl alcohol (middle) and epichlorohydrin (upper).

Glycidyl propargyl ether (GPE) was synthesized using a phase transfer reagent (i.e. tetrabutylammonium hydrogensulfate) to transfer propargyl alcohol from $H_2O$ to hexanes. (See Example 18) After purification, the pure product was characterized by $^1H$ NMR spectroscopy, and the data was compared with the starting materials in order to prove the chemical structure of the product. Comparison of the $^1H$ GPE NMR spectroscopic data for GPE with that of the starting materials shows that the epoxy ring and alkyne functionalities remain intact (FIG. 18). Moreover, $^1H$-$^1H$ COSY NMR spectroscopic data shows that five proton resonances from the epoxy structure are coupling, resulting in complex Gauche coupling.

2. 2-[[(2-nitrophenyl)methoxy]methyl]oxirane (NMMO)

Figure 19:
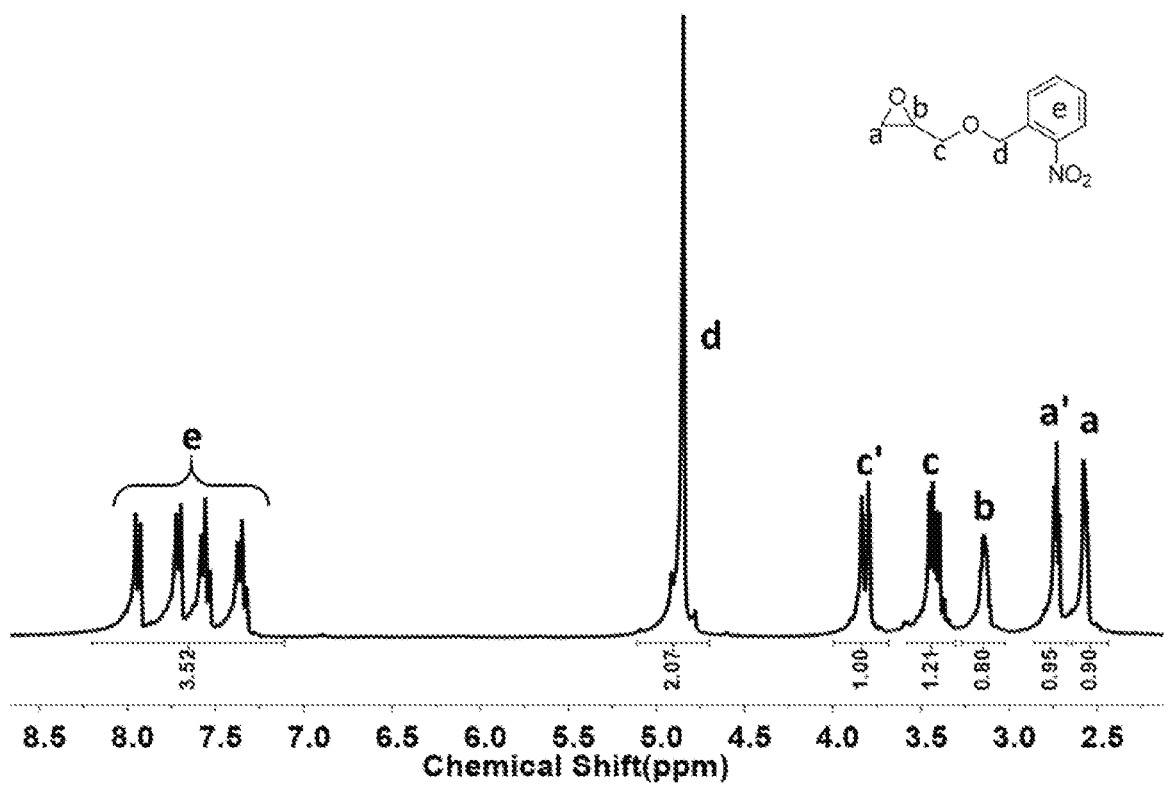
FIG. 19 is a $^1$H NMR spectrum of 2-[[(2-nitrophenyl)methoxy]methyl]oxirane.

In these experiments, 2-[[(2-Nitrophenyl)methoxy]methyl]oxirane was synthesized by using NaOH as a Lewis base to form the ether linkage with (±)-epichlorohydrin. After purification, the final product $^1H$ NMR spectroscopic data shows that the o-nitrobenzyl group successfully attached with the epoxide structure, with no ring-opening or other adverse side reactions (FIG. 19).

Characterization of the Monomer Functionalized PPM Polymer Intermediate.

1. Poly(glycidyl propargyl ether-co-maleic anhydride) (poly(GPE-co-MA))

Poly(glycidyl propargyl ether-co-maleic anhydride) was synthesized by ring-opening copolymerization of glycidyl propargyl ether and maleic anhydride. After precipitation and isomerization, the trans-configuration poly(GPE-co-MA) was characterized by $^1H$ and $^{13}C$ NMR spectroscopies, the molecular weight distribution was characterized by MALDI-ToF MS and SEC.

Figure 20:
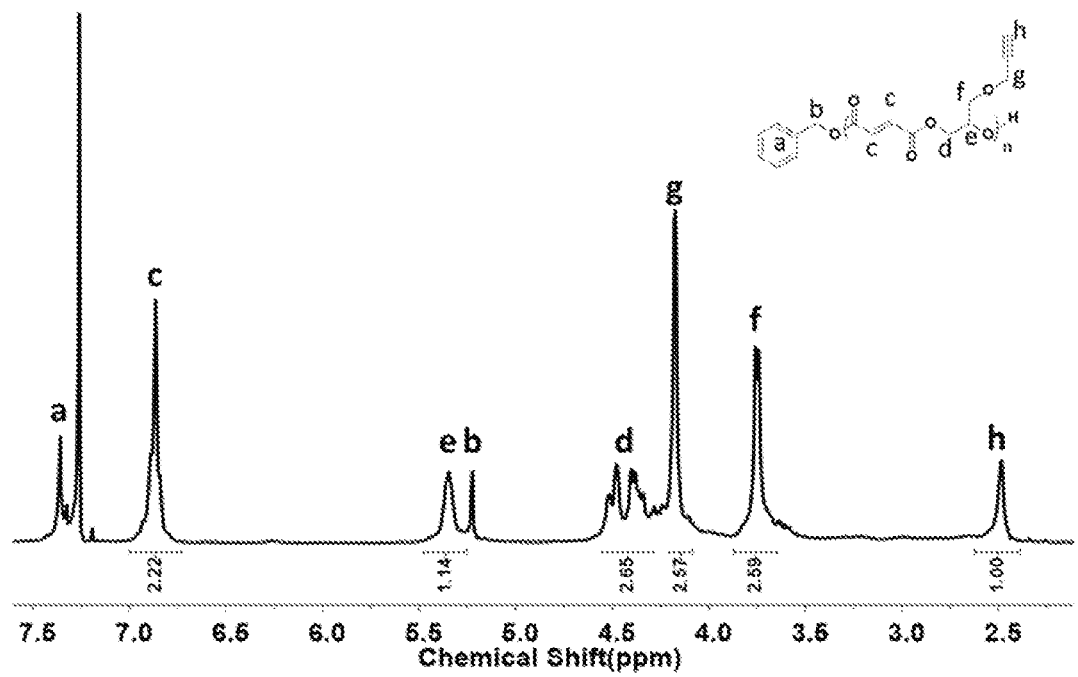
FIG. 20 is a $^1$H NMR spectrum of trans-poly(glycidyl propargyl ether-co-maleic anhydride).
Figure 21:
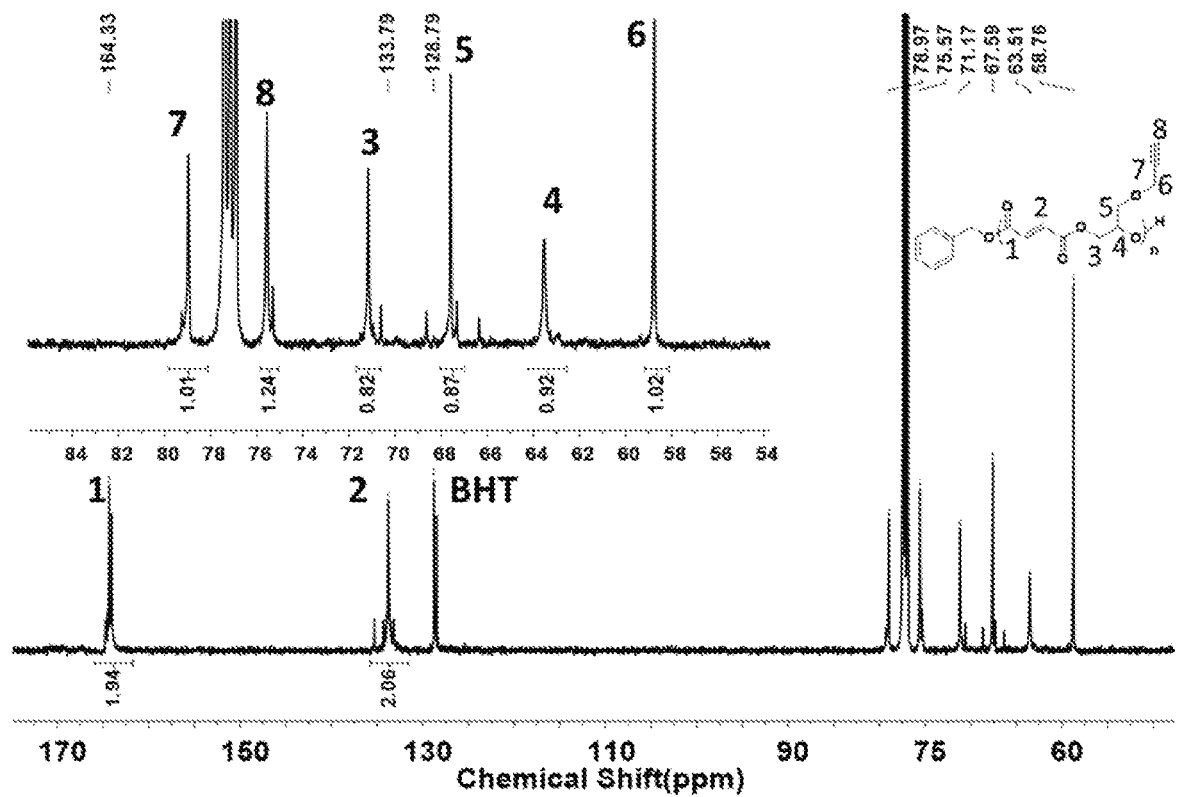
FIG. 21 is a quantitative $^{13}$C NMR spectrum of trans-poly(glycidyl propargyl ether-co-maleic anhydride).

Based on MALDI-ToF MS data, the regular molecular weight loss (210.10 Da) between near peaks is the same as polymer repeat unit's molecular weight, which proves that functionalized PPF has been obtained; Similarly, the $^1H$ NMR spectrum shows six different proton resonances, which corresponding to six different protons in the repeat unit (FIG. 20). The $^{13}C$ NMR spectrum of the resultant PPF shows carbon resonances from maleic anhydride comonomer and functionalized epoxide comonomer (FIG. 21), which means that alternating copolymer has been obtained.

In order to test how much control this system can have, four different target DP polymerizations were tested based on comonomers and catalyst feed ratio. During the same reaction conditions, the results show that when the target DP is around 25, the polymerization can target a specific DP with good accuracy (Table 4). Meanwhile, if the target DP is above 25, the system will lose control eventually as a consequence of poor polymer solubility, and a target DP that is below 25 can be controlled. The SEC results show that even if the system loses control, the polymer dispersity of target DP 50 is still good when compared to traditional transesterification method. It implies that ROP with catalyst has internal properties for controlling the polymerization precisely.

TABLE 4

Copolymerization of glycidyl propargyl ether and maleic anhydride with different target degree of polymerization

| Target $DP^a$ | $DP^b$ | Time (h) | Temperature (° C.) | Conversion (%) | $M_n^c$ (kDa) | $M_w^c$ (kDa) | $Đ_M$ |
|---|---|---|---|---|---|---|---|
| 10 | 7.4 | 24 | 80 | 47 | 4.2 | 5.3 | 1.3 |
| 25 | 21.1 | 24 | 80 | 52 | 7.6 | 10.6 | 1.4 |
| 50 | 18.7 | 24 | 80 | 55 | 7.6 | 12.2 | 1.6 |
| 100 | 43.7 | 24 | 80 | 25 | 10.8 | 26.4 | 2.4 |

$^a$DP is degree of polymerization;
$^b$detected by $^1H$ NMR;
$^c$detected by SEC.

2. poly(2-[[(2-nitrophenyl)methoxy]methyl]oxirane-co-maleic anhydride) (poly(NMMO-co-MA))

Figure 22:
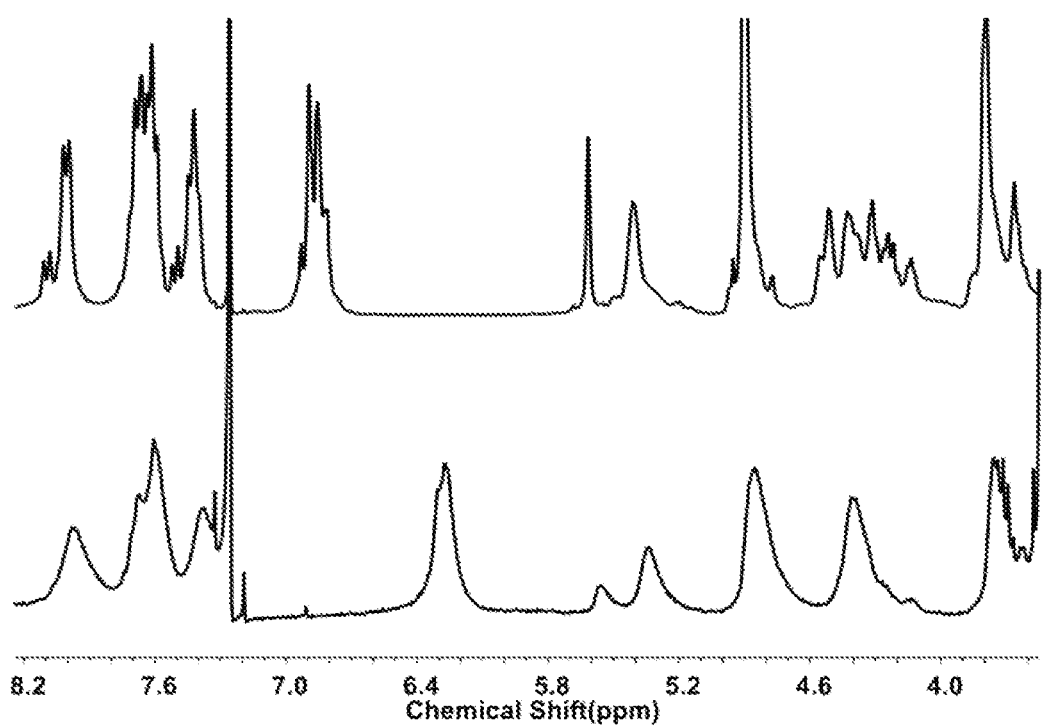
FIG. 22 is a $^1$H NMR spectra of poly(2-[[(2-nitrophenyl)methoxy]methyl]oxirane-co-maleic anhydride) before (bottom) and after (top) isomerization.

Poly(2-[[(2-nitrophenyl)methoxy]methyl]oxirane-co-maleic anhydride) synthesis was conducted in an analogous method to poly(GPE-co-MA). (See Example 19, below) In order to determine the degree of isomerization of the alkene group during reflux in $CHCl_3$ with diethylamine (0.15 mol. equiv. per alkene), $^1H$ NMR spectra of polymers before and after isomerization were used. As observed in the NMR spectra before and after isomerization, there is a clear change in the chemical shift of proton resonances from the alkene group after isomerization (δ=6.27 ppm to δ=6.89 ppm), which is related to cis to trans configuration change (FIG. 22). This process is similarly displayed during isomerization of poly(GPE-co-MA).

Figure 23:
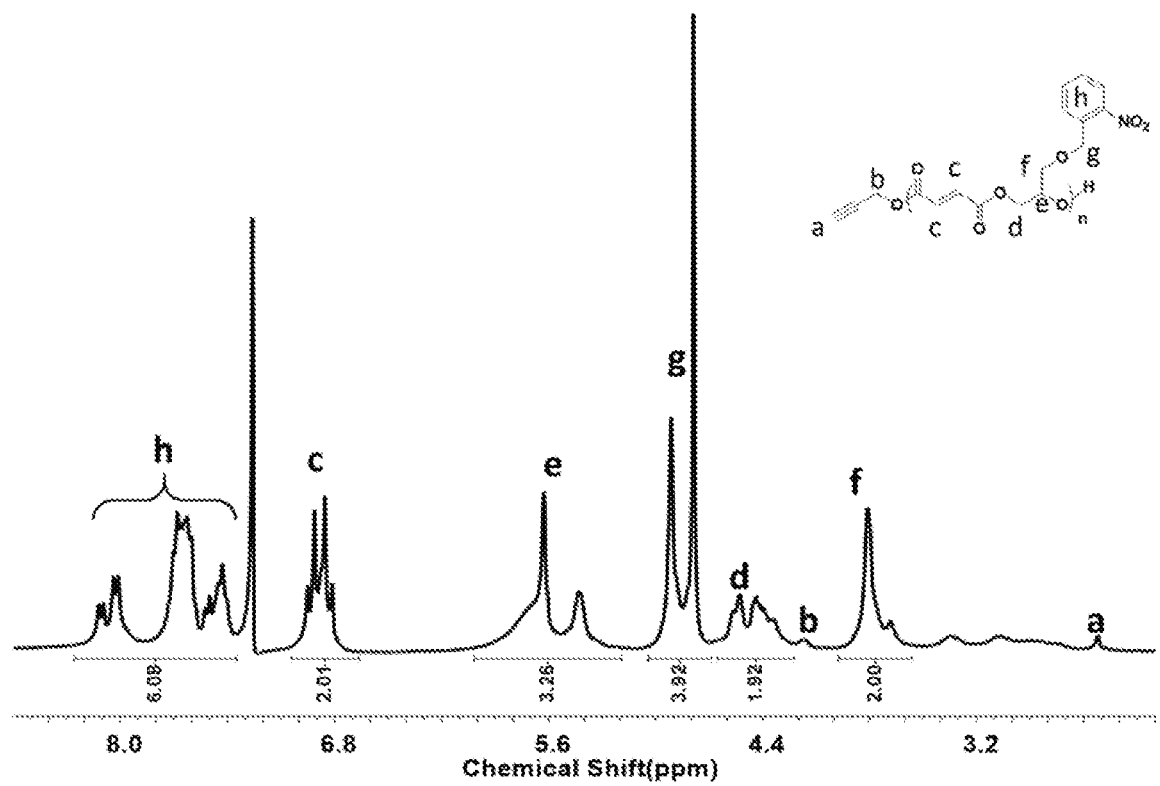
FIG. 23 is a $^1$H NMR spectrum of trans-poly(2-[[(2-nitrophenyl)methoxy]methyl]oxirane-co-maleic anhydride).
Figure 24:
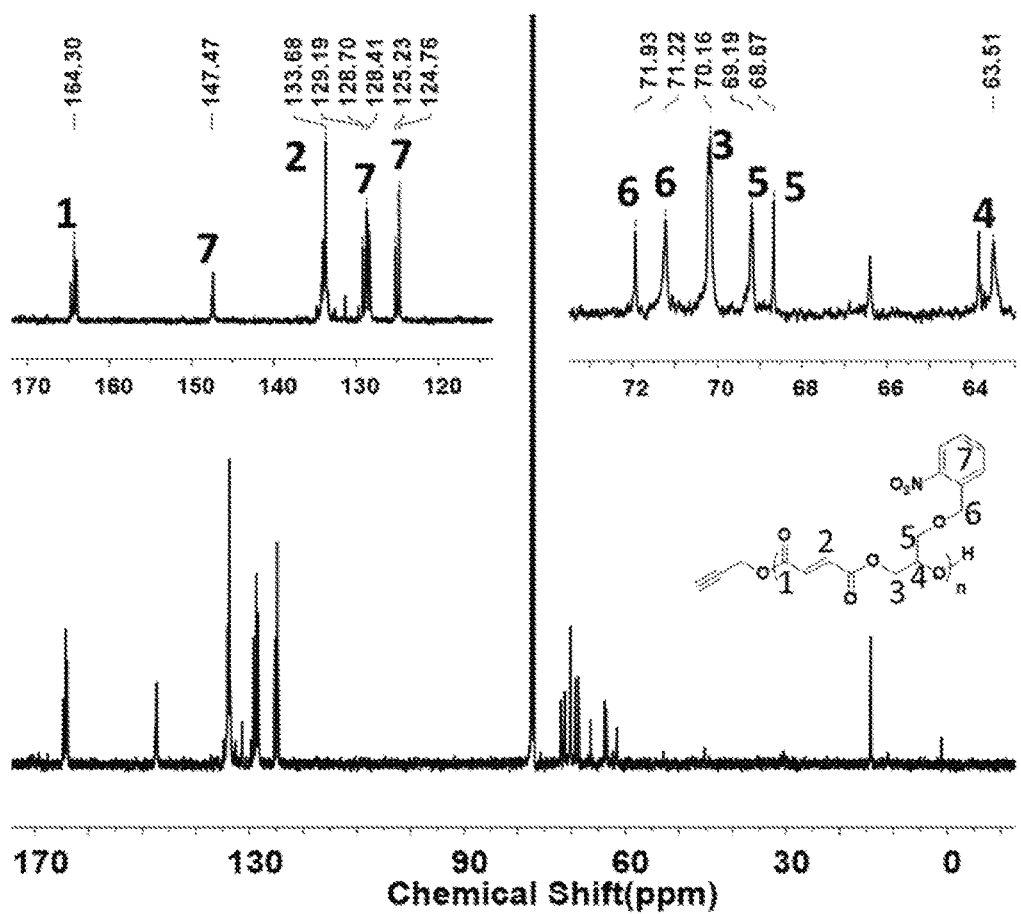
FIG. 24 is a $^{13}$C NMR spectrum of trans-poly(2-[[(2-nitrophenyl)methoxy]methyl]oxirane-co-maleic anhydride).

Moreover, the MALDI-ToF MS data shows high endgroup fidelity for poly(NMMO-co-MA) through only polymers initiated by propargyl alcohol being produced, which means the catalyst employed is able to tolerate different epoxides without undesirable side reactions. The equal weight loss of every near two peaks (307.21 Da) and clear $^1H$, $^{13}C$ NMR spectra proves that the functionalized chemical structure exists (FIGS. 23-24).

Through SEC analysis, the number average molecular weight ($M_n$) of poly(NMMO-co-MA) was determined to be ca. 2.6 KDa, the weight average molecular weight ($M_w$) was determined to be 2.7 KDa, resulting in a dispersity WO of 1.04. For controlled polymerization, the ideal dispersity is unity, the SEC result shows that the dispersity of poly (NMMO-co-MA) is very close to the ideal dispersity, which means the successful control of this polymerization is achieved.

The other perfect properties for NMMO and MA copolymerization proved by $^1$H NMR spectroscopic data is that the copolymerization of NMMO and MA shows high conversion (99%) and the DP is almost identical to the target DP (i.e. 25). The possible reason is that the side group nitrobenzyl modifies solubility of polymer in reaction solvent (i.e. toluene), which corresponds to less solid precipitation during the polymerization. When other epoxides are used poor solubility or low boiling point of the monomer can severely affect the rate of polymerization. For example, propylene oxide boils at 34° C. and consequently can boil out of solution during the polymerization. (See FIG. 24)

Kinetic Study of Polymerization

Pseudo-first order kinetic studies were conducted in order to understand the copolymerization process and the influence of different functionalized monomers during copolymerization further. Here the two types of epoxide monomer synthesized were studied, with the kinetic study showing differences between the rate of copolymerization between GPE and NMMO.

Figure 25:
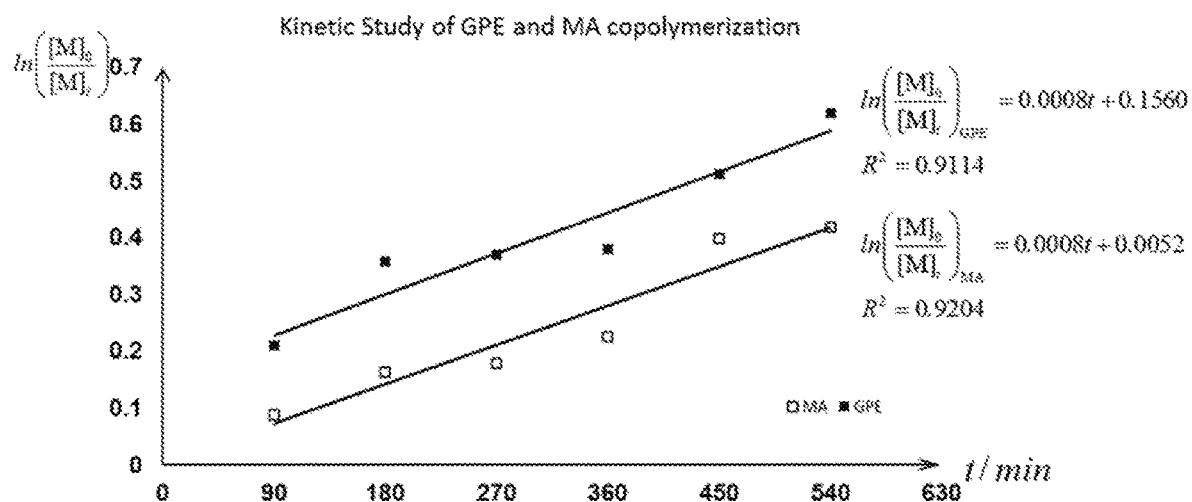
FIG. 25 is a short term kinetic study plot of copolymerization of glycidyl propargyl ether (GPE) and maleic anhydride (MA).
Figure 26:
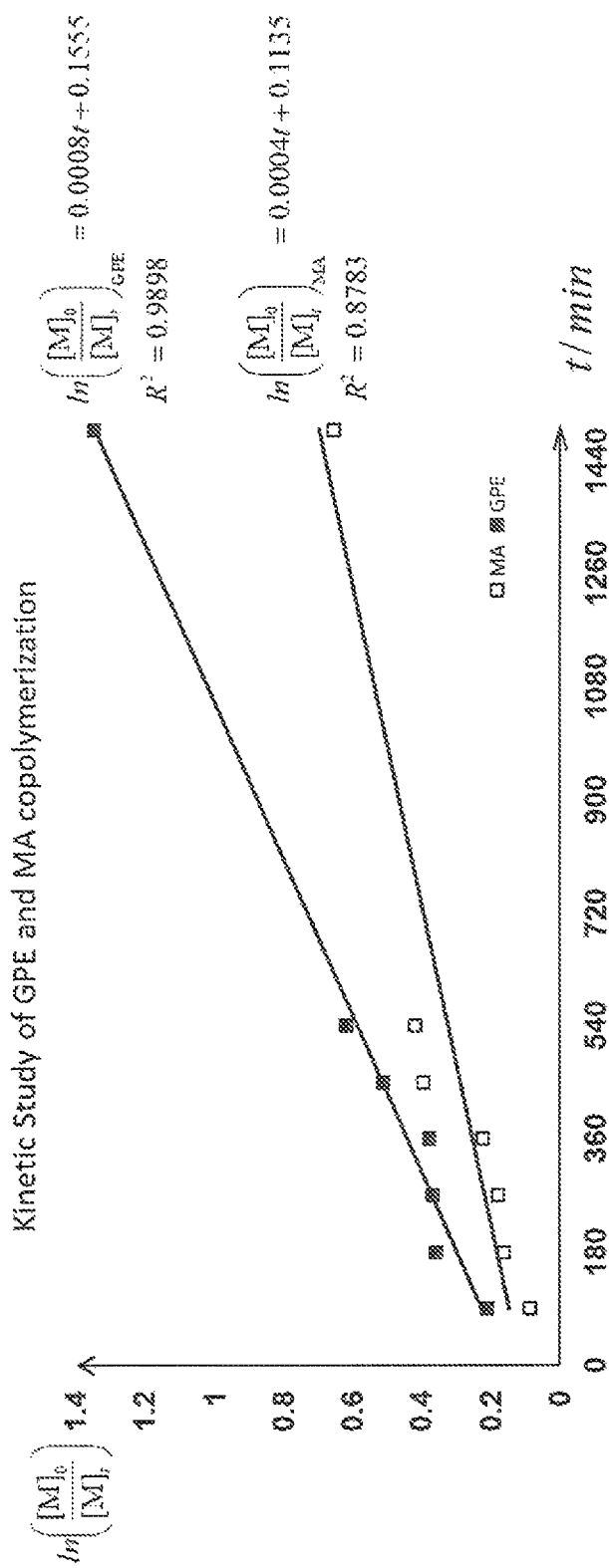
FIG. 26 is a long term kinetic study plot of copolymerization of glycidyl propargyl ether (GPE) and maleic anhydride (MA).

1. Kinetic Study for Copolymerization of Glycidyl Propargyl Ether and Maleic Anhydride For the copolymerization of GPE and MA, the rate of monomer consumption of GPE and MA are similar, indicating that these two monomers undergo alternating copolymerization very well (FIG. 25); however, if long term polymerizations are considered, the GPE propagation rate is faster than MA propagation rate (FIG. 26), which can be explained by end-group analysis of MALDI-ToF MS data. Based on MALDI-ToF MS data, there is a small amount of polymer chains that end with GPE wherein the ether attachment has been removed via a chain scission side reaction. These GPE end-groups are responsible for higher conversion and faster consumption rate during a relatively long term. (See Table 5)

TABLE 5

Conversion and $\ln([M]_0/[M]_t)$ of glycidyl propargyl ether (GPE) and maleic anhydride (MA) based on $^1$H NMR spectroscopy$^a$

| t/min | Conversion GPE (%) | Conversion MA (%) | $\ln([M]_0/[M]_t)_{GPE}$ | $\ln([M]_0/[M]_t)_{MA}$ |
|---|---|---|---|---|
| 90 | 19 | 8 | 0.21 | 0.09 |
| 180 | 30 | 15 | 0.36 | 0.16 |
| 270 | 31 | 16 | 0.37 | 0.18 |
| 360 | 32 | 20 | 0.38 | 0.22 |
| 450 | 40 | 33 | 0.51 | 0.40 |
| 540 | 46 | 34 | 0.62 | 0.42 |
| 1490 | 74 | 48 | 1.35 | 0.66 |

$^a$The reaction condition is 80° C., under N$_2$, using toluene as solvent and benzyl alcohol as initiator.

2. Kinetic Study for Copolymerization of 2-[[(2-nitrophenyl)methoxy]methyl]oxirane and Maleic Anhydride

TABLE 6

Conversion and $\ln([M]_0/[M]_t)$ of 2-[[(2-nitrophenyl)methoxy]methyl]oxirane (NMMO) and maleic anhydride (MA) based on $^1$H NMR spectroscopy$^a$

| T (min) | Conversion NMMO (%) | Conversion MA (%) | $\ln([M]_0/[M]_t)_{NMMO}$ | $\ln([M]_0/[M]_t)_{MA}$ |
|---|---|---|---|---|
| 90 | 9 | 4 | 0.10 | 0.04 |
| 180 | 18 | 7 | 0.20 | 0.07 |
| 270 | 22 | 10 | 0.25 | 0.10 |
| 360 | 25 | 13 | 0.29 | 0.14 |
| 450 | 28 | 17 | 0.33 | 0.18 |
| 540 | 30 | 18 | 0.36 | 0.20 |

$^a$The reaction condition is 80° C., under N$_2$, using toluene as solvent and propargyl alcohol as initiator.

Figure 27:
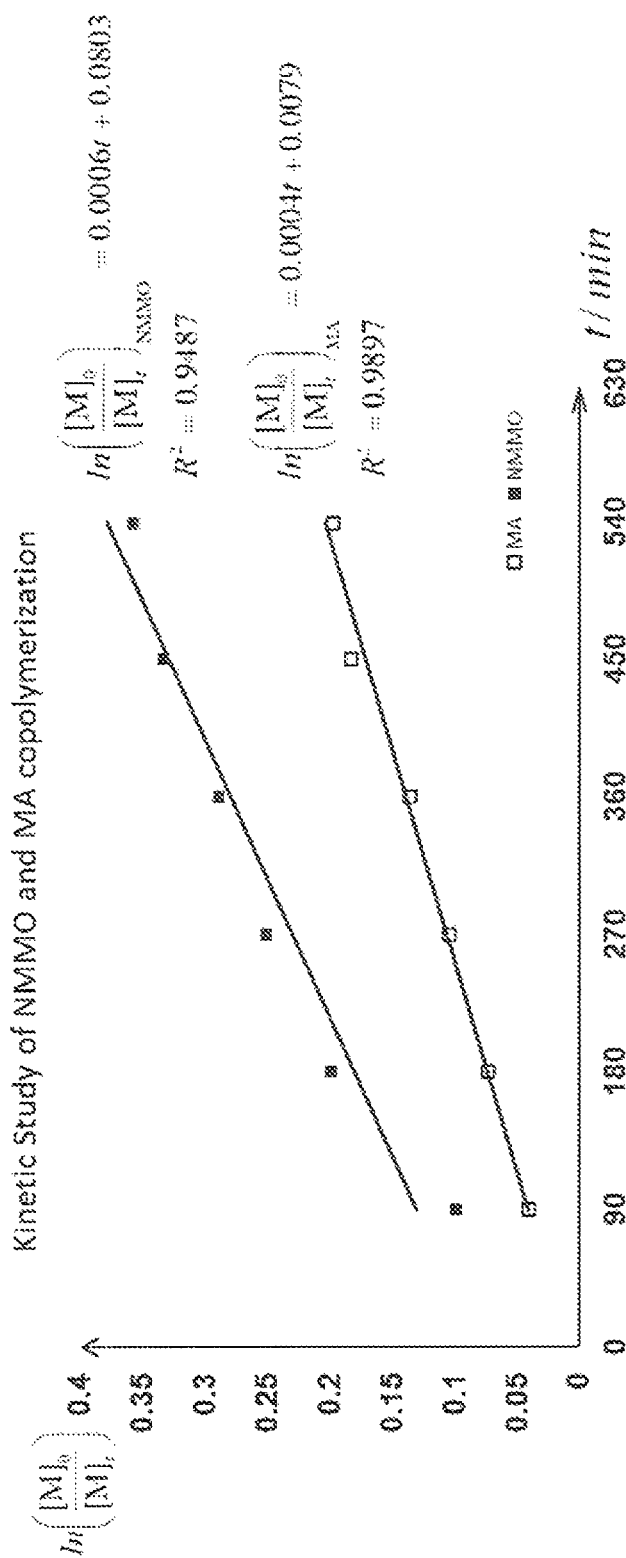
FIG. 27 is a kinetic study plot of copolymerization of 2-[[(2-nitrophenyl)methoxy]methyl]oxirane (NMMO) and maleic anhydride (MA).

For copolymerization of NMMO and MA, the propagation rate of NMMO is more rapid than the rate of MA consumption (Table 6; FIG. 27). Compared against the rate of propagation for the copolymerization of GPE and MA, the propagation rate of NMMO will be faster than the propagation of MA, resulting in polymer chains that have more NMMO repeat unit, and the copolymerization may not be strictly an alternating copolymerization. According to end-group analysis of MALDI-ToF MS data, this phenomenon can also be explained through the majority of polymer chains having two sequential NMMO as the end-group (FIG. 24).

Discussion of Other Monomers Synthesis Processes

As set forth above, the functionalization of poly(propylene fumarate) via monomer functionalization has been successfully realized. Based on the blueprint for small molecule attachment through etherification reactions, the synthesis of a carbonyl functionalized epoxide was attempted because the carbonyl group has a potential to undergo "click" type oxime reactions and other effective organic reactions. Considering the chemical properties of epoxides, the successful synthesis of a functionalized monomer must prevent ring-opening of the epoxides, hence phase transfer reactions that separate epoxides from active Lewis bases that has been used to synthesis GPE were selected. However, it was found that the phase transfer reaction does not work well for the carbonyl to epoxide addition synthesis.

As shown above, the functionalization of PPF with alkyne and o-nitrobenzyl groups was realized, which resulted in two new comonomers, glycidyl propargyl ether (GPE) and 2-[[(2-nitrophenyl)methoxy]methyl]oxirane (NMMO), respectively. The $^1$H and $^1$H-$^1$H COSY NMR spectroscopic data show the successful synthesis of both GPE and NMMO. The $^1$H and $^{13}$C NMR spectroscopic results prove that after copolymerization of maleic anhydride and a functionalized comonomer, functionalized PPF is obtained, which is further supported by MALDI-ToF MS data. MALDI-ToF MS data has also shown high end-group fidelity for both types of functionalized PPF. The SEC data shows that the two functionalized PPF variants have low disparities. Moreover, based on kinetic study data, the ring-opening copolymerization with a magnesium catalyst is a controlled polymerization, with no chain transfer and no termination side reactions occurring during polymerization. Different functionalized comonomer were observed to have different propagation rates. The functionalized PPF are able to undergo printing using stereolithographic techniques, and their scaffolds have the ability to undergo surface modification which can enhance PPF molecular interaction with cells.

Methods for Making Functionalized PPF Scaffolds or Other Structures

In yet another aspect, the present invention is directed to methods of making the functionalized PPF scaffold and other polymer structures described above comprising the functionalized PPF polymers described above. As set forth above, the functionalized FFP polymers of the present invention are well suited for use in resins for 3D printing. In one or more embodiments, 3D scaffolds or other polymer structures using a resin formed with the functionalized PPF in a previously reported composition. See, Luo, Y.; Dolder, C. K.; Walker, J. M.; Mishra, R.; Dean, D.; Becker, M. L., *Biomacromolecules*, 2016, 17, 690-697, the disclosure of which is incorporated herein in its entirety. Briefly, functionalized PPF is dissolved into an equal mass of diethyl fumarate (DEF) and a mixture of photoinitiators and light scattering agents (4.1 wt. %) were mixed evenly throughout the resin. The resin is then printed using convention stereolithography techniques or cDLP methods and photocrosslinked to form functionalized PPF polymer structures.

In one or more embodiment, PPF polymers according to the present invention having higher number average molecular weights (about 4000 Da or more) may be formed into functionalized PPF scaffold and other polymer structures using conventional techniques such as electrospinning, extrusion, or molding and then photochemically crosslinked. One of ordinary skill in the art would be able to construct functionalized PPF scaffold and other polymer structures from these polymers without undue experimentation.

Methods for Attaching Functional Species to the Functionalized PPF Scaffolds/Structures In yet another aspect, the present invention is directed to methods of attaching bioactive materials or other functional species to the functionalized PPF polymers described above. In some of these embodiments, the functional group added to the PPF polymer as described above is selected to bond to a corresponding functional group on the bioactive materials or other functional species to be added to the polymer. As will be apparent, the bioactive materials or other functional species must have, or be functionalized to have, an available functional group to bond with the functional group on the PPF polymer as described above and it must do so in such a way that neither bonding with, nor being functionalized to bond with, the functionalized PPF polymers described above destroys or unduly inhibits the desirable properties or uses for which the bioactive materials or other functional species were to be attached.

As set forth above, to be attached, the bioactive materials or other functional species must contain a functional group/moiety capable of bonding to one or more the functional group on the functionalized PPF polymers of the present invention. In one or more embodiments, the bioactive materials or other functional species will naturally contain a function group/moiety capable of bonding to one or more the functional group on the functionalized PPF polymers of the present invention, without destroying or unduly inhibiting the desirable properties or uses for which is to be attached. As will be apparent, the functional group/moieties capable of bonding to one or more the functional group on the functionalized PPF polymers of the present invention must be present be must be located in an area of the bioactive compound of other functional species that is free to interact with a functional group on the functionalized PPF polymers of the present invention. Examples these functionalized bioactive materials or other functional species may include, without limitation, peptides, oligomers, or proteins having cysteine residues with available thiol groups; peptides, oligomers, or proteins having, or being functionalized to have, thiol functional groups; peptides, oligomers, or proteins having, or being functionalized to have, alkene or allyl functional groups; peptides, oligomers, or proteins having, or being functionalized to have, alkyne or propargyl functional groups; peptides, oligomers, or proteins having, or being functionalized to have, azide functional groups (See, e.g. Scheme 3, Example 14); peptides, oligomers, or proteins having, or being functionalized to have, a ketone or amine functional group; peptides, oligomers, or proteins having, or being functionalized to have, a hydroxyl group or protected hydroxyl functional group; peptides, oligomers, or proteins having, or being functionalized to have, a cyclooctyne or 4-dibenzyocyclooctyne functional group; alkyl or aryl groups including a fluorescent atom or compound or other marker and having, or being functionalized to have, a alkyne group, an alkene group, a hydroxyl group, a protected hydroxyl group, thiol group, or halide group; and short chain dyes having, or being functionalized to have, a alkyne group, an alkene group, a hydroxyl group, a protected hydroxyl group, thiol group, or halide group (See, e.g., Example 13).

In some other embodiments, however, the bioactive materials or other functional species to be attached either has no available functional groups all or no functional groups suitable for attachment to functional group on the functionalized PPF polymers of the present invention. In these embodiments, the bioactive materials or other functional species to be attached must be functionalized or otherwise modified to include a suitable functional group. As used herein, a "suitable" functional group or moiety is a functional group or moiety that is cable of bonding with a corresponding functional group/moiety on the other of the functionalized PPF polymer or bioactive material/functional species being attached, preferably via a click reaction. As will be apparent, the specific mechanism for functionalizing the bioactive material or other functional species to be attached will depend upon the particular material being attached, as well as the range of functional groups that will bond with the functional group or groups on the functionalized PPF polymers to which it is to be attached. In one or more embodiments, functional groups may be added to the bioactive materials or other functional species to be attached as shown in Scheme 3, above. One of ordinary skill in the art will be able to attach a suitable functional group/moiety to the bioactive or other functional species to be attached without undue experimentation.

While not required to practice the present invention, the functional groups on the functionalized PPF polymers and the bioactive materials or other functional species being attached thereto, should be selected to take advantage of any one of the many "click" reactions described above. As set forth above, known "click" reactions are preferred for this purpose because they are known to be modular, wide in scope, stereospecific, give very high yields, generate minimal byproducts that can be removed by non-chromatographic methods, such as recrystallization or distillation, insensitive to oxygen and water, to use readily available starting materials and reagents, and use solvents that are benign or easily removed, if any.

Examples of click reactions that are particularly useful for this purpose are thiolene reactions between thiol and alkene functional groups, thiolyne reactions between thiol and alkyne functional groups, 1,3-dipolar cycloaddition reactions between alkyne and azide functional groups, and/or oxime ligation reactions between ketone and amine functional groups between the functional group/moiety of the bioactive or other functional species and a functional group on the functionalized PPF polymers of the present invention, but many other suitable combinations are possible and within the scope of the invention. For example, if the functional group/moiety of the bioactive material or other functional species is a thiol group, then the functional group on the functionalized PPF polymers of the present invention could be an alkene group or an alkyne group. In this example, the bioactive material or other functional species could be attached by a thiolene reaction between thiol and alkene functional groups or a thioyne reaction between thiol and alkyne functional groups. Similarly, if the functional group on the functionalized PPF polymers of the present invention is an alkyne group, then a bioactive material or other functional species having, or having been functionalized to have, an alkyne or an azide the functional group/moiety could be used. In these embodiments, the bioactive material or other functional species could be attached by a thioyne reaction between the thiol and alkyne functional groups or a 1,3-dipolar cycloaddition reactions between alkyne and azide functional groups.

In some of these embodiments, the functional group on the PPF polymer as described above is actually a protecting group or other intermediate and must be removed or modified before the reaction to add the bioactive materials or other functional species can proceed. For example, in some of these embodiments, the functional group added to the PPF polymer as described above is a halide group such as the halide group on (±)-epichlorohydrin or a nitrobenzyl group such as 2-[[(2-nitrophenyl)methoxy]methyl]oxirane (NMMO). In these embodiments, the nitrobenzyl group on NMMO is a UV sensitive protecting group, which can easily be replaced with a hydroxyl group upon exposure to specific UV wavelengths and the halide group on (±)-epichlorohydrin is a protecting group, which is later replaced with any suitable nucleophile. Suitable nucleophiles may include without limitation, amines, alcohols, thiols and hydroxylamines.

In some embodiments, the poly(propylene fumarate) polymer of the present invention may having the formula:

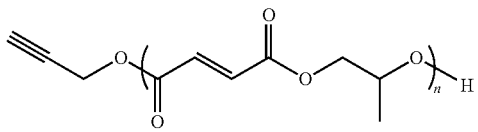

wherein n is defined as above. In one or more of these embodiments, a bioactive compound or other functional species, such as a peptide, short chain peptide, protein, short chain dye, drug, or marker functionalized that has been functionalized with an azide molecule may be added to the end propargyl functional group by means of a 1,3 Huisgen cycloaddition click reaction as discussed above.

In some embodiments, the poly(propylene fumarate) polymer of the present invention may having the formula:

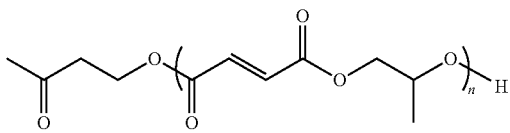

wherein n is defined as above. In these embodiments, a bioactive compound or other functional species, such as a peptide, short chain peptide, protein, short chain dye, drug, or marker that has been functionalized to include amine or hydroxylamine functional group, may be added to the end ketone functional group by means of a shiff base conjugation or oxime ligation click reaction.

In some embodiments, the poly(propylene fumarate) polymer of the present invention may having the formula:

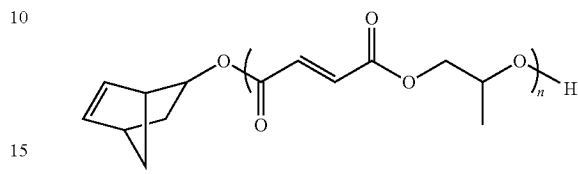

wherein n is defined as above. In one or more of these embodiments, a bioactive compound or other functional species, such as a peptide, short chain peptide, protein, short chain dye, drug, or marker that has been functionalized to include a thiol functional group may be added to the end norbornyl functional group by means of a thiolene click reaction.

In some embodiments, the functionalized PPF polymer of the present invention may have the formula:

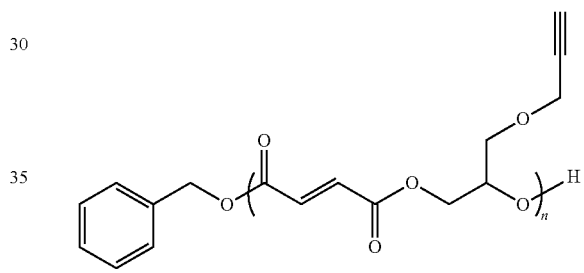

where n is an integer from about 1 to about 100. In these embodiments, a bioactive compound of other functional species, such as a peptide, short chain peptide, protein, short chain dye, drug, or marker, may be added to the propargyl functional group by means of a thiolyne click reaction.

In some other embodiments, the functionalized poly(propylene fumarate) polymer of claim 1 having the formula:

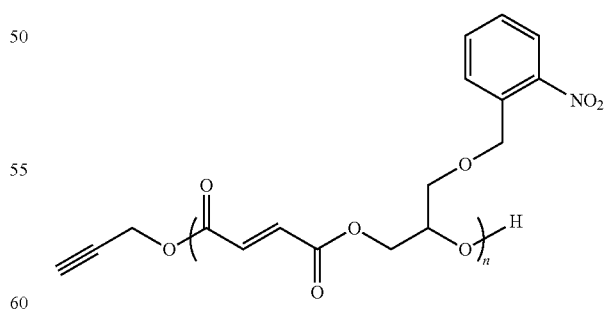

where n is an inter from about 1 to about 100. In these embodiments, the NMMO functional group may be cleaved using photochemistry to yield a free hydroxyl group, which can then be used as a functional group to react as a nucleophile to react with electrophiles or other suitable groups, such as acid halide compounds or activated esters.

In some other embodiments, the functionalized poly(propylene fumarate) polymer of claim 1 having the formula:

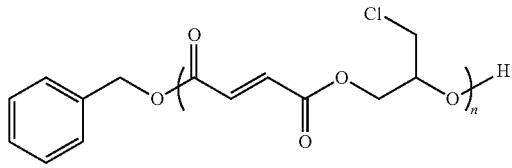

where n is an inter from about 1 to about 100. In these embodiments, a functional species, such as any nucleophile may be added to the chloryl group by means of a $S_{n2}$ displacement reaction. In various embodiments, suitable nucleophiles may include, without limitation, amines, alcohols, thiols and hydroxylamines.

In various embodiments, the functionalized PPF of the present invention has low dispersity, clear end-groups, and the polymerization is a controlled polymerization. These properties can be proved by $^1$H NMR spectroscopy, $^{13}$C NMR spectroscopy, SEC, MALDI-ToF mass spectrometry and kinetic study data. The successful synthesis of functionalized PPF means that there is an access to modify PPF chemical properties via functionalizing comonomers. Moreover once functionalized PPF scaffold shows some improved properties than PPF, this scalable functionalization method will provide a good pathway for modifying PPF chemical structure for different applications.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Abbreviations

BHT, 2,6-di-tert-butyl-4-methylphenoxide; cDLP, continuous digital light processing; CuAAC, copper-assisted azide-alkyne cycloaddition; DEF, diethyl fumarate; $Ð_M$, dispersity; DP, degree of polymerization; DSC, differential scanning calorimetry; FDM, fused deposition modeling; GPC, gel-permeation chromatography; I, initiator; MALDI-ToF MS, matrix-assisted laser desorption/ionization time-of-flight mass spectrometry; MAn, Maleic Anhydride; $M_n$, number average molecular mass; $M_w$, weight average molecular mass; NMR, nuclear magnetic resonance; PCL, poly(ε-caprolactone); PEU, poly(ester urea); PO, propylene oxide; PLLA, poly(L-lactic acid); PPF, poly(propylene fumarate); PPM, poly(propylene maleate); PU, poly(urethane); RI, refractive index; ROCOP, ring-opening copolymerization; ROP, ring-opening polymerization; SEC, size-exclusion chromatography; TEM, transmission electron microscopy; THF, tetrahydrofuran; 4HB, 4-hydroxybutan-2-one.

Materials for Examples 1 Through 17

All reagents were purchased from Millipore-Sigma except for 2,6-di-tert-4-methylphenol, which was purchased from Acros (Geel, Belgium). Mg(BHT)$_2$(THF)$_2$ was synthesized as previously reported. See, Wilson, J. A.; Hopkins, S. A.; Wright, P. M.; Dove, A. P., *Polym. Chem.*, 2014, 5, 2691-2694, the disclosure of which is incorporated herein by reference in its entirety. All solvents were purchased from Fisher and dried using an Innovative Technology Inc. Pure Solv MD-3 solvent purification system. Benzyl alcohol, propargyl alcohol, 4-hydroxybutan-2-one and propylene oxide were dried over calcium hydride for 24 h before vacuum distillation. Maleic anhydride was dried in vacuo over P$_2$O$_5$ for one week. All other reagents were used as received.

Instrumental Methods for Examples 1 Through 17

Proton ($^1$H) NMR spectra were recorded using a Varian Mercury 300 spectrometer. Carbon ($^{13}$C) NMR spectra were recorded using a Varian NMRS 500 spectrometer. All chemical shifts were recorded in parts per million (ppm) relative to the reference peak of chloroform solvent at δ=7.26 and 77.16 ppm for $^1$H and $^{13}$C NMR spectra, respectively. Molecular masses were determined through size exclusion chromatography (SEC) using a Tosoh EcoSEC HLC-8320GPC on TSKgel GMH$_{HR}$-M columns in series with refractive index (RI) detection. Molecular masses were calculated using a calibration curve determined from poly(styrene) standards with tetrahydrofuran (THF) as the eluent flowing at 1.0 mL min$^{-1}$ and a sample concentration of 10.0 mg mL$^{-1}$. MALDI-ToF mass spectra were recorded on a Bruker Ultra-Flex III MALDI-ToF/ToF mass spectrometer equipped with a Nd:YAG laser emitting at 355 nm. The instrument was operated in positive ion mode. All samples were dissolved in THF at a final concentration of 10 mg mL$^{-1}$. Trans-2-[3-(4-tert-butylphenyl)-2-methyl-2-propenylidene] malononitrile (DCTB) (20 mg mL$^{-1}$) served as a matrix and sodium trifluoroacetate (NaTFA) (10 mg mL$^{-1}$) as cationizing agent were prepared and mixed in the ratio 10:1. Matrix and sample solutions were applied onto the MALDI-ToF target plate by the sandwich method. FlexAnalysis software was used to analyze MALDI-ToF data. PPF films were printed using an Envisiontec™ Micro Plus Advantage® continuous digital light processing (cDLP) printer. Fluorescence microscopy was conducted on an Olympus IX81 Fluorescence Microscope with FITC and TRITC filters.

Example 1

Synthesis of End-Functionalized Poly(Propylene Maleate)PPM

General Method

Using standard Schlenk line techniques, an ampoule is filled with Mg(BHT)$_2$(THF)$_2$, an initiating alcohol, propylene oxide and maleic anhydride. The solution is dissolved into toluene to a total monomer concentration of 2 M. The ampoule is sealed and heated at 80° C. for a defined time period. The resultant polymer is recovered by precipitation in excess diethyl ether.

Example 2

Synthesis of End-Functionalized Poly Propylene Maleate

General Method with Hexane

Using standard Schlenk line techniques, an ampoule is filled with $Mg(BHT)_2(THF)_2$, an initiating alcohol, propylene oxide and maleic anhydride. The solution was dissolved into hexanes to a total monomer concentration of 2 M. The ampoule was sealed and heated at 45° C. for a defined time period. The solution is then decanted and the filtrate dissolved into chloroform. The resultant polymer is recovered by precipitation in excess diethyl ether.

Example 3

Synthesis of Benzyl Alcohol Initiated End-Functionalized Poly(Propylene Maleate

End-functionalized poly(propylene maleate) was synthesized using the method set forth in Example 1 using benzyl alcohol as the initiating alcohol and a magnesium catalyst as shown in Scheme 7, below and the using reaction parameters shown in Table 7, below.

Scheme 7
Copolymerization of maleic anhydride and propylene oxide initiated by benzyl alcohol and catalyzed by $Mg(BHT)_2(THF)_2$.

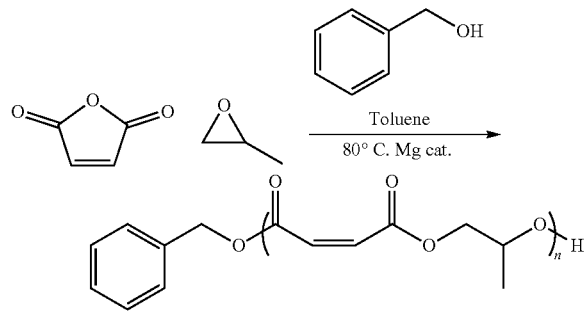

TABLE 7

| | | Benzyl alcohol initiated PPM | | | |
|---|---|---|---|---|---|
| [I]:[cat.] | [I]:[M] | T (° C.) | Time (h) | $M_n$ (kDa) | $Đ_M$ |
| 1:1 | 1:10 | 80 | 18 | 2.8 | 1.17 |
| 1:1 | 1:25 | 80 | 18 | 3.7 | 1.25 |
| 1:1 | 1:50 | 80 | 48 | 5.8 | 1.27 |
| 1:1 | 1:100 | 80 | 48 | 9.7 | 1.69 |

The presence of a benzyl terminated poly(propylene maleate) product was confirmed by $^1$H NMR (300 MHz, 303 K, DMSO-$d_6$): δ=7.37 (m, $C_6H_5$), 6.52-6.44 (m, OC(=O)H=CH(=O)O), 5.16-5.10 (m, $CH_2CH(CH_3)$O and ($C_6H_5$)$CH_2$O), 4.21-4.14 (m, $CH_2CH(CH_3)$O), and 1.30-1.15 (m, $CH_2CH(CH_3)$O) ppm (See FIG. 1); $^{13}$C NMR (125 MHz, 298 K, DMSO-$d_6$): δ=164.60 and 164.30 (MAn*-PO, OCOCH$_2$), 130.58 and 130.14 (MAn*-PO, O(O)C*CH=CH), 130.00 and 129.51 (MAn*-PO, O(O)C*CH=CH), 128.40 and 128.19 (aromatic $C_s$), 68.76 (MAn*-PO, OCH(CH$_3$)CH$_2$), 66.98 (MAn*-PO, OCH(CH$_3$)CH$_2$), 65.80 (($C_6H_5$)CH$_2$O) and 15.73 (PO, $CH_2$CH(CH$_3$)O) ppm; and size exclusion chromatography (SEC) (DMF): $M_n$=3.7 kDa, $M_w$=4.6 kDa, $Đ_M$=1.3. Yield=84%.

Example 4

Synthesis of Benzyl Alcohol Initiated End-Functionalized Poly(Propylene Maleate) Using Hexanes End-functionalized poly(propylene maleate) was synthesized using the method set forth in Example 2 above using benzyl alcohol as the initiating alcohol, hexane and a magnesium catalyst as shown in Scheme 8, below and using the reaction parameters shown in Table 8, below.

Scheme 8
Copolymerization of maleic anhydride and propylene oxide initiated by benzyl alcohol and catalyzed by $Mg(BHT)_2(THF)_2$.

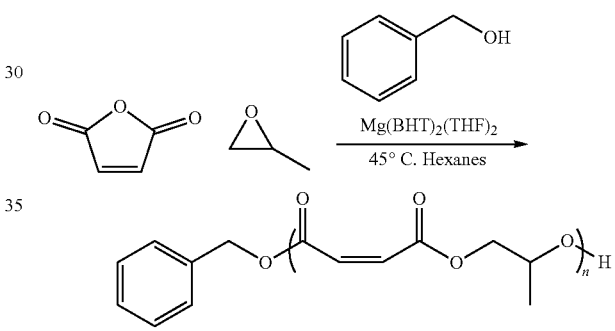

TABLE 8

| | | Benzyl alcohol initiated PPM (Hexane) | | | | | |
|---|---|---|---|---|---|---|---|
| [I]:[cat.] | [I]:[M] | T (° C.) | Time (days) | $M_{n, NMR}$ (kDa) | $M_{n, SEC}$ (kDa) | $M_{n, SEC}$ (kDa) | $Đ_M$ |
| 1:1 | 1:10 | 45 | 4 | 1.3 | 1.1 | 1.3 | 1.17 |
| 1:1 | 1:25 | 45 | 6 | 2.9 | 1.9 | 2.3 | 1.19 |
| 1:1 | 1:50 | 45 | 8 | 6.0 | 3.6 | 5.5 | 1.55 |
| 1:1 | 1:100 | 45 | 10 | 8.6 | 8.0 | 11.6 | 1.44 |

The presence of a benzyl terminated poly(propylene maleate) product was confirmed by $^1$H NMR (300 MHz, 303 K, CDCl$_3$): δ=7.35 (m, $C_6H_5$), 6.50-6.15 (m, OC(=O)H=CH(=O)O), 5.25-5.16 (m, $CH_2CH(CH_3)$O and ($C_6H_5$)$CH_2$O), 4.24-4.12 (m, $CH_2CH(CH_3)$O), and 1.39-1.11 (m, $CH_2CH(CH_3)$O) ppm. $^{13}$C NMR (125 MHz, 298 K, CDCl$_3$): δ=164.60 and 164.30 (MAn*-PO, OCOCH$_2$), 130.58 and 130.14 (MAn*-PO, O(O)C*CH=CH), 130.00 and 129.51 (MAn*-PO, O(O)C*CH=CH), 128.40 and 128.19 (aromatic Cs), 68.76 (MAn*-PO, OCH(CH$_3$)CH$_2$), 66.98 (MAn*-PO, OCH(CH$_3$)CH$_2$), 65.80 (($C_6H_5$)CH$_2$O) and 15.73 (PO, $CH_2$CH(CH$_3$)O) ppm. SEC (DMF): $M_n$=3.7 kDa, $M_w$=4.6 kDa, $Đ_M$=1.3. (See FIG. 27)

Example 5

Synthesis of Propargyl Alcohol Initiated End-Functionalized Poly Propylene Maleate End-functionalized poly(propylene maleate) was synthesized using the method set forth in Example 1 using propargyl alcohol as the initiating alcohol and a magnesium catalyst as shown in Scheme 9, below and using the reaction parameters shown in Table 9, below.

Scheme 9
Copolymerization of maleic anhydride and propylene oxide initiated by propargyl alcohol and catalyzed by $Mg(BHT)_2(THF)_2$.

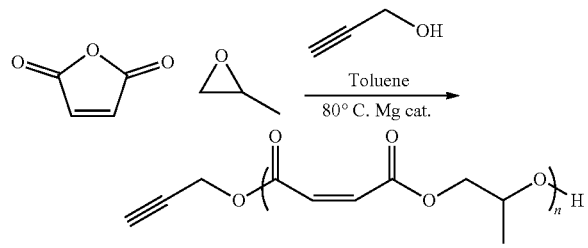

TABLE 9

Propargyl alcohol initiated PPM

| [I]:[cat.] | [I]:[M] | T (° C.) | Time (h) | $M_n$ (kDa) | $Đ_M$ |
|---|---|---|---|---|---|
| 1:1 | 1:10 | 80 | 18 | 2.4 | 1.14 |
| 1:1 | 1:25 | 80 | 18 | 3.0 | 1.11 |
| 1:1 | 1:50 | 80 | 48 | 4.0 | 1.49 |
| 1:1 | 1:100 | 80 | 48 | 7.2 | 1.35 |

The presence of a propargyl terminated poly(propylene maleate) product was confirmed by $^1H$ NMR (300 MHz, 303 K, DMSO-$d_6$): δ=6.54-6.27 (m, OC(=O)H=CH(=O)O), 5.39-5.21 (m, $CH_2CH(CH_3)O$), 4.88 (s, HC≡CCH$_2$O), 4.78 (s, HC≡CCH$_2$O), 4.38-4.21 (m, $CH_2CH(CH_3)O$), 2.27 (s, HC≡C) and 1.38-1.19 (m, $CH_2CH(CH_3)O$) ppm; $^{13}C$ NMR (125 MHz, 298 K, DMSO-$d_6$): δ=164.60 and 164.29 (MAn*-PO, OCOCH$_2$), 130.58 and 130.14 (MAn*-PO, O(O)C*CH=CH), 130.00 and 129.51 (MAn*-PO, O(O)C*CH=CH), 83.56 (HC≡CCH$_2$), 68.90 (HC≡CCH$_2$) 68.76 (MAn*-PO, OCH(CH$_3$)CH$_2$), 66.98 (MAn*-PO, OCH(CH$_3$)CH$_2$), 65.83 (HC≡CCH$_2$O) and 15.72 (CH$_2$CH(CH$_3$)O) ppm; and SEC (DMF): $M_n$=3.4 kDa, $M_w$=3.5 kDa, $Đ_M$=1.1. Yield=83%.

Example 6

Synthesis of Propargyl Alcohol Initiated End-Functionalized Poly(Propylene Maleate) Using Hexanes End-functionalized poly(propylene maleate) was synthesized using the method set forth in Example 2 above using propargyl alcohol as the initiating alcohol, hexane and a magnesium catalyst as shown in Scheme 10, below and using the reaction parameters shown in Table 10, below.

Scheme 10
Copolymerization of maleic anhydride and propylene oxide initiated by propargyl alcohol and catalyzed by $Mg(BHT)_2(THF)_2$.

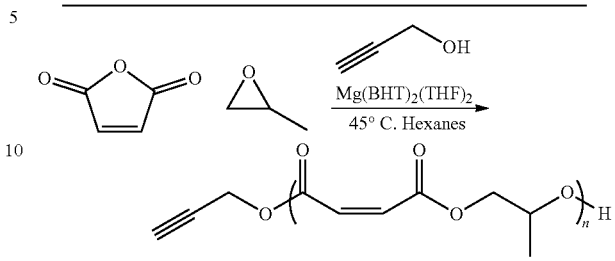

The presence of a propargyl terminated poly(propylene maleate) product was confirmed by $^1H$ NMR (300 MHz, 303 K, DMSO-$d_6$): δ=6.54-6.27 (m, OC(=O)H=CH(=O)O), 5.39-5.21 (m, $CH_2CH(CH_3)O$), 4.88 (s, HC≡CCH$_2$O), 4.78 (s, HC≡CCH$_2$O), 4.38-4.21 (m, $CH_2CH(CH_3)O$), 2.27 (s, HC≡C) and 1.38-1.19 (m, $CH_2CH(CH_3)O$) ppm. $^{13}C$ NMR (125 MHz, 298 K, DMSO-$d_6$): δ=164.60 and 164.29 (MAn*-PO, OCOCH$_2$), 130.58 and 130.14 (MAn*-PO, O(O)C*CH=CH), 130.00 and 129.51 (MAn*-PO, O(O)C*CH=CH), 83.56 (HC≡CCH$_2$), 68.90 (HC≡CCH$_2$) 68.76 (MAn*-PO, OCH(CH$_3$)CH$_2$), 66.98 (MAn*-PO, OCH(CH$_3$)CH$_2$), 65.83 (HC≡CCH$_2$O) and 15.72 (CH$_2$CH(CH$_3$)O) ppm. SEC (DMF): $M_n$=750 Da, $M_w$=1170 Da, $Đ_M$=1.55. (See FIG. 1)

Example 7

Synthesis of 4-Hydroxybutan-2-One Initiated End-Functionalized Poly Propylene Maleate End-functionalized poly(propylene maleate) was synthesized using the method set forth in Example 1 using 4-hydroxybutan-2-one as the initiating alcohol and a magnesium catalyst as shown in Scheme 11, below and using the reaction parameters shown in Table 10, below.

Scheme 11
Copolymerization of maleic anhydride and propylene oxide initiated by 4-hydroxybutan-2-one and catalyzed by $Mg(BHT)_2(THF)_2$

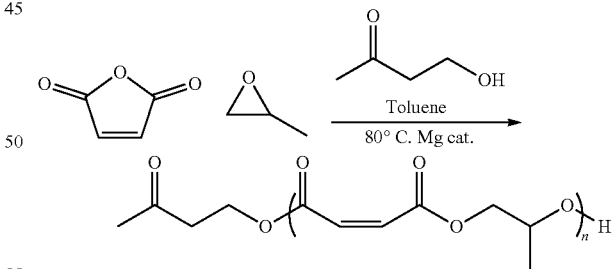

TABLE 10

4-hydroxybutan-2-one initiated PPM

| [I]:[cat.] | [I]:[M] | T (° C.) | Time (h) | $M_n$ (kDa) | $Đ_M$ |
|---|---|---|---|---|---|
| 1:1 | 1:10 | 80 | 18 | 1.9 | 1.19 |
| 1:1 | 1:25 | 80 | 18 | 2.3 | 1.05 |
| 1:1 | 1:50 | 80 | 48 | 6.9 | 1.67 |
| 1:1 | 1:100 | 80 | 48 | 11.2 | 1.46 |

Figure 3:
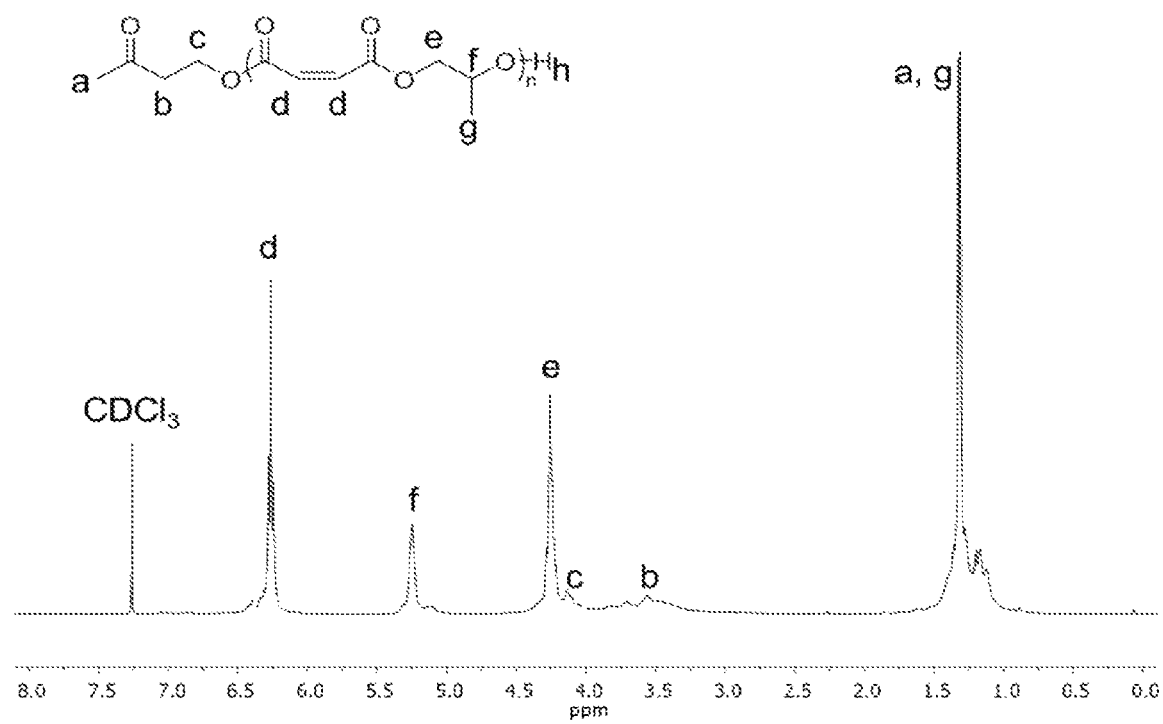
FIG. 3 is a $^1H$ NMR spectrum of DP 25 4-hydroxybutan-2-one initiated poly(propylene maleate) (Table 2, Entry 10) using $Mg(BHT)_2(THF)_2$ as a catalyst (300 MHz, 303 K, DMSO-$d_6$).

The presence of a 4-hydroxybutan-2-one terminated poly(propylene maleate) product was confirmed by $^1$H NMR (300 MHz, 303 K, CDCl$_3$): δ=6.42-6.28 (m, OC(═O)H═CH(═O)O), 5.33-5.25 (m, CH$_2$CH(CH$_3$)O), 4.32-4.18 (m, CH$_2$CH(CH$_3$)O), 4.08 (m, CH$_2$CH$_2$O), 3.64 and 3.53 (m, CH$_3$C(═O)CH$_2$CH$_2$), and 1.38-1.13 (m, CH$_2$CH(CH$_3$)O and CH$_3$C(═O)CH$_2$) ppm (See FIG. 3); $^{13}$C NMR (125 MHz, 303 K, DMSO-d$_6$): δ=165.42 (CH$_3$C(═O)CH$_2$), 164.60 and 164.30 (MAn*-PO, OCOCH$_2$), 130.55 and 130.16 (MAn*-PO, O(O)C*CH═CH), 129.81 and 129.84 (MAn*-PO, O(O)C*CH═CH), 128.15, 68.77 (MAn*-PO, OCH(CH$_3$)CH$_2$), 66.97 (MAn*-PO, OCH(CH$_3$)CH$_2$), 65.81 (CH$_2$CH$_2$O), 30.63 (C(═O)CH$_2$CH$_2$), 25.08 (CH$_3$C(═O)CH$_2$) and 15.74 (CH$_2$CH(CH$_3$)O) ppm; and SEC (THF): $M_n$=1.5 kDa, $M_w$=2.0 kDa, Đ$_M$=1.3. Yield=88%.

Example 8

General Procedure for the Isomerization of PPM

End-functionalized poly(propylene fumarate) was dissolved into chloroform. Diethylamine was added to the solution and refluxed for 24 h under a nitrogen atmosphere. After cooling to room temperature, the organic solution was washed with phosphate buffer solution (pH=6) and the polymer was recovered through precipitation from hexanes.

Example 9

Isomerization of PPM

End-functionalized poly(propylene maleate) (11 g, 8 mol. eq. olefin) was dissolved into chloroform 1125 ml). Diethylamine 10.01 ml, 0.15 mol. eq. olefin) was added to the solution and refluxed for 24 h under a nitrogen atmosphere. After cooling to room temperature, the organic solution was washed with phosphate buffer solution 1350 ml, pH; 6) and the PPF polymer was recovered through precipitation from hexanes. (See, FIG. 2)

Example 10

Isomerization of Benzyl Functionalized PPM

Benzyl functionalized poly(propylene maleate) was isomerized to form benzyl terminated poly(propylene fumarate) using the method shown in Examples 8 and 9, above and as shown in Scheme 12, below.

Scheme 12
Isomerization of poly(propylene maleate) to form poly(propylene fumarate).

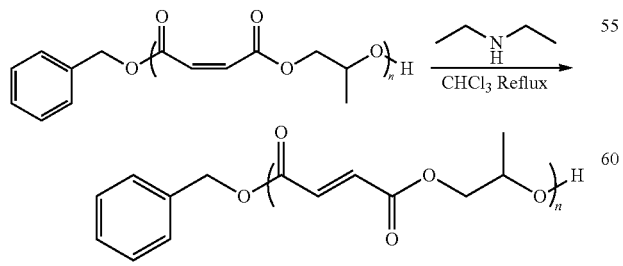

The isomerization of the benzyl functionalized poly(propylene maleate) into the corresponding benzyl functionalized poly(propylene fumarate) was confirmed by $^1$H NMR (300 MHz, 303 K, CDCl$_3$): δ=7.32 (m, Ar), 6.87 (m, OC(═O)H═CH(═O)O), 5.36 (m, CH$_2$CH(CH$_3$)O), 5.09 (s, C═OOCH$_2$Ar), 4.04 (m, CH$_2$OC═O), 2.28 (s, εCL CH$_2$C═OO), 1.26 (m, CH$_2$CH(CH$_3$)O), 1.60 and 1.33 (all remaining hydrogens) ppm.

Example 11

Isomerization of Propargyl-Functionalized Poly Propylene Fumarate

Propargyl poly(propylene maleate) was isomerized to form propargyl terminated poly(propylene fumarate) using the general method set forth above and as shown in Scheme 13, below.

Scheme 13

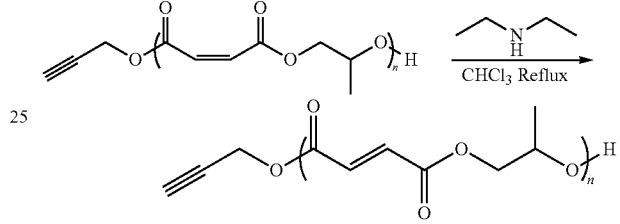

Isomerization of propargyl poly(propylene maleate) to form propargyl terminated poly(propylene fumarate) was confirmed by $^1$H NMR (300 MHz, 303 K, DMSO-d$_6$): δ=6.84-6.64 (m, OC(═O)H═CH(═O)O), 5.27-5.07 (m, CH$_2$CH(CH$_3$)O), 4.85 (s, HC≡CCH$_2$O), 4.78 (s, HC≡CCH$_2$O), 4.44-4.14 (m, CH$_2$CH(CH$_3$)O), 2.32 (s, HC≡C) and 1.38-1.10 (m, CH$_2$CH(CH$_3$)O) ppm. Yield=98%. A $^1$H NMR spectra comparison of propargyl poly(propylene fumarate) (top) against the precursor propargyl poly(propylene maleate) (bottom) (300 MHz, 303 K, DMSO-d$_6$) is shown in FIG. 4.

Example 12

Subtractive Method of Surface Concentration Determination

PPF thin films (1 cm×1 cm) were immersed in a dye solution (0.5 μM Chromeo® 546-azide dye, 2.5 mg CuSO$_4$, 3.2 mg sodium ascorbate in a 50% v/v solution of EtOH/H$_2$O) for 1 h, and the concentration of the solution was determined using fluorescence spectroscopy. The unused solution was used as a standard to measure dye attachment to films.

Example 13

Copper-Mediated Azide-Alkyne Cycloaddition of Megastokes® 673-Azide Dye to Propargyl Functionalized PPF A Megastokes® 673-azide solution (1 mM dye in a 50% v/v solution of 50:50 isopropyl alcohol:H$_2$O, 0.5 mg CuSO$_4$, 1.5 mg sodium ascorbate) was pipetted onto a PPF film and allowed to remain for 1 h, before being washed with isopropyl alcohol and H$_2$O to remove any non-tethered dye and catalyst.

Example 14

Synthesis of N3-GRGDS [Seq. ID No. 1] peptide

GRGDS [Seq. ID No. 1] was synthesized by microwave-assisted solid phase peptide synthesis (SPSS) on a CEM Liberty 1 peptide synthesizer using standard Fmoc chemistry conditions (0.25 mmol scale). 6-Bromohexanoic acid (1 mmol) was added along with the GRGDS [Seq. ID No. 1] Wang resin (0.25 mmol), diisopropylcarbodiimide (DIC, 1.1 mmol) and hydroxybenzotriazole (HOBt, 1.1 mmol) and allowed to react for 2 hours. The Br-functionalized peptide was then cleaved from the resin using 15 mL of a solution of trifluoroacetic acid, triisopropylsilane, and water (95:2.5:2.5 vol. %). Following three trituration cycles in diethyl ether, the resulting white solid was dried overnight under vacuum. The solid was then redissolved in a 10% ethanol solution in water. Coupling of the azide group was performed after the microwave synthesis. $NaN_3$ (1.25 mmol) and 18-Crown-6 (0.0625 mmol) was added to the Wang resin and allowed to react for 12 h to yield $N_3$-GRGDS [Seq. ID No. 1] (ESI m/z: $[M+H]^+$ Calculated for $C_{23}H_{40}N_{11}O_{10}$ 630.29; Found 630.157).

Example 15

Seeding of MC3T3-E1 onto Poly(Propylene Fumarate) Discs

Propargyl alcohol-initiated poly(propylene fumarate) disks (ø=6 mm) were washed with chloroform, acetone, and ethanol for 1 h each, followed by soaking in 1×PBS for 12 hours. Afterwards, films were sterilized by soaking in 70% EtOH for 1 h, followed by 15 min exposure to UV light. Prior to cell seeding, the films were submerged in Alpha-MEM for 2 h prior to cell seeding. Mouse calvarial stem cells (MC3T3-E1) were cultured in Alpha-MEM media supplemented with 10% fetal bovine serum (FBS), 100 units/mL penicillin, and 100 $\mu g \cdot mL^{-1}$ streptomycin and passaged every 3 days. MC3T3s at passage 8 were seeded at 250 cells·$mm^{-2}$ and all subsequent experiments were performed 48 h after cell seeding.

Example 16

MC3T3 Cell Viability on Poly(Propylene Fumarate) Discs

Cell viability was evaluated using a LIVE/DEAD viability cytotoxicity kit at 48 h. Briefly, 5 µL of the 4 mM Calcein-AM stock solution and 10 µL of the 2 mM ethidium homodimer-1 (EthD-1) stock solution were added to 10 mL of PBS to prepare the Live/Dead staining solution. Samples were washed thrice with 1×PBS (1 mL). The stock solution (200 µL) was added to each sample and incubated for 15 minutes. The staining solution was then removed, and samples were viewed under a IX81 fluorescence microscope using FITC and TRITC emission filters. For analysis, 10 random areas were chosen per film and each film was performed in triplicate. The values were normalized to cell viability calculated on a glass slide.

Example 17

MC3T3 Cell Spreading on Poly(Propylene Fumarate) Discs

Cell spreading was evaluated by staining of cytoskeletal actin 48 h after cell seeding. Samples were prefixed in a 3.7% paraformaldehyde in CS buffer solution for 1 hour, washed thrice with 1×PBS and stored at −80° C. until staining. To stain, samples were incubated in a 0.5% v/v Triton X-100 in CS buffer solution for 10 minutes and washed thrice with 1×PBS. Next, samples were incubated in a 0.1 wt. % $NaBH_4$ solution in 1×PBS solution for 10 minutes and washed thrice with 1×PBS. Rhodamine phalloidin (1:40 v/v in 1×PBS) was then added to the samples and incubated for 1 hour. After washing thrice with 1×PBS, DAPI solution (6 µL of a 5 $\mu g \cdot mL^{-1}$ DAPI in 10 mL PBS) was added to the samples and incubated for 20 minutes. After washing 3× with 1×PBS, samples were mounted using fluorescence mounting media and imaged using a fluorescence microscope.

Materials and Apparatus for Examples 18 Through 26

The materials and apparatuses used herein are set forth in Table 11 and Table 12 below.

TABLE 11

Materials Used

| Name | Formula | Purity | Source |
|---|---|---|---|
| benzyl alcohol | $C_7H_8O$ | ≥99.0% | Sigma-Aldrich |
| 2,4-di-tert-butylphenol | $C_{15}H_{24}O$ | 99% | Sigma-Aldrich |
| di-n-butylmagnesium | $C_8H_{18}Mg$ | 99% | Sigma-Aldrich |
| chloroform | $CHCl_3$ | GR ACS | Sigma-Aldrich |
| dichloromethane | $CH_2Cl_2$ | 99.9% | Fisher Chemical |
| 1,4-dixoane | $C_4H_8O_2$ | ≥99.0% | Sigma-Aldrich |
| diethyl ether | $C_4H_{10}O$ | GR ACS | VWR |
| diethylamine | $C_4H_{11}N$ | 99%, extra pure | Sigma-Aldrich |
| (±)-epichlorohydrin | $C_3H_5ClO$ | ≥99.0% | Fluka |
| hexane | $C_6H_{14}$ | 98.5% | Sigma-Aldrich |
| maleic anhydride | $C_4H_2O_3$ | 99% | Fluka |
| magnesium sulfate | $MgSO_4$ | ≥99.5% | Sigma-Aldrich |
| o-nitrobenzyl alcohol | $C_7H_7NO_3$ | 97% | Sigma-Aldrich |
| propargyl alcohol | $C_3H_4O$ | 99% | Sigma-Aldrich |
| petroleum ether | — | GR ACS | Sigma-Aldrich |
| sodium hydroxide | NaOH | GR ACS | VWR |
| sodium phosphate dibasic | $Na_2HPO_4$ | BioXtra, ≥99.0% | Sigma-Aldrich |
| sodium phosphate monobasic | $NaH_2PO_4$ | BioXtra, ≥99.0% | Sigma-Aldrich |
| sodium chloride | NaCl | GR ACS | VWR |
| sodium sulfate | $NaSO_4$ | ≥99.0% | VWR |
| sodium bicarbonate | $NaHCO_3$ | ≥99.7% | Sigma-Aldrich |
| tetrabutylammonium hydrogensulfate | $C_{16}H_{37}NO_4S$ | 98% | ACROS |
| toluene | $C_7H_8$ | anhydrous, 99.8% | Sigma-Aldrich |
| tetrahydrofuran | $C_4H_8O$ | GR ACS | Sigma-Aldrich |

TABLE 12

Apparatus used in for Examples 18 through 26

| Apparatus | Type |
|---|---|
| $^1$H NMR | Varian Mercury 300 Spectra |
| $^{13}$C NMR | Varian Mercury 500 Spectra |
| SEC (size exclusion chromatography) | Tosoh EcoSEC HLC-8320 |
| MALDI-ToF MS (matrix-assisted laser desorption/ionization time-of-flight mass spectroscopy) | Bruker UltraFlex III MALDI tandem Time-of-Flight (TOF/TOF) mass spectrometer |
| Oven | Precision Scientific Co. |

Characterization for Examples 18 Through 26

Proton (H) NMR spectra were recorded using a Varian Mercury-300 NMR spectrometer. Carbon ($^{13}$C) NMR spectra were recorded using a Varian Mercury-500 NMR spectrometer. All chemical shifts were recorded in parts per million (ppm) relative to a reference peak of chloroform solvent at δ=7.26 ppm and 77.16 ppm for $^1$H and $^{13}$C NMR spectra respectively. Molecular weights were determined through size exclusion chromatography (SEC) using a Tosoh EcoSEC HLC-8320 on PLgel Mixed-C type columns in series with refractive index (RI) detection. Weights were calculated using a calibration curve determined from poly (styrene) standards with DMF (0.1% LiBr) as eluent flowing at 0.5 mL·min$^{-1}$ and sample concentration 20 mg·mL$^{-1}$. MALDI-ToF (matrix assisted laser desorption ionisation—time of flight) mass spectra were recorded using a Bruker UltraFlex III MALDI tandem Time-of-Flight (TOF/TOF) mass spectrometer.

Example 18

Synthesis of Glycidyl Propargyl Ether GPE

Glycidyl propargyl ether (GPE) was synthesized as shown in Scheme 14, below.

Scheme 14
Synthesis of glycidyl propargyl ether (GPE)

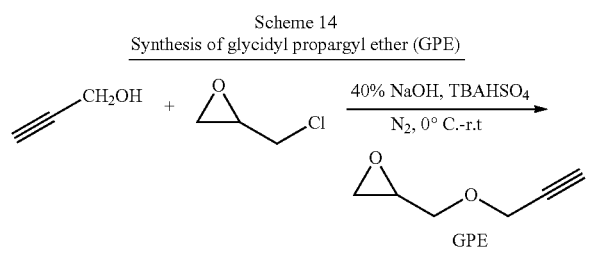

GPE

Propargyl alcohol (7.6 ml, 0.135 mol) was added dropwise to stirring 40% aqueous sodium hydroxide solution (56.5 g NaOH in 85 g of H$_2$O) at 0° C. The mixture was stirred for 30 minutes. A solution of (±)-epichlorohydrin (25 g, 0.27 mol), hexanes (90 ml), tetrabutylammonium hydrogensulfate (2.29 g, 6.75 mmol) and H$_2$O (12.5 ml) was added into the reaction system. The reaction was allowed to warm to room temperature, and the reaction continued for 8 h under a N$_2$ blanket. The reaction was quenched with brine (125 ml), and crude product was extracted with three portions of 125 mL of dichloromethane (DCM). The combined organic layers were dried over Na$_2$SO$_4$, filtered, and concentrated by rotary evaporation. The final product was obtained by column chromatography (1:3 hexanes/DCM to DCM), resulting in GPE in a yield of 7.3 g (48.1%) (Scheme 3.1). $^1$H NMR (300 MHz, 303 K, CDCl$_3$): δ=3.98 (t, OCH$_2$≡CCH), 3.61-3.56 (q, CHCH$_2$OCH$_2$), 3.26-3.20 (q, CHCH$_2$OCH$_2$), 2.95-2.89 (m, CHCH$_2$OCH$_2$), 2.57-2.54 (t, CH$_2$(O)CHCH$_2$O), 2.39-2.35 (m, CH$_2$(O)CHCH$_2$O, C≡CH) ppm.

Example 19

Synthesis of 2-[[(2-Nitrophenyl)Methoxy]Methyl] Oxirane (NMMO

2-[[(2-nitrophenyl)methoxy]methyl]oxirane (NMMO) was synthesized as shown in Scheme 15, below.

Scheme 15
Synthesis of 2-[[(2-nitrophenyl)methoxy]methyl]oxirane (NMMO)

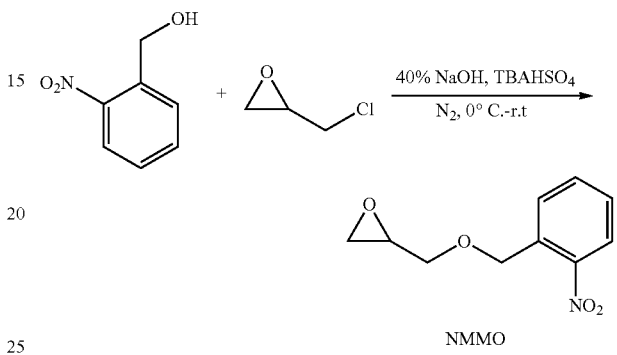

NMMO o-Nitrobenzyl alcohol (10 g, 0.065 mol) was dissolved in 30 mL of 1,4-dixoane followed by addition of tetrabutylammonium hydrogensulfate (1.11 g, 3.27 mmol) and a 40% aqueous sodium hydroxide solution (8 g NaOH in 12 g H$_2$O). (±)-Epichlorohydrin (20 mL, 0.26 mol) was subsequently added dropwise to the mixture at 0° C., the reaction was then allowed to warm to room temperature. After stirring for 48 h under N$_2$, the reaction mixture was extracted with two portions of 50 mL of diethyl ether. The combined ether fractions were washed with excess of water, saturated sodium bicarbonate, and saturated sodium chloride. The combined organic layers were dried over MgSO$_4$, filtered, and concentrated by rotary evaporation. Final product was obtained by column chromatography (5:3 petroleum ether/diethyl ether), resulting in NMMO in a yield of 3.7 g (27.2%) (Scheme 3.2). $^1$H NMR (300 MHz, 303 K, CDCl$_3$): δ=7.95-7.32 (m, Ar), 4.85 (s, ArCH$_2$OCH$_2$), 3.84-3.79 (q, CHCH$_2$OCH$_2$), 3.45-3.39 (q, CHCH$_2$OCH$_2$), 3.16-3.11 (m, CHCH$_2$OCH$_2$), 2.74-2.71(t, CH$_2$(O)CHCH$_2$O), 2.58-2.55 (q, CH$_2$(O)CHCH$_2$O) ppm.

Example 20

Synthesis of Magnesium 2,6-Di-Tert-Butyl-4-Methylphenoxide (Mg(BHT)$_2$(THF)$_2$ Using standard Schlenk line techniques, a schlenk was filled with 2,6-di-tert-butyl-4-methylphenol (BHT) (6.66 g, 30 mmol) and dissolved into dry toluene (30 ml) added by cannula transfer. Di-n-butylmagnesium (1M in hexane, 15 ml, 15 mmol) was added dropwise to the reaction with stirring. The reaction was stirred for a further 2 hours followed by removing solvent. Hexanes (12.5 ml) were added to the reaction vessel followed by addition of tetrahydrofuran (THF) (2.5 ml). After stirring for 2 hours under N$_2$, solvent can be removed, and final product was obtained as a solid (Scheme 16).

Scheme 16
Synthesis of magnesium 2,6-di-tert-butyl-4-methylphenoxide (Mg(BHT)₂(THF)₂)

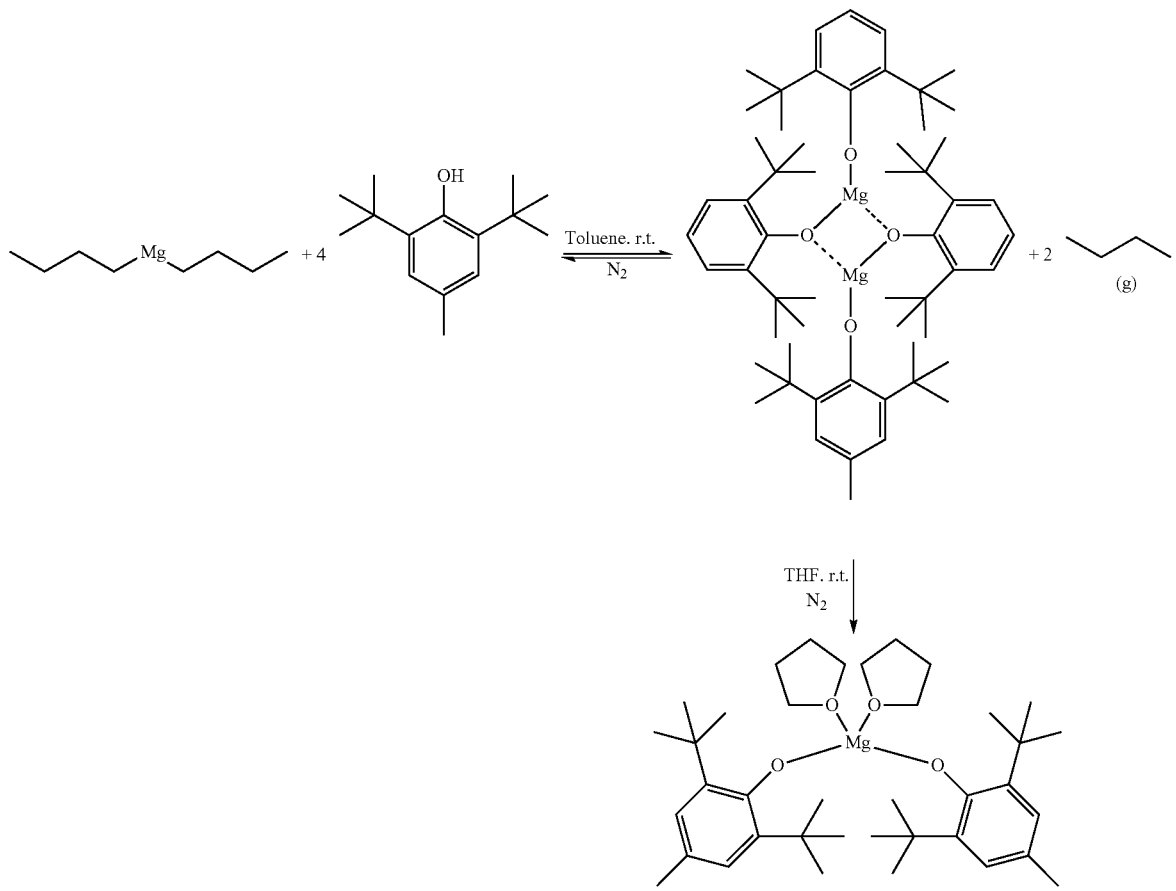

Example 21

General Procedure for Polymerization of Functionalized PPF

Using standard Schlenk line techniques, an ampoule was filled with Mg(BHT)₂(THF)₂ (121.4 mg, 0.2 mmol), benzyl alcohol (0.02 mL, 0.2 mmol), epoxide (0.5 mmol) and maleic anhydride (490.3 mg, 0.5 mmol). The reagents were dissolved into toluene to a total monomer concentration of 2 M. The ampoule was sealed and heated at 80° C. for 24 h. The resultant polymer was recovered by precipitation in excess diethyl ether. After centrifugation, the crude product was dissolved into chloroform, then diethylamine was added into the mixture followed by reflux under N₂ for 24 hours. Finally, the mixture was washed with excess phosphate buffer saline solution (0.5 M). Organic layers were combined and dried to recover the polymer.

Example 22

Synthesis of Poly(epichlorohydrin-Co-Maleic Anhydride)

Poly(epichlorohydrin-co-maleic anhydride) was synthesized from (±)-epichlorohydrin and maleic anhydride as shown in Scheme 17, below.

Scheme 17
Copolymerization of epichlorohydrin and maleic anhydride and isomerization of poly (ECH-co-MA)

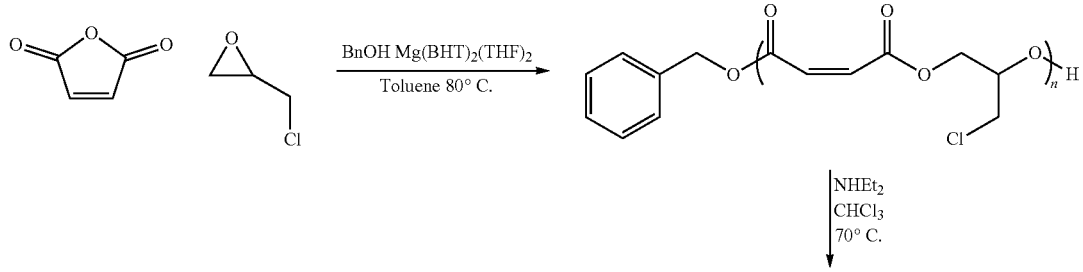

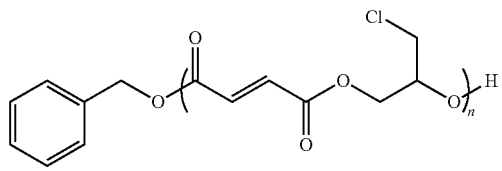

Using standard Schlenk line techniques, an ampoule was filled with Mg(BHT)$_2$(THF)$_2$ (121.4 mg, 0.2 mmol), benzyl alcohol (0.02 mL, 0.2 mmol), (±)-epichlorohydrin (0.5 mmol) and maleic anhydride (490.3 mg, 0.5 mmol). The reagents were dissolved into toluene to a total monomer concentration of 2 M. The ampoule was sealed and heated at 80° C. for 24 h. The resultant polymer was recovered by precipitation in excess diethyl ether. After centrifugation, the crude product was dissolved into chloroform, then diethylamine was added into the mixture followed by reflux under N$_2$ for 24 hours. Finally, the mixture was washed with excess phosphate buffer saline solution (0.5 M). Organic layers were combined and dried to recover the polymer.

Figure 28:
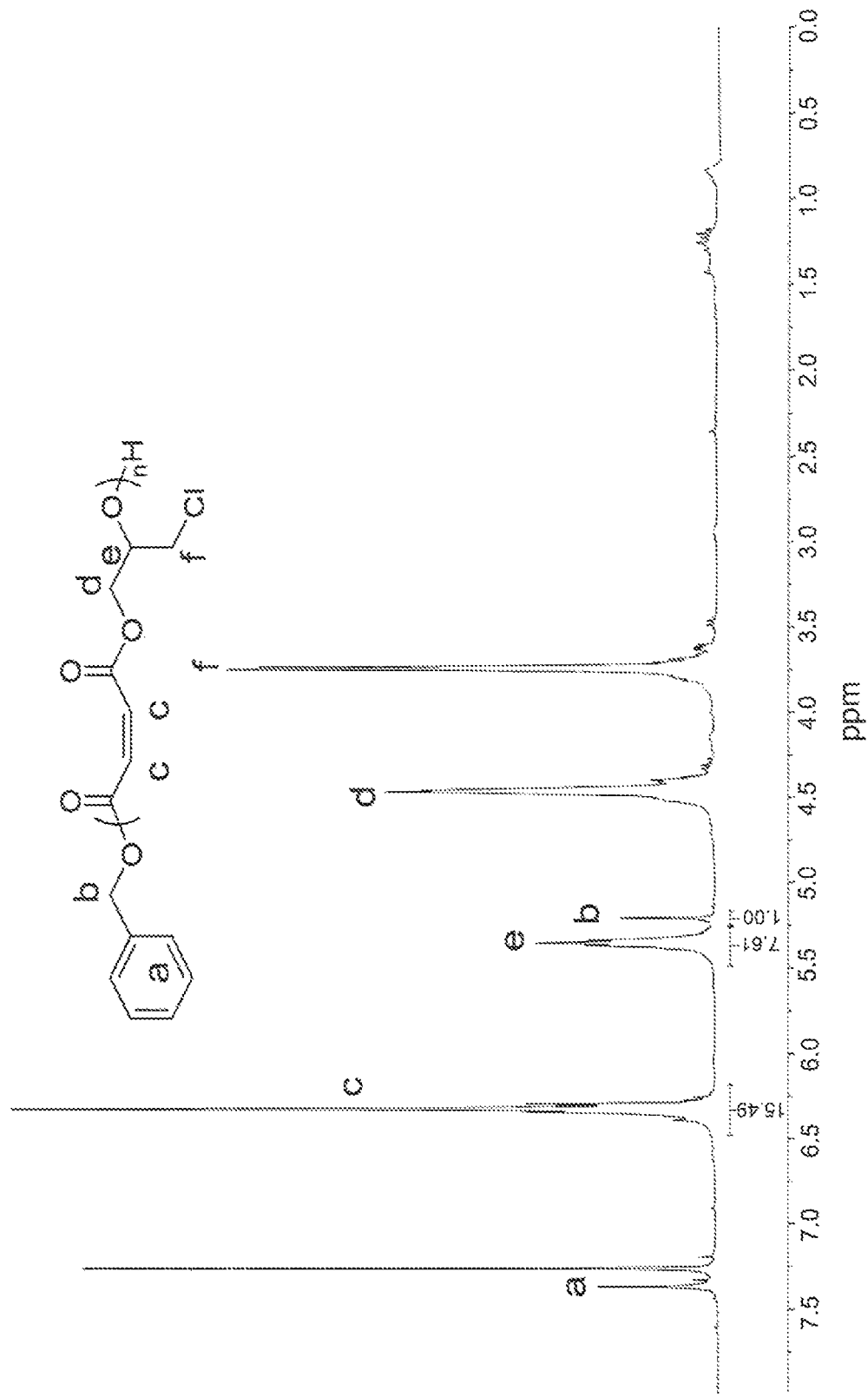
FIG. 28 is a $^1$H NMR spectrum of poly(ECH-co-MA) (300 MHz, 303 K, CDCl$_3$).
Figure 29:
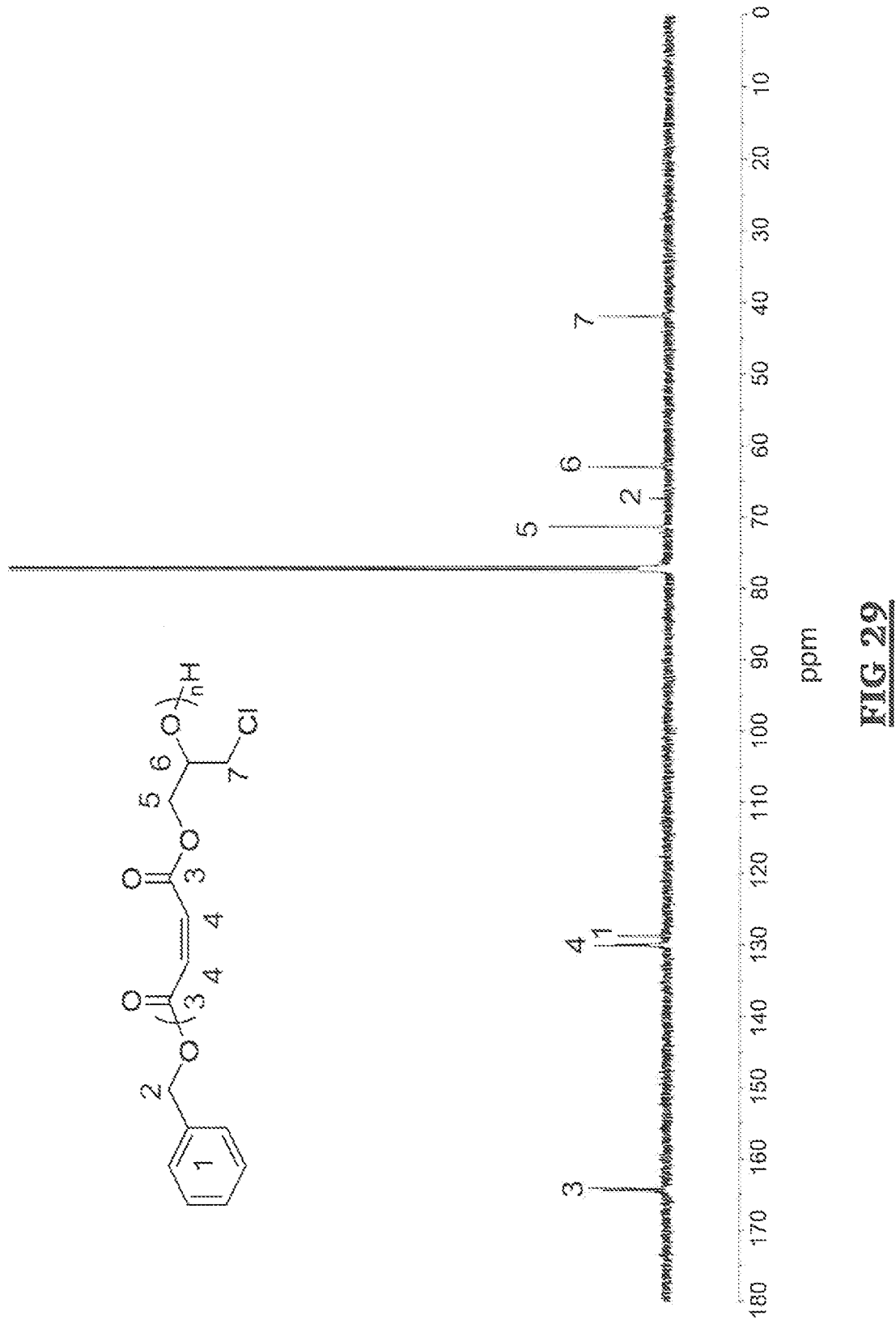
FIG. 29 is a quantitative $^{13}$C NMR spectrum of poly(ECH-co-MA)(125 MHz, 303 K, CDCl$_3$).
Figure 30:
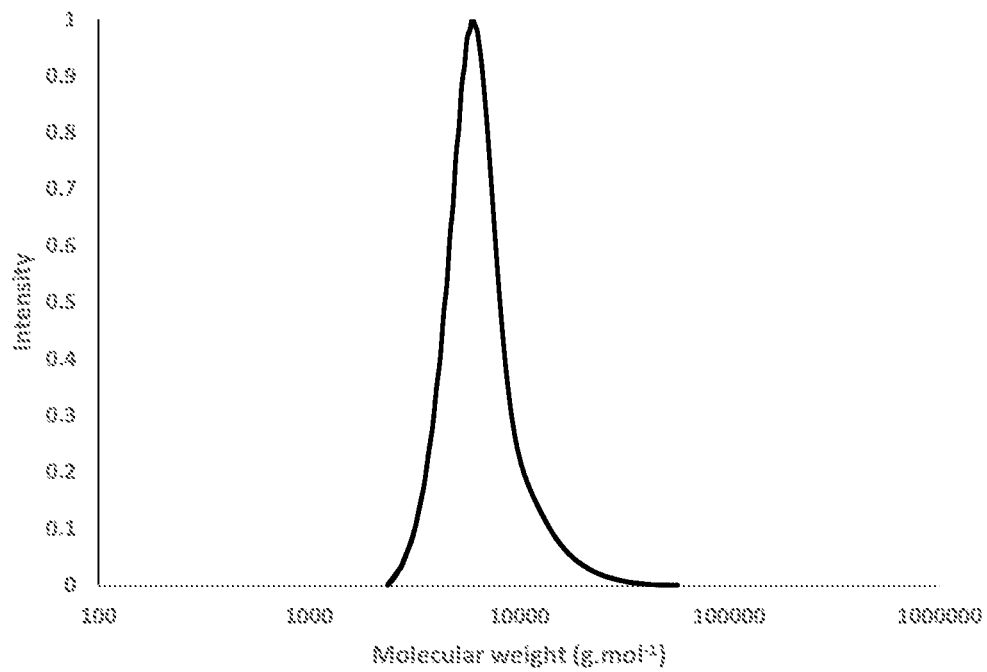
FIG. 30 is a SEC chromatogram of the molecular weight distribution of P(ECH-co-MA).

The resulting polymer was characterized by $^1$H NMR and the results reported here, in Table 5 and in FIG. 28. $^1$H NMR (300 MHz, 303 K, CDCl$_3$): δ=7.36 (m, Ar), 6.86 (m, COHC=CHCO), 5.35 (m, OCH$_2$CH(CH$_2$OCH$_2$C≡CH)O), 5.22 (s, ArCH$_2$O), 4.80-4.40 (m, OCH$_2$CH(CH$_2$OCH$_2$C≡CH)O), 4.18 (m, OCH$_2$CH(CH$_2$OCH$_2$C≡CH)O), 3.74 (d, CH(CH$_2$OCH$_2$C≡CH)O), 2.49 (s, CH(CH$_2$OCH$_2$C≡CH)O) ppm. The resulting polymer was also characterized by $^{13}$C NMR and the results reported here and in FIG. 29. $^{13}$C NMR (125 MHz, 303 K, CDCl$_3$): δ=164.30 (O—C=O), 130.03 (HC=CH), 128.74 (Ar C), 71.28 (OCH$_2$CH), 67.36 ((C$_6$H$_5$)CH$_2$O), 63.01 (CH$_2$CH(CH$_2$Cl)O), 41.89 (CHCH$_2$Cl) ppm. SEC (DMF): M$_n$=6.0 kDa, M$_w$=7.0 kDa, Đ$_M$=1.16. The resulting polymer was also characterized by Size Exclusion Chromatography (SEC) and the results reported here and in FIG. 30. SEC (DMF): M$_n$=6.0 kDa, M$_w$=7.0 kDa, Đ$_M$=1.16.

The results of Example 22 are summarized in Table 13, below.

TABLE 13

| | P(ECH-co-MA) | | | | | | | |
|---|---|---|---|---|---|---|---|---|
| Initiator | mol. eq. cat | mol. eq. GPE | mol. eq. MA | T (° C.) | Time (h) | M$_{n,\,NMR}$ (kDa) | M$_{n,\,GPC}$ (kDa) | Đ$_M$ |
| BnOH | 1 | 25 | 25 | 80 | 24 | 6.0 | 7.0 | 1.16 |

Example 23

Synthesis of Poly Glycidyl Propargyl Ether-Co-Maleic Anhydride

Poly(glycidyl propargyl ether-co-maleic anhydride) was synthesized from glycidyl propargyl ether (prepared as shown above in Example 18, above) and maleic anhydride as shown in Scheme 18, below.

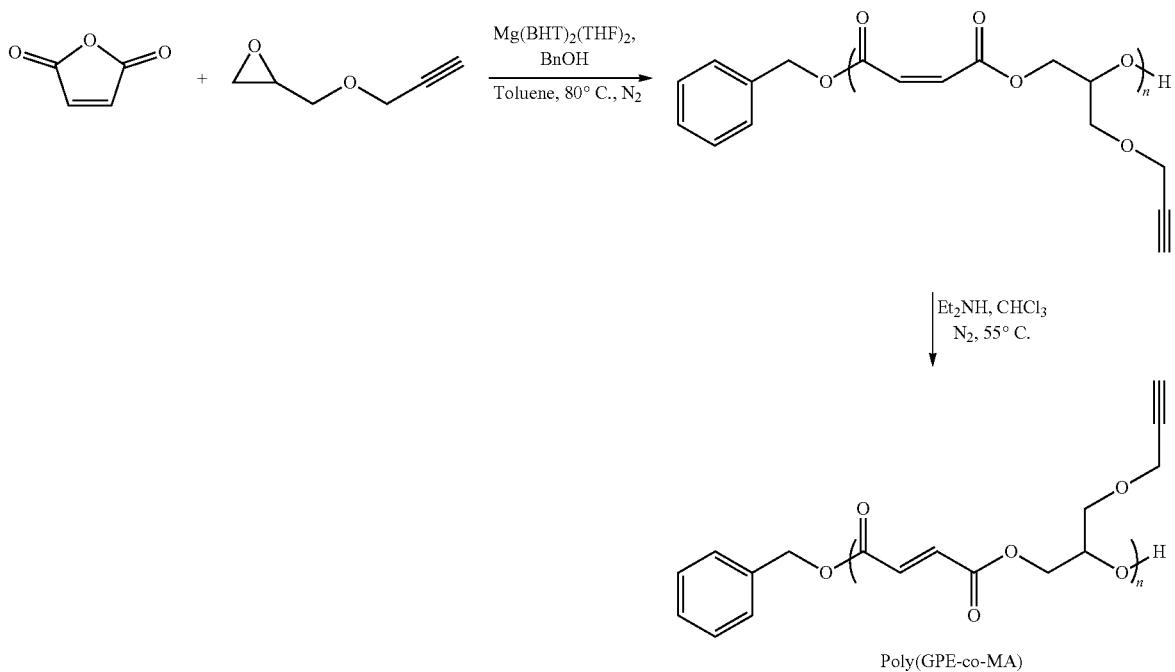

Scheme 18
Copolymerization of glycidyl propargyl ether and maleic anhydride and isomerization of poly(GPE-co-MA)

Poly(GPE-co-MA)

Using standard Schlenk line techniques, an ampoule was filled with $Mg(BHT)_2(THF)_2$ (121.4 mg, 0.2 mmol), benzyl alcohol (0.02 mL, 0.2 mmol), glycidyl propargyl ether (0.5 mmol) and maleic anhydride (490.3 mg, 0.5 mmol). The reagents were dissolved into toluene to a total monomer concentration of 2 M. The ampoule was sealed and heated at 80° C. for 24 h. The resultant polymer was recovered by precipitation in excess diethyl ether. After centrifugation, the crude product was dissolved into chloroform, then diethylamine was added into the mixture followed by reflux under $N_2$ for 24 hours. Finally, the mixture was washed with excess phosphate buffer saline solution (0.5 M). Organic layers were combined and dried to recover the polymer.

Figure 31:
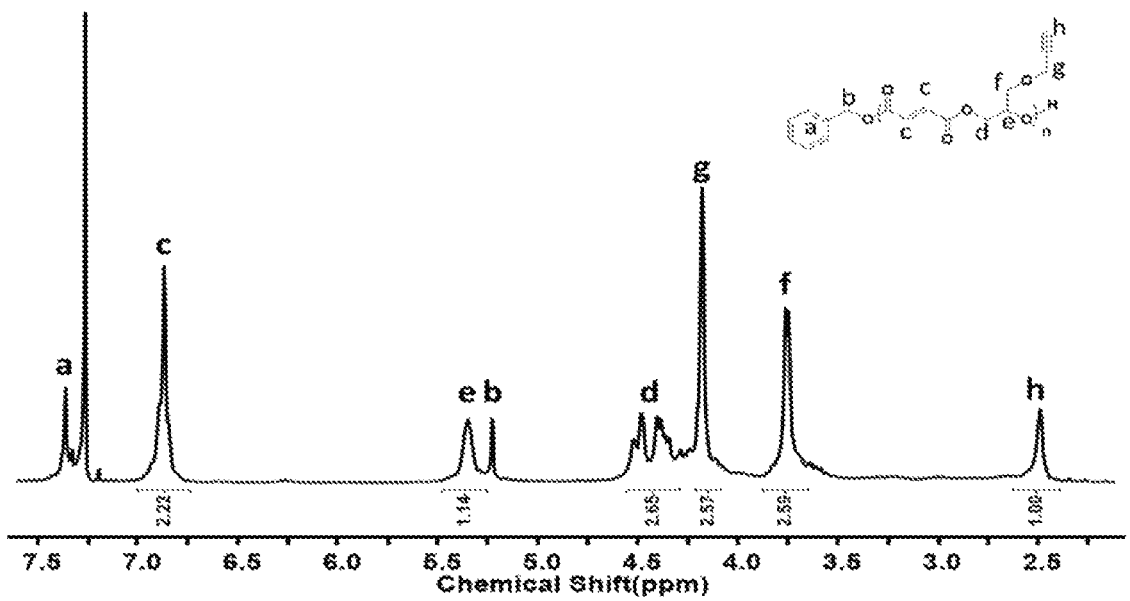
FIG. 31 is a $^1$H NMR spectrum of poly(GPE-co-MA) (300 MHz, 303 K, CDCl$_3$).
Figure 32:
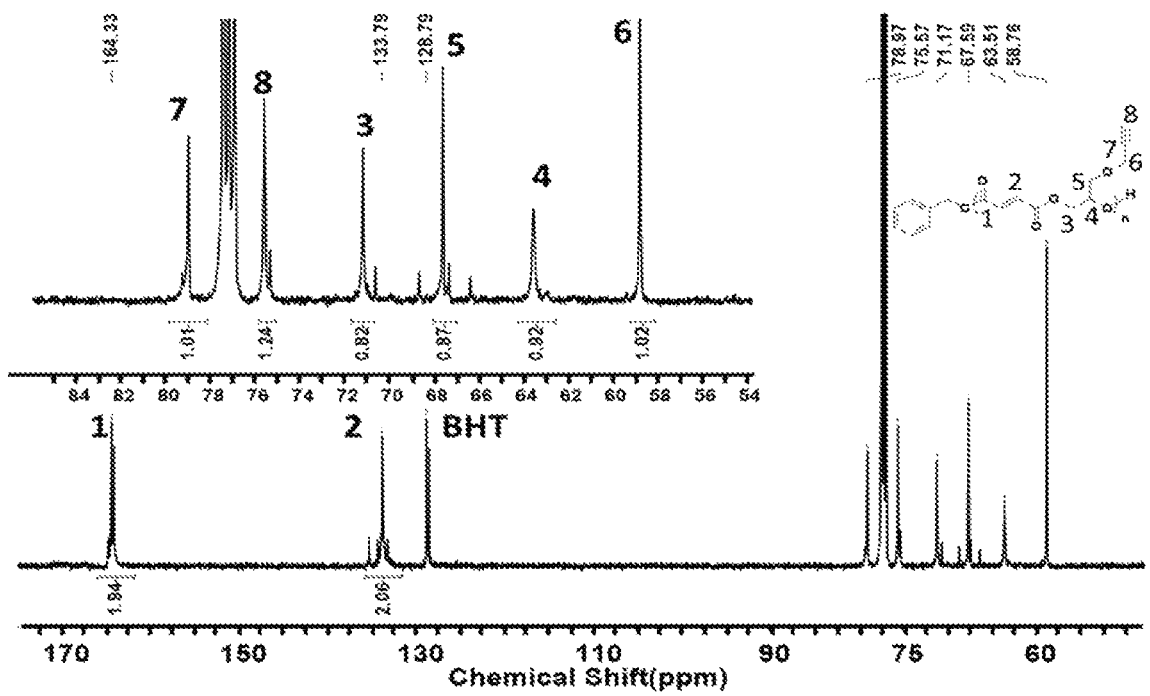
FIG. 32 is a quantitative $^{13}$C NMR spectrum of poly (GPE-co-MA)(125 MHz, 303 K, CDCl$_3$).

The resulting polymer was characterized by $^1H$ NMR and the results reported here, in Table 14 and in FIG. 31. $^1H$ NMR (300 MHz, 303 K, $CDCl_3$): δ=7.36 (m, Ar), 6.86 (m, COHC=CHCO), 5.35 (m, $OCH_2CH(CH_2OCH_2C\equiv CH)O$), 5.22 (s, $ArCH_2O$), 4.80-4.40 (m, $OCH_2CH(CH_2OCH_2C\equiv CH)O$), 4.18 (m, $OCH_2CH(CH_2OCH_2C\equiv CH)O$), 3.74 (d, $CH(CH_2OCH_2C\equiv CH)O$), 2.49 (s, $CH(CH_2OCH_2C\equiv CH)O$) ppm. The resulting polymer was characterized by $^{13}C$ NMR and the results reported here and in FIG. 32. $^{13}C$ NMR (125 MHz, 303 K, $CDCl_3$): δ=164.20 O—C=O), 133.79 (HC=CH), 79.12 ($H_2C\equiv CH$), 75.57 ($H_2C\equiv CH$), 71.17 ($OCH_2CH$), 67.59 ($CH_2OCH_2C\equiv CH$), 63.51 ($CH_2CH(CH_2OCH_2C\equiv CH)O$), 58.76 ($CH_2OCH_2C\equiv CH$) ppm. The polymer was also characterized by Size Exclusion Chromatography (SEC). SEC (DMF): $M_n$=7.6 kDa, $M_w$=10.6 kDa, $Đ_M$=1.40. The results of Example 23 are summarized in Table 14, below.

TABLE 14

| | P(GPE-co-MA) | | | | | | | |
|---|---|---|---|---|---|---|---|---|
| Initiator | mol. eq. catalyst | mol. eq. GPE | mol. eq. MA | T (° C.) | Time (h) | $M_{n, NMR}$ (kDa) | $M_{n, GPC}$ (kDa) | $Đ_M$ |
| BnOH | 1 | 25 | 25 | 80 | 24 | 4.5 | 7.6 | 1.40 |

Example 24

Synthesis of Poly(Glycidyl Propargyl Ether-Co-Maleic Anhydride) (Poly(GPE-Co-MA))[7]

Using standard Schlenk line techniques, an ampoule was filled with $Mg(BHT)_2(THF)_2$ (121.4 mg, 0.2 mmol), benzyl alcohol (0.02 mL, 0.2 mmol), glycidyl propargyl ether (0.58 mL, 0.5 mmol) and maleic anhydride (490.3 mg, 0.5 mmol). The reagents were dissolved into toluene to a total monomer concentration of 2 M. The ampoule was sealed and heated at 80° C. for 24 h. The resultant polymer was recovered by precipitation in excess diethyl ether. After centrifugation, the crude product was dissolved into chloroform, then diethylamine was added into the mixture followed by reflux under $N_2$ for 24 hours. Finally, the mixture was washed with excess phosphate buffer saline solution (0.5 M), organic layers were combined and dried to get functionalized poly(GPE-co-MA) (Scheme 19).

Scheme 19
Synthesis of poly(glycidyl propargyl ether-co-maleic anhydride) (poly(GPE-co-MA)) and isomerization

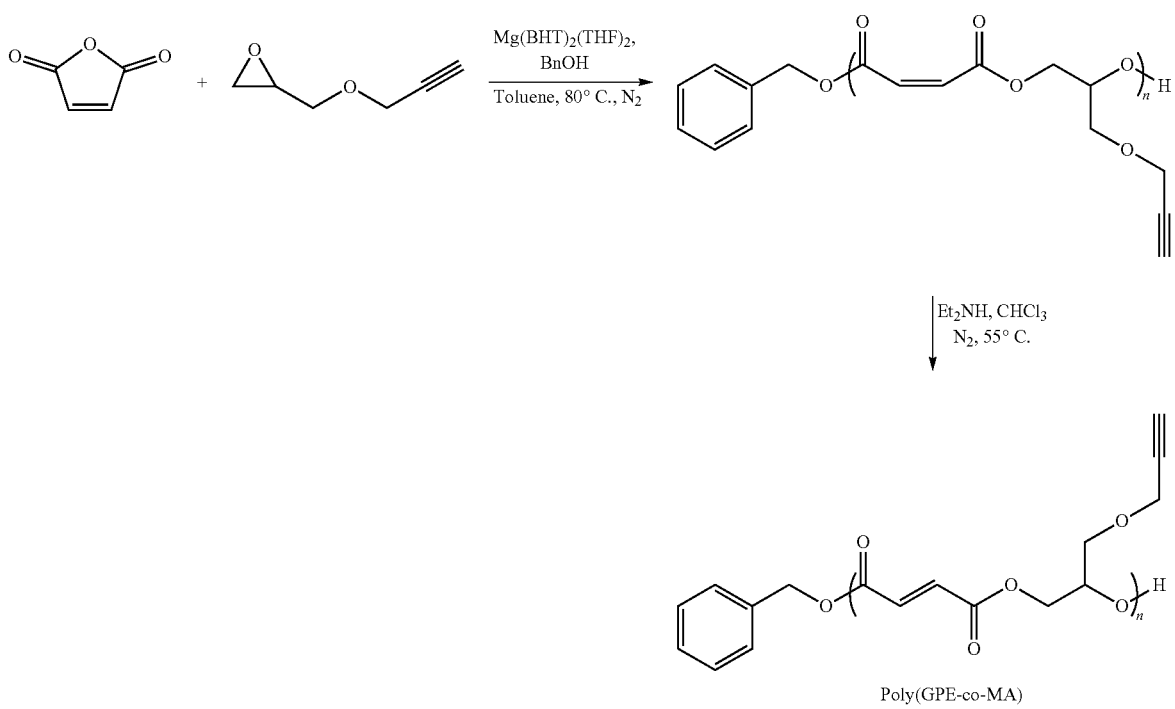

Poly(GPE-co-MA)

The resulting polymer was also characterized by $^1$H NMR (300 MHz, 303 K, CDCl$_3$): δ=7.36 (m, Ar), 6.86 (m, COHC=CHCO), 5.35 (m, OCH$_2$CH (CH$_2$OCH$_2$C≡CH)O), 5.22 (s, ArCH$_2$O), 4.80-4.40 (m, OCH$_2$CH (CH$_2$OCH$_2$C≡CH)O), 4.18 (m, OCH$_2$CH(CH$_2$OCH$_2$C≡CH)O), 3.74 (d, CH(CH$_2$OCH$_2$C≡CH)O), 2.49 (s, CH(CH$_2$OCH$_2$C≡CH)O) ppm and $^{13}$C NMR (125 MHz, 303K, CDCl$_3$): δ=164.20 (m, O—C=O), 133.79 (m, —C=C—), 79.12 (s, —C≡CH), 75.57 (s, 71.17 (s, —OCH$_2$CH—), 67.59 (s, —CH$_2$OCH$_2$C≡CH), 63.51 (s, CH$_2$CH(CH$_2$OCH$_2$C≡CH)O), 58.76 (s, —CH$_2$OCH$_2$C≡CH) ppm. (See FIGS. 30-32)

Example 25

Synthesis of Poly(2-[[(2-Nitrophenyl)Methoxyl]Methyl]Oxirane-Co-Maleic Anhydride Poly(2-[[(2-nitrophenyl)methoxyl]methyl]oxirane-co-maleic anhydride) was synthesized from 2-[[(2-nitrophenyl)methoxy]methyl]oxirane (NMMO) prepared (as set forth above in Example 19, above) and maleic anhydride as shown in Scheme 20, below.

Figure 33:
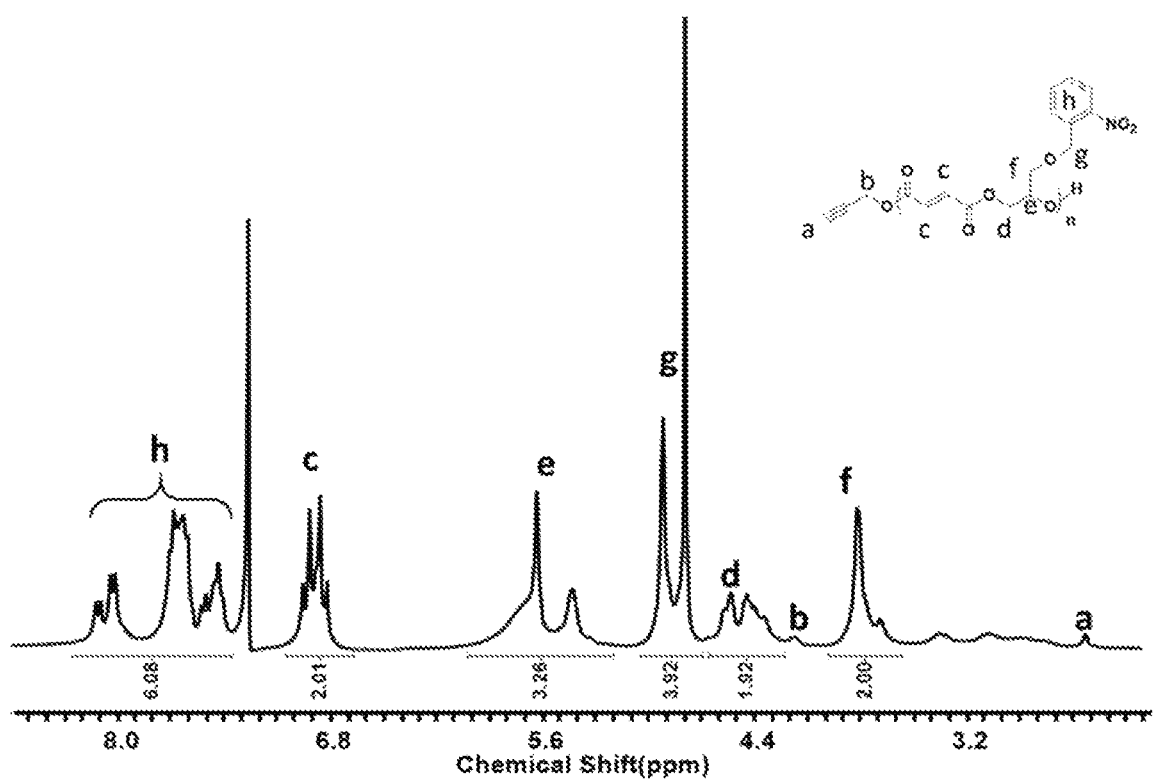
FIG. 33 is a $^1$H NMR spectrum of poly(NMMO-co-MA) (300 MHz, 303 K, CDCl$_3$).
Figure 34:
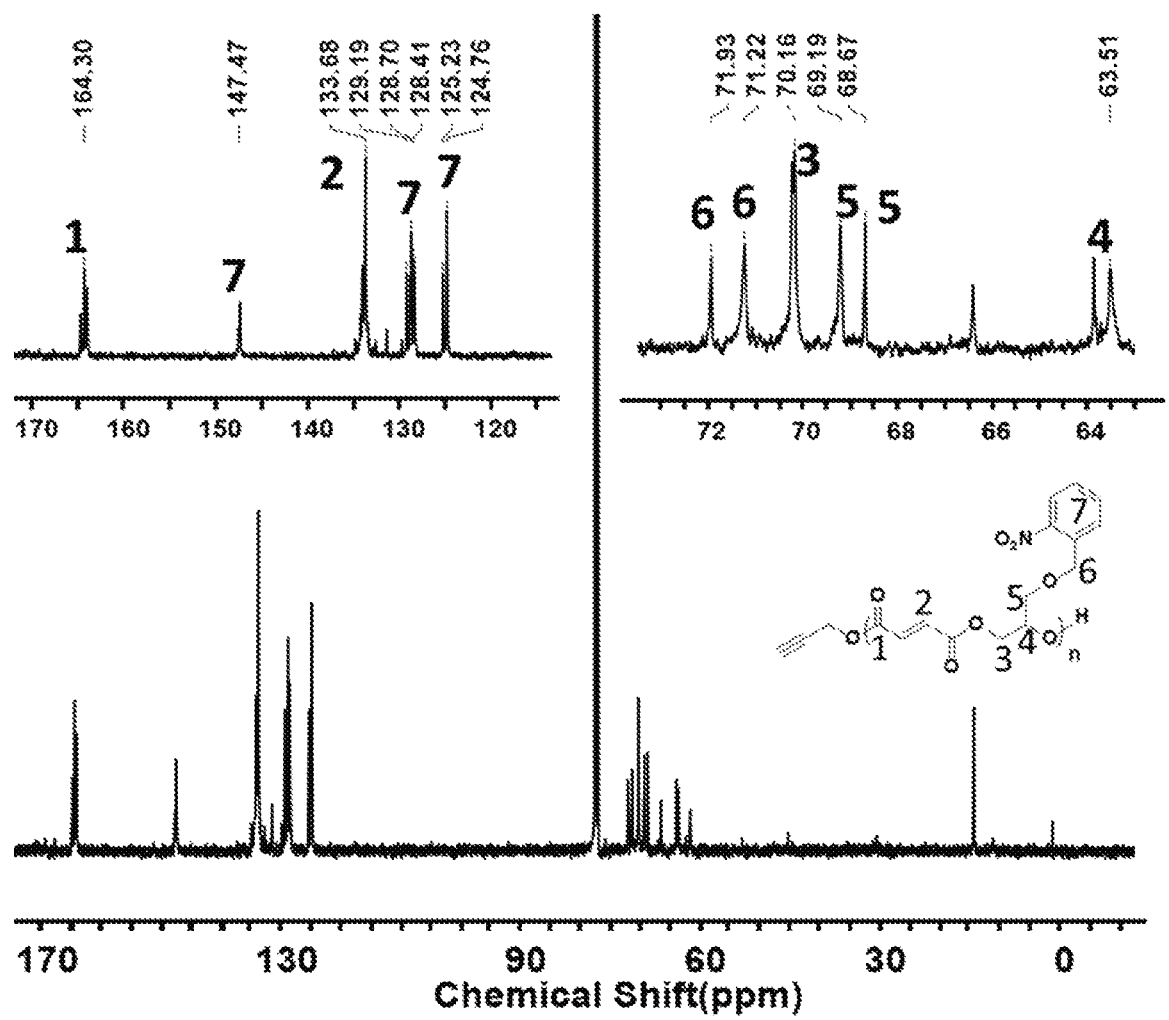
FIG. 34 is a $^{13}$C NMR spectrum of poly(NMMO-co-MA) (125 MHz, 303 K, CDCl$_3$).

The resulting polymer was characterized by $^1$H NMR and the results reported in Table 15, and in FIG. 33. $^1$H NMR (300 MHz, 303 K, CDCl$_3$): δ=7.98-7.38 (m, Ar), 6.27 (m, COHC=CHCO), 5.54-5.34 (d, OCH$_2$CH (CH$_2$OCH$_2$ArNO$_2$)O), 4.86 (s, OCH$_2$CH (CH$_2$OCH$_2$ArNO$_2$)O), 4.41 (s, OCH$_2$CH (CH$_2$OCH$_2$ArNO$_2$)O), 3.76 (m, OCH$_2$CH (CH$_2$OCH$_2$ArNO$_2$)O) ppm. The resulting polymer was also characterized by $^{13}$C NMR and the results reported here and in FIG. 34. $^{13}$C NMR (125 MHz, 303 K, CDCl$_3$): δ=163.99 (O—C=O), 147.47 (Ar C), 133.68 (HC=CH), 129.19-124.76 (m, Ar C), 71.93-71.22 (OCH$_2$CH(CH$_2$OCH$_2$Ar)O), 70.16 (OCH$_2$CH(CH$_2$OCH$_2$Ar)O), 69.19-68.67 (OCH$_2$CH(CH$_2$OCH$_2$Ar)O), 63.51 (OCH$_2$CH(CH$_2$OCH$_2$Ar)O) ppm.

The resulting polymer was characterized by Size Exclusion Chromatography (SEC). SEC (DMF): $M_n$=2.6 kDa, $M_w$=2.7 kDa, $Đ_M$=1.04.

The results of Example 25 are summarized in Table 15, below.

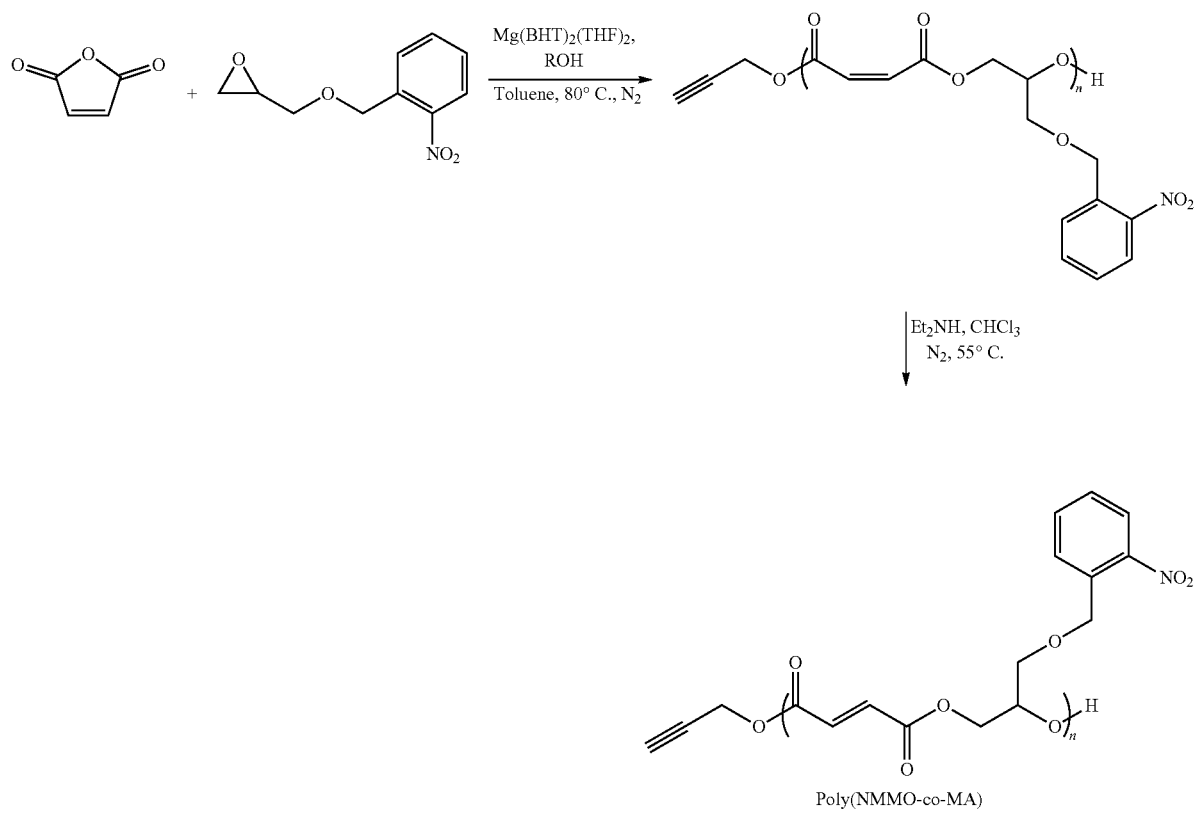

Scheme 20
Copolymerization of 2-[[(2-nitrophenyl)methoxyl]methyl]oxirane and maleic anhydride and isomerization of poly(NMMO-co-MA)

Poly(NMMO-co-MA)

TABLE 15

| | | P(NMMO-co-MA) | | | | | | |
|---|---|---|---|---|---|---|---|---|
| Initiator | mol. eq. catalyst | mol. eq. NMMO | mol. eq. MA | T (°C.) | Time (h) | $M_{n,\,NMR}$ (kDa) | $M_{n,\,GPC}$ (kDa) | $Đ_M$ |
| Propargyl alcohol | 1 | 25 | 25 | 80 | 24 | 7.8 | 2.6 | 1.04 |

Example 26

Synthesis of Poly(2-[[(2-Nitrophenyl)Methoxy]Methyl]Oxirane-Co-Maleic Anhydride) (Poly(NMMO-Co-MA))[7]

Poly(2-[[(2-nitrophenyl)methoxy]methyl]oxirane-co-maleic anhydride) (poly(NMMO-co-MA)) was synthesized as shown in Scheme 21, below.

The resulting polymer was characterized by $^1$H NMR (300 MHz, 303 K, CDCl$_3$): δ=7.98-7.38 (m, Ar), 6.27 (m, COHC=CHCO), 5.54-5.34 (d, OCH$_2$CH(CH$_2$OCH$_2$ArNO$_2$)O), 4.86 (s, OCH$_2$CH(CH$_2$OCH$_2$ArNO$_2$)O), 4.41 (s, OCH$_2$CH(CH$_2$OCH$_2$ArNO$_2$)O), 3.76 (m, OCH$_2$CH(CH$_2$OCH$_2$ArNO$_2$)O) ppm. The resulting polymer was also characterized by $^{13}$C NMR (125 MHz, 303K, CDCl$_3$): δ=163.99 (m, O—C=O), 147.47 (m, Ar), 133.68 (m,

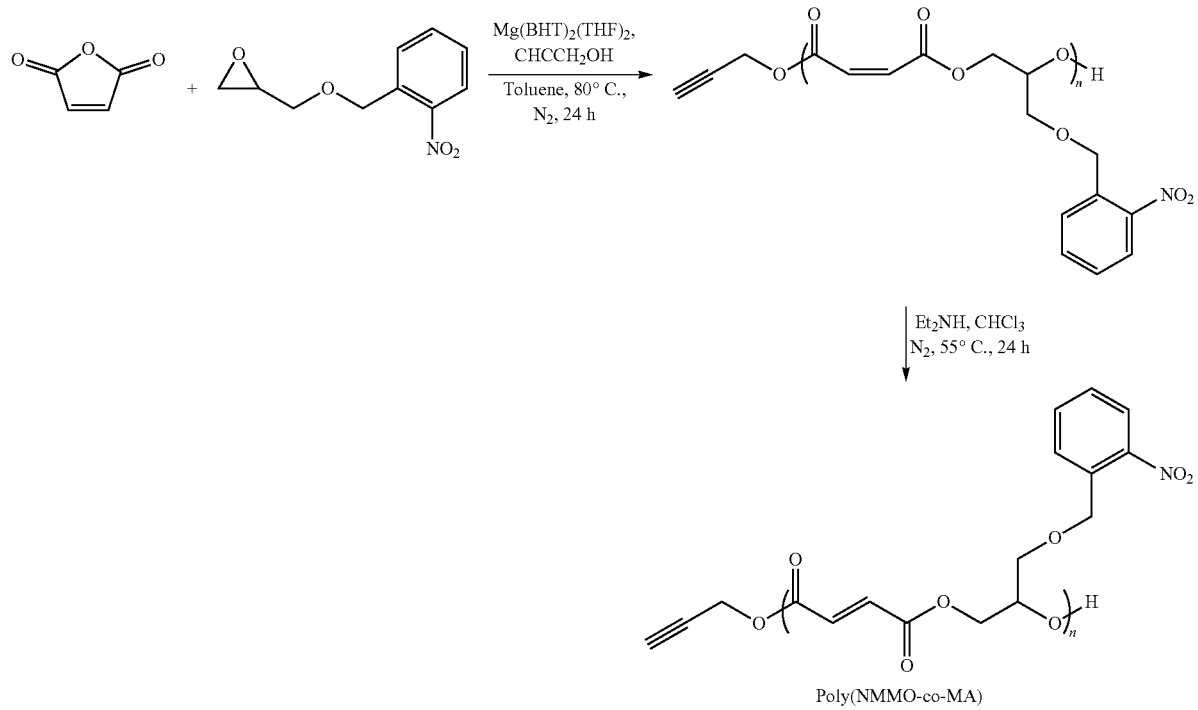

Scheme 21
Synthesis of poly(2-[[(2-nitrophenyl)methoxyl]methyl]oxirane-co-maleic anhydride) (poly(NMMO-co-MA)) and isomerization Poly(NMMO-co-MA)

Using standard Schlenk line techniques, an ampoule was filled with Mg(BHT)$_2$(THF)$_2$ (121.4 mg, 0.2 mmol), propargyl alcohol (0.01 mL, 0.2 mmol), o-nitrobenzyl alcohol (2.48 mL, 0.5 mmol) and maleic anhydride (490.3 mg, 0.5 mmol). The reagents were dissolved into toluene to a total monomer concentration of 2 M. The ampoule was sealed and heated at 80° C. for 24 h. The resultant polymer was recovered by precipitation in excess diethyl ether. After centrifugation, the crude product was dissolved into chloroform, then diethylamine was added into the mixture followed by reflux under N$_2$ for 24 hours. Finally, the mixture was washed with excess phosphate buffer saline solution (0.5 M), organic layers was combined and dried to yield poly(NMMO-co-MA) (Scheme 21).

—C=C—), 129.19-124.76 (m, Ar), 71.93-71.22 (d, OCH$_2$CH(CH$_2$OCH$_2$Ar)O), 70.16 (s, OCH$_2$CH(CH$_2$OCH$_2$Ar)O), 69.19-68.67 (d, OCH$_2$CH(CH$_2$OCH$_2$Ar)O), 63.51 (d, OCH$_2$CH(CH$_2$OCH$_2$Ar)O) ppm.

In light of the foregoing, it should be appreciated that the present invention significantly advances the art by providing a functionalized poly(propylene fumarate) polymer that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. An end and monomer functionalized poly(propylene fumarate) polymer comprising an isomerized residue of a maleic anhydride monomer and a functionalized propylene oxide monomer having the formula:

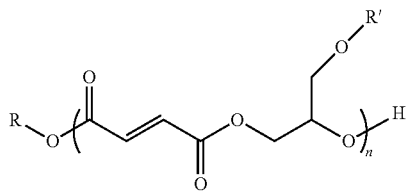

where n is an integer from more than 1 to 100; R is the residue of an initiating alcohol having a propargyl, norbornene, ketone or benzyl functional group; and R' is a second functional group selected from the group consisting of propargyl groups, 2-nitrophenyl groups, and combinations thereof.

2. The end and monomer functionalized poly(propylene fumarate) polymer of claim 1 having the formula:

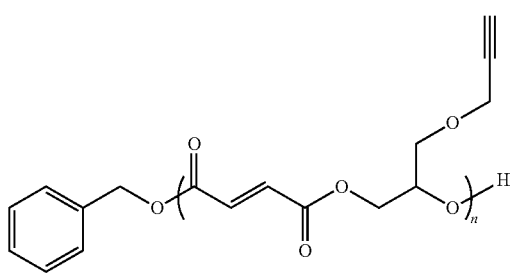

where n is an integer from about more than 1 to about 100.

3. The end and monomer functionalized poly(propylene fumarate) polymer of claim 1 having the formula:

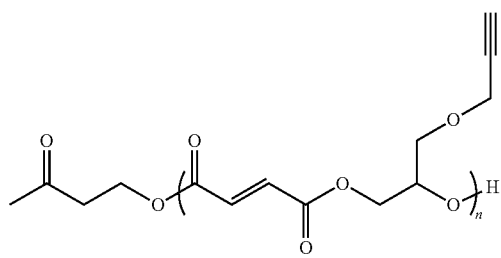

where n is an integer from about more than 1 to about 100.

4. The end and monomer functionalized poly(propylene fumarate) polymer of claim 1 having the formula:

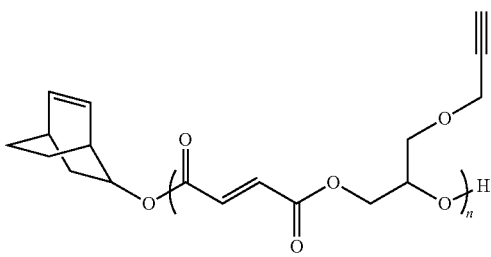

where n is an integer from about more than 1 to about 100.

5. The end and monomer functionalized poly(propylene fumarate) polymer of claim 1 having the formula:

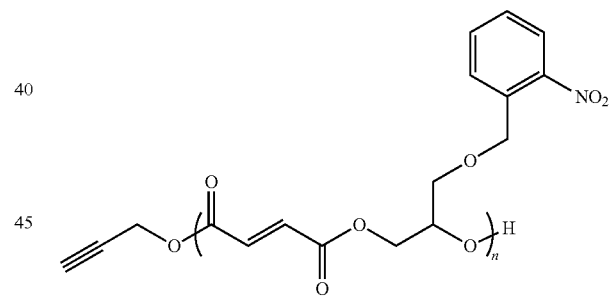

where n is an integer from about more than 1 to about 100.

6. The end and monomer functionalized poly(propylene fumarate) polymer of claim 1 having the formula:

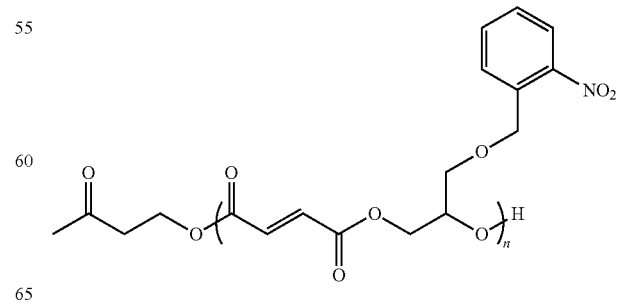

where n is an integer from about more than 1 to about 100.

7. The end and monomer functionalized polypropylene fumarate) polymer of claim 1 having the formula:
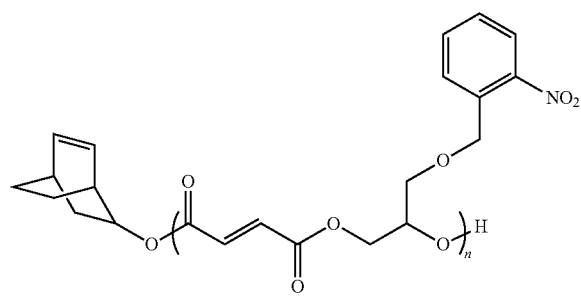
where n is an integer from about more than 1 to about 100.
8. The end and monomer functionalized poly(propylene fumarate) polymer of claim 1 having the formula:
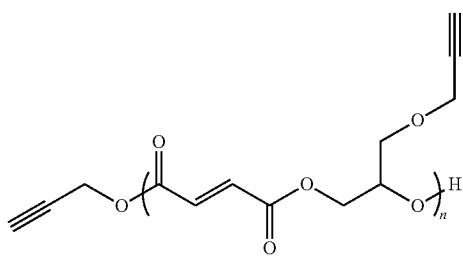
where n is an integer from about more than 1 to about 100.
* * * * *